(12) United States Patent
Lee et al.

(10) Patent No.: US 10,696,675 B2
(45) Date of Patent: Jun. 30, 2020

(54) IMIDAZOPYRIDOPYRIMIDINE DERIVATIVE COMPOUND AND USE THEREOF

(71) Applicant: HANMI PHARMACEUTICAL CO., LTD., Hwaseong-si, Gyeonggi-do (KR)

(72) Inventors: Moon Sub Lee, Hwaseong-si (KR); Eun Young Byun, Hwaseong-si (KR); Ji Sook Kim, Hwaseong-si (KR); Won Jeoung Kim, Hwaseong-si (KR); Nam Du Kim, Hwaseong-si (KR); Seung Hyun Jung, Hwaseong-si (KR); Young Gil Ahn, Hwaseong-si (KR)

(73) Assignee: HANMI PHARMACEUTICAL CO., LTD., Hwaseong-si (KR)

( * ) Notice: Subject to any disclaimer, the term of this patent is extended or adjusted under 35 U.S.C. 154(b) by 0 days.

(21) Appl. No.: 16/313,778

(22) PCT Filed: Jun. 28, 2017

(86) PCT No.: PCT/KR2017/006849
§ 371 (c)(1),
(2) Date: Dec. 27, 2018

(87) PCT Pub. No.: WO2018/004258
PCT Pub. Date: Jan. 4, 2018

(65) Prior Publication Data
US 2019/0152973 A1 May 23, 2019

(30) Foreign Application Priority Data

Jun. 28, 2016 (KR) .................. 10-2016-0080785
Jun. 27, 2017 (KR) .................. 10-2017-0081047

(51) Int. Cl.
*C07D 471/14* (2006.01)
*A61K 31/519* (2006.01)
*C07D 487/14* (2006.01)
*A61P 35/00* (2006.01)

(52) U.S. Cl.
CPC .......... *C07D 471/14* (2013.01); *A61K 31/519* (2013.01); *A61P 35/00* (2018.01); *C07D 487/14* (2013.01)

(58) Field of Classification Search
CPC ..... A61K 31/519; A61P 35/00; C07D 471/14; C07D 487/14
See application file for complete search history.

(56) References Cited

U.S. PATENT DOCUMENTS

2003/0232847 A1* 12/2003 Goldstein ............ C07D 471/14
514/267
2014/0088100 A1 3/2014 Bifulco, Jr. et al.

FOREIGN PATENT DOCUMENTS

| JP | 2006-503802 A | 2/2006 |
| KR | 10-2004-0099384 A | 11/2004 |
| WO | 01/29042 A1 | 4/2001 |
| WO | 2014/172425 A1 | 10/2014 |

OTHER PUBLICATIONS

Ping Chen et al., "Imidazoquinoxaline Src-Family Kinase p56$^{Lck}$ Inhibitors: SAR, QSAR, and the Discovery of (S)-N-(2-Chloro-6-methylphenyl)-2-(3-methyl-1-piperazinyl)imidazo-[1,5-a]pyrido[3,2-e]pyrazin-6-amine (BMS-279700) as a Potent and Orally Active Inhibitor with Excellent in Vivo Antiinflammatory Activity", Journal of Medicinal Chemistry, 2004, pp. 4517-4529., vol. 47, No. 18.
International Search Report for PCT/KR2017/006849 dated Oct. 20, 2017 (PCT/ISA/210).
Correspondence dated Dec. 24, 2019 from the Japanese Patent Office in Application No. 2018-568423.

* cited by examiner

*Primary Examiner* — Valerie Rodriguez-Garcia
(74) *Attorney, Agent, or Firm* — Sughrue Mion, PLLC

(57) ABSTRACT

A novel imidazopyridine derivative compound and uses thereof are disclosed. An imidazopyridopyridine derivative compound of Chemical Formula 1 having selective inhibitory activity for a fibroblast growth factor receptor (FGFR) and a pharmaceutical composition including the compound are disclosed:

Chemical Formula 1

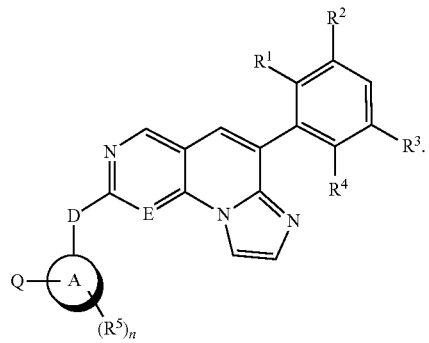

12 Claims, No Drawings

IMIDAZOPYRIDOPYRIMIDINE DERIVATIVE COMPOUND AND USE THEREOF

CROSS-REFERENCE(S) TO RELATED APPLICATIONS

This application is a National Stage of International Application No. PCT/KR2017/006849 filed Jun. 28, 2017, claiming priority based on Korean Patent Application Nos. 10-2016-0080785 and 10-2017-0081047, filed on Jun. 28, 2016 and Jun. 27, 2017, respectively, the invention of which is incorporated herein by reference in its entirety.

BACKGROUND OF THE INVENTION

Field of the Invention

Exemplary embodiments of the present invention relate to a novel heterocyclic derivative compound and a use thereof, and in particular, to a novel heterocyclic derivative compound having excellent selective inhibitory activity for a fibroblast growth factor receptor (FGFR) and a pharmaceutical composition including the compound preventing or treating various diseases relating to the FGFR.

Description of the Related Art

A fibroblast growth factor (FGF) series of signal transducing polypeptide controls a chain of various physiological functions such as mitogenesis, wound healing, cytodifferentiation, angiogenesis and development. FGF includes 22 structurally related polypeptide family having diversity of biological activities. Most of such signal transducing molecules function by binding to a homologous receptor thereof (referring to FGFR; FGFR1-4), a family of receptor tyrosine kinase, and activating the receptor (literature [Eswarakumar et al., 2005; Ornitz and Itoh, 2001]).

A different ligand-receptor pair in 22 FGF and 4 FGFR controls cell growth in a positive or negative way depending on the cell type and development stage (Dailey et al., Cytokine Growth Factor Rev. 16, 233-247; Eswarakumar et al. Cytokine Growth Factor Rev., 16, 139-149). When binding to the ligand, the receptor dimerizes a specific cytoplasmic tyrosine residue, and auto-phosphorylates or trans-phosphorylates to ultimately transduce intracellular signals reaching a nuclear transcription factor effector. Mitogenic signal by these FGF-FGFR is subsequently mediated by a number of channels including ras/raf/MAP kinase cascade (Ozawa et al., Teratog. Carcinog. Mutagen., 2001, 21, 27-44).

Such a FGF-FGFR signal transducing system performs an important role in generation and tissue recovery by controlling cell functioning/process, for example, growth, differentiation, migration, morphogenesis and angiogenesis. Accordingly, uncontrolled FGFR signaling network is involved in many types of human pathological states, and more specifically, changes in FGFR (that is, overexpression, mutation, dislocation and extremity amputation) are known to be involved in numerous human cancers including myeloma, breast, gastric, colorectal, vesical, pancreatic and hepatocellular cancers (literature [Bange et al., 2002; Cappellen et al., 1999; Chesi et al., 2001; Chesi et al., 1997; Gowardhan et al., 2005; Jaakkola et al., 1993; Jang et al., 2001; Jang et al., 2000; Jeffers et al., 2002; Xiao et al., 1998]).

Meanwhile, a fibroblast growth factor receptor 4 (FGF receptor 4 or FGFR4) preferentially binds to a fibroblast growth factor 19 (FGF19) selectively, and is known to control cell proliferation and anti-apoptosis. Such FGFR4 or FGF19 is expressed or overexpressed in a number of cancers (See, e.g., Dieci et al. 2013, Cancer Discovery, OF1-OF16). According to results of many studies, FGFR4 or FGF19 expression has been expected to be a phenotype considerably accelerating disease progression in cancer patients. When FGFR4 or FGF19 expression was reduced or knockdown, cell proliferation decreased and apoptosis increased (See, e.g., Wesche et al. 2011, Biochem J, 437; 199-213).

In addition, in FGFR4 gene transcription from a breast cancer cell line, metastasis from G to A produces glycine substitution by arginine at position 388 in a transmembrane domain of the receptor, and when examining clinical data of 84 breast cancer patients, a homozygous or heterozygous carrier of arg388 allelic gene was proved to have a significantly reduced disease-free survival (P=0.01) within 62 months of average follow-up period. Moreover, in 82 colorectal cancer patients, FGFR4 arg388 allelic gene was also related to early metastasis and progressed tumor lymphatic metastatic stages.

Expression or overexpression of FGF19, a selective ligand of FGFR4, is related to aggressiveness in a number of cancers such as liver cancer, skin cancer such as melanoma, rectal cancer and thyroid cancer. For example, FGF19 is overexpressed in 30% to 50% of liver cancer patients. When comparing progression-free survival (PFS) and overall survival (OS) between an overexpressed group and a group that was not overexpressed in liver cancer, a risk factor of the overexpressed group was turned out to be higher by 2.3 times to 3.6 times compared to the group that was not overexpressed (S. Miura et al., 2012, BMC Cancer, 12, 1471-2407).

Such results support the conclusion that FGFR4 represents an oncogene or a determinant considerably accelerating cancer progression in cancer patients (Bange et al., 2002, Cancer Res., 62, 840-847).

SUMMARY OF THE INVENTION

The present invention has been made in view of the above, and an object of the present invention is to provide a novel heterocyclic derivative compound having excellent selective inhibitory activity for a fibroblast growth factor receptor.

Another object of the present invention is to provide a pharmaceutical composition including the compound in a therapeutically effective amount.

However, objects of the present invention are not limited to the objects described above, and other objects that are not mentioned will be clearly understood to those skilled in the art from the descriptions provided below.

One aspect of the present invention provides a compound selected from the group consisting of heterocyclic derivative compounds of the following Chemical Formula 1, and a pharmaceutically acceptable salt, an optical isomer, a hydrate and a solvate thereof:

[Chemical Formula 1]

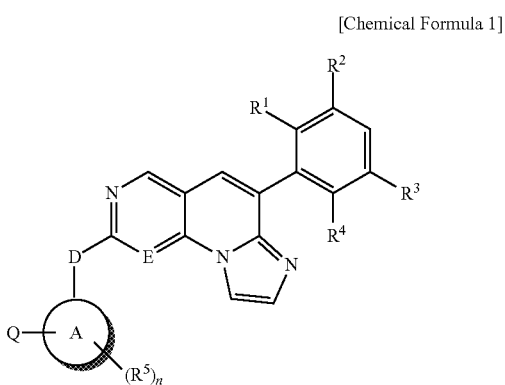

In Chemical Formula 1, $R^1$, $R^2$, $R^3$ and $R^4$ are each independently selected from the group consisting of H, halogen, $C_{1-4}$ alkyl and $C_{1-4}$ alkoxy;

E is CH or N;

D is NH or a bond;

Q is hydrogen or

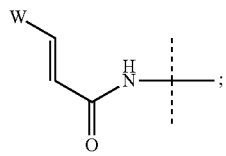

W is hydrogen, halogen or —$(CH_2)_p$ NR'R";

R' and R" are each independently selected from the group consisting of H or $C_{1-6}$ alkyl, and herein, R' and R" may bond to each other to form a $C_{3-6}$ alkylene bridge, and at least one methylene in the alkylene bridge is unsubstituted or substituted with one or more members selected from the group consisting of —O—, —S(O)—, —S(O)$_2$— and —N(R')—;

ring A is selected from the group consisting of aryl, heteroaryl, cycloalkyl and heterocyclyl, and herein, the heteroaryl means a 5-membered to 7-membered aromatic ring containing 1 to 3 heteroatoms selected from the group consisting of O, N and S, and the heterocyclyl means a 5-membered to 7-membered ring-type residue containing 1 to 3 heteroatoms or functional groups selected from the group consisting of N, O, S, SO and SO$_2$;

$R^5$ is selected from the group consisting of halogen, $C_{1-6}$ alkyl, $C_{2-6}$ alkenyl, $C_{2-6}$ alkynyl, —CN, —$(CH_2)_p$NR'R", —N(R')$(CH_2)_p$OR$^6$, —$(CH_2)_p$OR$^6$, aryl, heteroaryl, $C_{3-7}$ cycloalkyl, heterocyclyl, —$(CH_2)_p$C(=O)NR'R", —$(CH_2)_p$C(=O)R$^6$, —$(CH_2)_p$SR$^6$ and —$(CH_2)_p$SO$_2$R$^6$, and herein, the heterocyclyl means a 3-membered to 7-membered ring-type residue containing 1 to 3 heteroatoms or functional groups selected from the group consisting of N, O, S, SO and SO$_2$;

when there are a plurality of $R^5$s, these may be the same as or different from each other, and $R^5$s adjacent to each other may bond to each other to form a $C_{3-6}$ alkylene bridge, and at least one methylene in the alkylene bridge is unsubstituted or substituted with one or more members selected from the group consisting of —O—, —S(O)—, —S(O)$_2$— and —N(R')—;

$R^6$ is selected from the group consisting of hydrogen, halogen, hydroxy, $C_{1-6}$ alkyl, —$(CH_2)_q$NR'R", —$(CH_2)_q$ OR$^7$, $C_{3-7}$ cycloalkyl, heterocyclyl, —$(CH_2)_q$C(=O)R$^7$, —$(CH_2)_q$SR$^7$ and —$(CH_2)_q$SO$_2$R$^7$;

$R^7$ is selected from the group consisting of hydrogen, halogen, $C_{1-6}$ alkyl, $C_{3-7}$ cycloalkyl, heterocyclyl and —C(=O)R$^6$;

the $C_{1-6}$ alkyl, the cycloalkyl, the heterocyclyl, the aryl and the heteroaryl may be each independently unsubstituted or substituted with one or more types of substituents selected from the group consisting of halogen, hydroxy, —CN, linear or branched $C_{1-6}$ alkyl, halogenated $C_{1-6}$ alkyl, $C_{3-7}$ cycloalkyl and heterocyclyl;

the cycloalkyl and the heterocyclyl of $R^5$ to $R^{10}$, and the aryl and the heteroaryl of $R^5$ may be each independently unsubstituted or additionally substituted with one or more types of substituents selected from the group consisting of halogen, hydroxy, —CN, linear or branched $C_{1-6}$ alkyl, halogenated $C_{1-6}$ alkyl, —NR'R", $C_{1-6}$ alkoxy, —$(CH_2)_q$OR', —C(=O)$C_{3-7}$ cycloalkyl, $C_{3-7}$ cycloalkyl and heterocyclyl, and herein, R' and R" are each independently selected from the group consisting of H or $C_{1-6}$ alkyl;

p and q are each independently an integer of 0 to 6; and n is an integer of 0 to 4.

Another aspect of the present invention provides a pharmaceutical composition and a pharmaceutical formulation including the compound in a therapeutically effective amount for preventing and treating various diseases relating to the FGFR.

DESCRIPTION OF SPECIFIC EMBODIMENTS

Definitions listed below are definitions of various terms used for describing the present invention. These definitions are applied to the whole specification individually or as a part of terms including these unless limited otherwise.

The term 'halogen' used in the present specification means fluorine, chlorine, bromine or iodine unless mentioned otherwise.

The term 'hydroxy' used in the present specification means an —OH group unless mentioned otherwise.

The term 'alkyl' used in the present specification refers to a saturated, linear or branched hydrocarbon radical represented by $CnH_{2n+1}$ unless mentioned otherwise, and specifically refers to a saturated, linear or branched hydrocarbon radical each including 1 to 6 carbon atoms, 1 to 8 carbon atoms, 1 to 10 carbon atoms, or 1 to 20 carbon atoms. Examples of these radicals include methyl, ethyl, propyl, isopropyl, n-butyl, t-butyl, neopentyl, n-hexyl, heptyl, octyl radicals, but are not limited thereto. For example, the term '$C_{1-6}$ alkyl' used in the present specification means a linear or branched hydrocarbon residue having 1 to 6 carbon atoms unless mentioned otherwise.

Examples thereof may include methyl, ethyl, propyl, isopropyl, n-butyl, sec-butyl, t-butyl, n-pentyl, n-hexyl and the like, but are not limited thereto.

The term 'alkenyl' used in the present specification refers to a monovalent group derived from an unsaturated, linear or branched hydrocarbon moiety having at least one carbon-carbon double bond unless mentioned otherwise, and specifically refers to an unsaturated, linear or branched monovalent group each including 2 to 6, 2 to 8, 2 to 10, or 2 to 20 carbon atoms. Examples thereof may include ethenyl, propenyl, butenyl, 1-methyl-2-buten-1-yl, heptenyl, octenyl radicals, but are not limited thereto.

The term 'alkynyl' used in the present specification refers to a monovalent group derived from an unsaturated, linear or branched hydrocarbon moiety having at least one carbon-carbon triple bond unless mentioned otherwise.

The term 'alkoxy' used in the present specification refers to an oxygen radical represented by $OC_nH_{2n+1}$ having a monovalent group derived from a saturated, linear or branched hydrocarbon moiety each including 1 to 6, 1 to 8, 1 to 10, or 1 to 20 carbon atoms unless mentioned otherwise. For example, '$C_{1-6}$ alkoxy' means an oxygen radical having a linear or branched hydrocarbon residue having 1 to 6 carbon atoms unless mentioned otherwise. Examples thereof may include methoxy, ethoxy, propoxy, isopropoxy, n-butoxy, sec-butoxy, t-butoxy, pentoxy, hexoxy and the like, but are not limited thereto.

The term 'cycloalkyl' used in the present specification represents a monovalent group derived from a monocyclic or polycyclic saturated or partially unsaturated carbocyclic ring compound unless mentioned otherwise. For example, the term '$C_{3-7}$ cycloalkyl' used in the present specification means a ring-type hydrocarbon residue having 3 to 7 carbon atoms unless mentioned otherwise. Examples thereof may include cyclopropyl, cyclobutyl, cyclopentyl, cyclohexyl, cycloheptyl and the like, but are not limited thereto.

The term 'heterocyclyl' used in the present specification means a 3-membered to 7-membered ring-type residue containing 1 to 3 heteroatoms or functional groups selected from the group consisting of N, O, S, SO and $SO_2$ unless mentioned otherwise. Examples thereof may include oxetan-3-yl, tetrahydrofuran-3-yl, tetrahydro-2H-pyran-4-yl, tetrahydro-2H-pyran-3-yl, oxepan-4-yl, oxepan-3-yl, piperidin-1-yl, piperidin-3-yl, piperidin-4-yl, piperazin-1-yl, morpholin-4-yl, thiomorpholin-4-yl, 1,1-dioxidothiomorpholin-4-yl, pyrrolidin-1-yl, pyrrolidin-3-yl, azetidin-1-yl, azetidin-3-yl, aziridin-1-yl, azepan-1-yl, azepan-3-yl, azepan-4-yl and the like, but are not limited thereto.

The term 'aryl' used in the present specification refers to a mono- or poly-cyclic carbocyclic ring system having 6 to 14 carbon atoms having fused or non-fused one or more aromatic rings unless mentioned otherwise, and examples of the aryl may include phenyl, naphthyl, tetrahydronaphthyl, indenyl, anthracenyl and the like, but are not limited thereto.

The term 'heteroaryl' used in the present specification means a 5-membered to 12-membered, preferably 5-membered to 7-membered, monocyclic or bicyclic or higher aromatic group containing one or more heteroatoms such as 1 to 4, and preferably 1 to 3 heteroatoms selected from the group consisting of O, N and S unless mentioned otherwise. Examples of the monocyclic heteroaryl may include thiazolyl, oxazolyl, thiophenyl, furanyl, pyrrolyl, imidazolyl, isoxazolyl, pyrazolyl, triazolyl, thiadiazolyl, tetrazolyl, oxadiazolyl, pyridinyl, pyridazinyl, pyrimidinyl, pyrazinyl and groups similar thereto, but are not limited thereto. Examples of the bicyclic heteroaryl may include indolyl, benzothiophenyl, benzofuranyl, benzimidazolyl, benzoxazolyl, benzisoxazolyl, benzothiazolyl, benzothiadiazolyl, benzotriazolyl, quinolinyl, isoquinolinyl, furinyl, furopyridinyl and groups similar thereto, but are not limited thereto.

The term 'alkylene bridge' used in the present specification indicates a linear or branched divalent hydrocarbon bridge that links two different carbons having the same ring structure, may be formed with carbon and hydrogen, does not contain unsaturation, and preferably has 3 to 6 carbon atoms, such as propylene and n-butylene. The alkylene bridge may link any two carbons in the ring structure. In addition, at least one methylene in the alkylene bridge may be substituted with one or more members selected from the group consisting of —O—, —S—, —S(O)—, —S(O)$_2$— and —N(R')—, and herein, R' is hydrogen, $C_{1-6}$ alkyl, $C_{3-7}$ cycloalkyl or aryl.

The alkyl, the cycloalkyl, the heterocyclyl, the aryl and the heteroaryl used in the present invention may be each independently unsubstituted or additionally substituted with one or more types of substituents selected from the group consisting of halogen, hydroxy, —CN, linear or branched $C_{1-6}$ alkyl, halogenated $C_{1-6}$ alkyl, —NR'R", $C_{1-6}$ alkoxy, —(CH$_2$)$_q$OR', —C(=O)C$_{3-7}$ cycloalkyl, $C_{3-7}$ cycloalkyl and heterocyclyl, and herein, R' and R" are each independently selected from the group consisting of H or $C_{1-6}$ alkyl, and q is an integer of 0 to 6.

Hereinafter, the present invention will be described in more detail.

The present invention relates to a novel heterocyclic derivative compound of the following Chemical Formula 1 and a use thereof, and in particular, to a novel heterocyclic derivative compound having excellent selective inhibitory activity for a fibroblast growth factor receptor (FGFR), and a pharmaceutical composition including the compound preventing or treating various diseases relating to the FGFR.

Specifically, one embodiment of the present invention provides a compound selected from the group consisting of heterocyclic derivative compounds of the following Chemical Formula 1, and a pharmaceutically acceptable salt, an optical isomer, a hydrate and a solvate thereof:

[Chemical Formula 1]

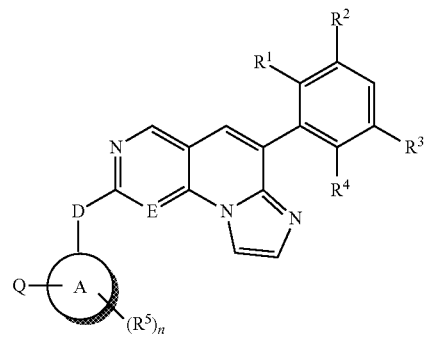

In Chemical Formula 1, $R^1$, $R^2$, $R^3$ and $R^4$ are each independently selected from the group consisting of H, halogen, $C_{1-4}$ alkyl and $C_{1-4}$ alkoxy;

E is CH or N;

D is NH or a bond;

Q is hydrogen or

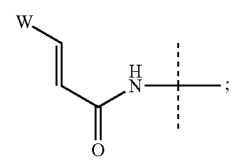

W is hydrogen, halogen or —(CH$_2$)$_p$NR'R";

R' and R" are each independently selected from the group consisting of H or $C_{1-6}$ alkyl, and herein, R' and R" may bond to each other to form a $C_{3-6}$ alkylene bridge, and at least one methylene in the alkylene bridge is unsubstituted or substituted with one or more members selected from the group consisting of —O—, —S(O)—, —S(O)$_2$— and —N(R')—;

ring A is selected from the group consisting of aryl, heteroaryl, cycloalkyl and heterocyclyl, and herein, the heteroaryl means a 5-membered to 7-membered aromatic ring containing 1 to 3 heteroatoms selected from the group consisting of O, N and S, and the heterocyclyl means a 5-membered to 7-membered ring-type residue containing 1 to 3 heteroatoms or functional groups selected from the group consisting of N, O, S, SO and SO$_2$;

R$^5$ is selected from the group consisting of halogen, C$_{1-6}$ alkyl, C$_{2-6}$ alkenyl, C$_{2-6}$ alkynyl, —CN, —(CH$_2$)$_p$NR'R", —N(R')(CH$_2$)$_p$OR$^6$, —(CH$_2$)$_p$OR$^6$, aryl, heteroaryl, C$_{3-7}$ cycloalkyl, heterocyclyl, —(CH$_2$)$_p$C(=O)NR'R", —(CH$_2$)$_p$C(=O)R$^6$, —(CH$_2$)$_p$SR$^6$ and —(CH$_2$)$_p$SO$_2$R$^6$, and herein, the heterocyclyl means a 3-membered to 7-membered ring-type residue containing 1 to 3 heteroatoms or functional groups selected from the group consisting of N, O, S, SO and SO$_2$;

when there are a plurality of R$^5$s, these may be the same as or different from each other, and R$^5$s adjacent to each other may bond to each other to form a C$_{3-6}$ alkylene bridge, and at least one methylene in the alkylene bridge is unsubstituted or substituted with one or more members selected from the group consisting of —O—, —S(O)—, —S(O)$_2$— and —N(R')—;

R$^6$ is selected from the group consisting of hydrogen, halogen, hydroxy, C$_{1-6}$ alkyl, —(CH$_2$)$_q$NR'R", —(CH$_2$)$_q$OR$^7$, C$_{3-7}$ cycloalkyl, heterocyclyl, —(CH$_2$)$_q$C(=O)R$^7$, —(CH$_2$)$_q$SR$^7$ and —(CH$_2$)$_q$SO$_2$R$^7$;

R$^7$ is selected from the group consisting of hydrogen, halogen, C$_{1-6}$ alkyl, C$_{3-7}$ cycloalkyl, heterocyclyl and —C(=O)R$^6$;

the C$_{1-6}$ alkyl, the cycloalkyl, the heterocyclyl, the aryl and the heteroaryl may be each independently unsubstituted or substituted with one or more types of substituents selected from the group consisting of halogen, hydroxy, —CN, linear or branched C$_{1-6}$ alkyl, halogenated C$_{1-6}$ alkyl, C$_{3-7}$ cycloalkyl and heterocyclyl;

the cycloalkyl and the heterocyclyl of R$^5$ to R$^{10}$, and the aryl and the heteroaryl of R$^5$ may be each independently unsubstituted or additionally substituted with one or more types of substituents selected from the group consisting of halogen, hydroxy, —CN, linear or branched C$_{1-6}$ alkyl, halogenated C$_{1-6}$ alkyl, —NR'R", C$_{1-6}$ alkoxy, —(CH$_2$)$_q$OR', —C(=O)C$_{3-7}$ cycloalkyl, C$_{3-7}$ cycloalkyl and heterocyclyl, and herein, R' and R" are each independently selected from the group consisting of H or C$_{1-6}$ alkyl;

p and q are each independently an integer of 0 to 6; and n is an integer of 0 to 4.

According to another embodiment of the present invention, E is N in the compound represented by Chemical Formula 1.

According to another embodiment of the present invention, the compound represented by Chemical Formula 1 may be represented by the following Chemical Formula 2 to Chemical Formula 5:

[Chemical Formula 2]

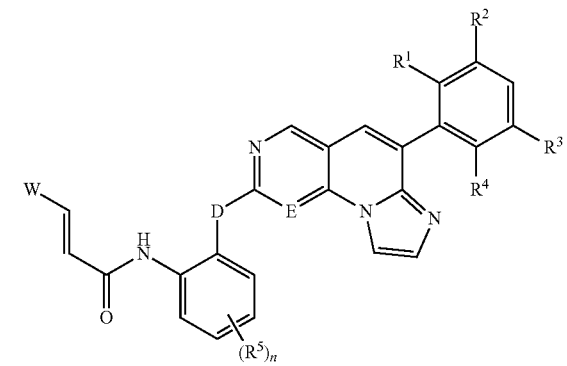

[Chemical Formula 3]

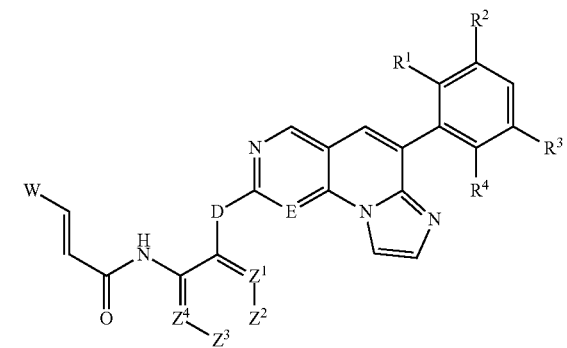

[Chemical Formula 4]

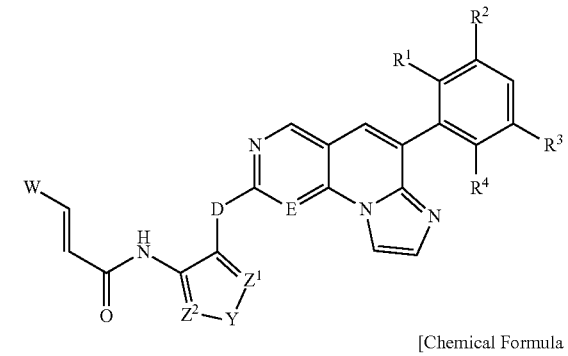

[Chemical Formula 5]

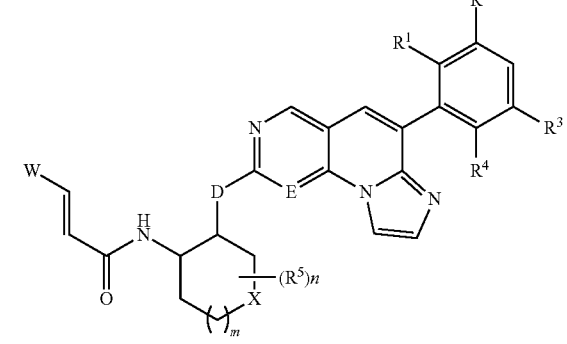

In Chemical Formula 2 to Chemical Formula 5,

X is selected from the group consisting of O, S, NH and CH$_2$;

m is an integer of 0 to 2;

one or more of Z$^1$ to Z$^4$ are N, and the rest are each independently N or C(R$^5$);

Y is selected from the group consisting of O, S and N(R$^5$); and

R$^1$ to R$^5$, D, E, W, and n have the same definitions as in Chemical Formula 1.

According to another embodiment of the present invention, in the compound represented by Chemical Formula 3, only any one of Z$^1$ to Z$^4$ is N, and the rest are C(R$^5$).

According to another embodiment of the present invention, in the compound represented by Chemical Formula 4, Y is N(R$^5$), and only any one of Z$^1$ and Z$^2$ is N.

Preferred examples of the compound of Chemical Formula 1 are as follows, but are not limited thereto:

N-(2-((6-(2,6-dichloro-3,5-dimethoxyphenyl)imidazo[1',2':1,6]pyrido[2,3-d]pyrimidin-2-yl)amino)cyclopentyl)acrylamide;

N-(4-((6-(2,6-dichloro-3,5-dimethoxyphenyl)imidazo[1',2':1,6]pyrido[2,3-d]pyrimidin-2-yl)amino)cyclohexyl)acrylamide;

N-(4-((6-(2,6-dichloro-3,5-dimethoxyphenyl)imidazo[1',2':1,6]pyrido[2,3-d]pyrimidin-2-yl)amino)tetrahydrofuran-3-yl)acrylamide;

N-((3S,4S)-3-((6-(2,6-dichloro-3,5-dimethoxyphenyl)imidazo[1',2':1,6]pyrido[2,3-d]pyrimidin-2-yl)amino)tetrahydro-2H-pyran-4-yl)acrylamide;

N-((3S,4S)-3-((6-(2,6-difluoro-3,5-dimethoxyphenyl)imidazo[1',2':1,6]pyrido[2,3-d]pyrimidin-2-yl)amino)tetrahydro-2H-pyran-4-yl)acrylamide;

N-(2-((6-(2,6-dichloro-3,5-dimethoxyphenyl)imidazo[1',2':1,6]pyrido[2,3-d]pyrimidin-2-yl)amino)phenyl)acrylamide;

N-(3-((6-(2,6-dichloro-3,5-dimethoxyphenyl)imidazo[1',2':1,6]pyrido[2,3-d]pyrimidin-2-yl)amino)phenyl)acrylamide;

N-(2-((6-(3,5-dimethoxyphenyl)imidazo[1',2':1,6]pyrido[2,3-d]pyrimidin-2-yl)amino)-3-methylphenyl)acrylamide;

N-(2-((6-(2,6-dichloro-3,5-dimethoxyphenyl)imido[1',2':1,6]pyrido[2,3-d]pyrimidin-2-yl)amino)-3-methylphenyl)acrylamide;

N-(2-((6-(2,6-dichloro-3,5-dimethoxyphenyl)imidazo[1',2':1,6]pyrido[2,3-d]pyrimidin-2-yl)amino)-3-fluorophenyl)acrylamide;

N-(2-((6-(2,6-dichloro-3,5-dimethoxyphenyl)imidazo[1',2':1,6]pyrido[2,3-d]pyrimidin-2-yl)amino)-3-methoxyphenyl)acrylamide;

N-(2-((6-(2,6-dichloro-3,5-dimethoxyphenyl)imidazo[1',2':1,6]pyrido[2,3-d]pyrimidin-2-yl)amino)-4-fluorophenyl)acrylamide;

N-(2-((6-(2,6-dichloro-3,5-dimethoxyphenyl)imidazo[1',2':1,6]pyrido[2,3-d]pyrimidin-2-yl)amino)-4-(4-ethylpiperazin-1-yl)phenyl)acrylamide;

N-(2-((6-(2,6-dichloro-3,5-dimethoxyphenyl)imidazo[1',2':1,6]pyrido[2,3-d]pyrimidin-2-yl)amino)-5-fluorophenyl)acrylamide;

N-(5-chloro-2-((6-(2,6-dichloro-3,5-dimethoxyphenyl)imidazo[1',2':1,6]pyrido[2,3-d]pyrimidin-2-yl)amino)phenyl)acrylamide;

N-(2-((6-(2,6-dichloro-3,5-dimethoxyphenyl)imidazo[1',2':1,6]pyrido[2,3-d]pyrimidin-2-yl)amino)-5-ethynylphenyl)acrylamide;

N-(5-cyano-2-((6-(2,6-dichloro-3,5-dimethoxyphenyl)imidazo[1',2':1,6]pyrido[2,3-d]pyrimidin-2-yl)amino)phenyl)acrylamide;

N-(2-((6-(2,6-dichloro-3,5-dimethoxyphenyl)imidazo[1',2':1,6]pyrido[2,3-d]pyrimidin-2-yl)amino)-5-(methylsulfonyl)phenyl)acrylamide;

N-(2-((6-(2,6-dichloro-3,5-dimethoxyphenyl)imidazo[1',2':1,6]pyrido[2,3-d]pyrimidin-2-yl)amino)-5-methylphenyl)acrylamide;

N-(2-((6-(2,6-dichloro-3,5-dimethoxyphenyl)imidazo[1',2':1,6]pyrido[2,3-d]pyrimidin-2-yl)amino)-5-ethylphenyl)acrylamide;

N-(5-cyclopropyl-2-((6-(2,6-dichloro-3,5-dimethoxyphenyl)imidazo[1',2':1,6]pyrido[2,3-d]pyrimidin-2-yl)amino)phenyl)acrylamide;

N-(2-((6-(2,6-dichloro-3,5-dimethoxyphenyl)imidazo[1',2':1,6]pyrido[2,3-d]pyrimidin-2-yl)amino)-5-isopropylphenyl)acrylamide;

N-(2-((6-(2,6-dichloro-3,5-dimethoxyphenyl)imidazo[1',2':1,6]pyrido[2,3-d]pyrimidin-2-yl)amino)-5-(1-methylpiperidin-4-yl)phenyl)acrylamide;

N-(2-((6-(2,6-dichloro-3,5-dimethoxyphenyl)imidazo[1',2':1,6]pyrido[2,3-d]pyrimidin-2-yl)amino)-5-(dimethylamino)phenyl)acrylamide;

N-(2-((6-(2,6-dichloro-3,5-dimethoxyphenyl)imidazo[1',2':1,6]pyrido[2,3-d]pyrimidin-2-yl)amino)-5-((2-methoxyethyl)(methyl)amino)phenyl)acrylamide;

N-(2-((6-(2,6-dichloro-3,5-dimethoxyphenyl)imidazo[1',2':1,6]pyrido[2,3-d]pyrimidin-2-yl)amino)-5-methoxyphenyl)acrylamide;

N-(2-((6-(2,6-dichloro-3,5-dimethoxyphenyl)imidazo[1',2':1,6]pyrido[2,3-d]pyrimidin-2-yl)amino)-5-ethoxyphenyl)acrylamide;

N-(2-((6-(2,6-dichloro-3,5-dimethoxyphenyl)imidazo[1',2':1,6]pyrido[2,3-d]pyrimidin-2-yl)amino)-5-isopropoxyphenyl)acrylamide;

N-(2-((6-(2,6-dichloro-3,5-dimethoxyphenyl)imidazo[1',2':1,6]pyrido[2,3-d]pyrimidin-2-yl)amino)-5-(2-methoxyethoxy)phenyl)acrylamide;

N-(2-((6-(2,6-dichloro-3,5-dimethoxyphenyl)imidazo[1',2':1,6]pyrido[2,3-d]pyrimidin-2-yl)amino)-5-(2-(dimethylamino)ethoxy)phenyl)acrylamide;

N-(2-((6-(2,6-dichloro-3,5-dimethoxyphenyl)imidazo[1',2':1,6]pyrido[2,3-d]pyrimidin-2-yl)amino)-5-(4-ethylpiperazin-1-yl)phenyl)acrylamide;

N-(2-((6-(2,6-dichloro-3,5-dimethoxyphenyl)imidazo[1',2':1,6]pyrido[2,3-d]pyrimidin-2-yl)amino)-5-morpholinophenyl)acrylamide;

N-(2-((6-(2,6-dichloro-3,5-dimethoxyphenyl)imidazo[1',2':1,6]pyrido[2,3-d]pyrimidin-2-yl)amino)-5-(pyrrolidin-1-yl)phenyl)acrylamide;

(E)-N-(2-((6-(2,6-dichloro-3,5-dimethoxyphenyl)imidazo[1',2':1,6]pyrido[2,3-d]pyrimidin-2-yl)amino)-5-morpholinophenyl)-4-(dimethylamino)but-2-eneamide;

N-(2-((6-(2,6-dichloro-3,5-dimethoxyphenyl)imidazo[1',2':1,6]pyrido[2,3-d]pyrimidin-2-yl)amino)-5-(4-(methylsulfonyl)piperazin-1-yl)phenyl)acrylamide;

N-(2-((6-(2,6-dichloro-3,5-dimethoxyphenyl)imidazo[1',2':1,6]pyrido[2,3-d]pyrimidin-2-yl)amino)-5-(1,1-dioxidothiomorpholino)phenyl)acrylamide;

N-(2-((6-(2,6-dichloro-3,5-dimethoxyphenyl)imidazo[1',2':1,6]pyrido[2,3-d]pyrimidin-2-yl)amino)-5-(3-methoxyazetidin-1-yl)phenyl)acrylamide;

N-(2-((6-(2,6-dichloro-3,5-dimethoxyphenyl)imidazo[1',2':1,6]pyrido[2,3-d]pyrimidin-2-yl)amino)-5-((2S,6R)-2,6-dimethylmorpholino)phenyl)acrylamide;

N-(2-((6-(2,6-dichloro-3,5-dimethoxyphenyl)imidazo[1',2':1,6]pyrido[2,3-d]pyrimidin-2-yl)amino)-5-(piperazin-1-yl)phenyl)acrylamide trifluoroacetate;

N-(2-((6-(2,6-dichloro-3,5-dimethoxyphenyl)imidazo[1',2':1,6]pyrido[2,3-d]pyrimidin-2-yl)amino)-5-(4-methoxypiperidin-1-yl)phenyl)acrylamide;

N-(2-((6-(2,6-dichloro-3,5-dimethoxyphenyl)imidazo[1',2':1,6]pyrido[2,3-d]pyrimidin-2-yl)amino)-5-(3-methoxypyrrolidin-1-yl)phenyl)acrylamide;

N-(5-(4-(cyclopropanecarbonyl)piperazin-1-yl)-2-((6-(2,6-dichloro-3,5-dimethoxyphenyl)imidazo[1',2':1,6]pyrido[2,3-d]pyrimidin-2-yl)amino)phenyl)acrylamide;

N-(5-(4-(cyclopropylmethyl)piperazin-1-yl)-2-((6-(2,6-dichloro-3,5-dimethoxyphenyl)imidazo[1',2':1,6]pyrido[2,3-d]pyrimidin-2-yl)amino)phenyl)acrylamide;

(S)—N-(2-((6-(2,6-dichloro-3,5-dimethoxyphenyl)imidazo[1',2':1,6]pyrido[2,3-d]pyrimidin-2-yl)amino)-5-(3-methoxypyrrolidin-1-yl)phenyl)acrylamide;

N-(2-((6-(2,6-dichloro-3,5-dimethoxyphenyl)imidazo[1',2':1,6]pyrido[2,3-d]pyrimidin-2-yl)amino)-5-(3-hydroxyazetidin-1-yl)phenyl)acrylamide;

N-(2-((6-(2,6-dichloro-3,5-dimethoxyphenyl)imidazo[1',2':1,6]pyrido[2,3-d]pyrimidin-2-yl)amino)-5-(4-(2-methoxyethyl)piperazin-1-yl)phenyl)acrylamide;

(Z)-3-chloro-N-(2-((6-(2,6-dichloro-3,5-dimethoxyphenyl)imidazo[1',2':1,6]pyrido[2,3-d]pyrimidin-2-yl)amino)-5-morpholinophenyl)acrylamide;

(S)—N-(2-((6-(2,6-dichloro-3,5-dimethoxyphenyl)imidazo[1',2':1,6]pyrido[2,3-d]pyrimidin-2-yl)amino)-5-(3-(dimethylamino)pyrrolidin-1-yl)phenyl)acrylamide;

N-(2-((6-(2,6-dichloro-3,5-dimethoxyphenyl)imidazo[1',2':1,6]pyrido[2,3-d]pyrimidin-2-yl)amino)-5-(2-methylmorpholino)phenyl)acrylamide;

(S)—N-(2-((6-(2,6-dichloro-3,5-dimethoxyphenyl)imidazo[1',2':1,6]pyrido[2,3-d]pyrimidin-2-yl)amino)-5-(2-(methoxymethyl)pyrrolidin-1-yl)phenyl)acrylamide;

N-(5-(4-cyclopropylpiperazin-1-yl)-2-((6-(2,6-dichloro-3,5-dimethoxyphenyl)imidazo[1',2':1,6]pyrido[2,3-d]pyrimidin-2-yl)amino)phenyl)acrylamide;

N-(2-((6-(2,6-dichloro-3,5-dimethoxyphenyl)imidazo[1',2':1,6]pyrido[2,3-d]pyrimidin-2-yl)amino)-5-(4-methylpiperazin-1-yl)phenyl)acrylamide;

(R)—N-(2-((6-(2,6-dichloro-3,5-dimethoxyphenyl)imidazo[1',2':1,6]pyrido[2,3-d]pyrimidin-2-yl)amino)-5-((tetrahydrofuran-3-yl)oxy)phenyl)acrylamide;

N-(5-(cyclopentyloxy)-2-((6-(2,6-dichloro-3,5-dimethoxyphenyl)imidazo[1',2':1,6]pyrido[2,3-d]pyrimidin-2-yl)amino)phenyl)acrylamide;

N-(2-((6-(2,6-dichloro-3,5-dimethoxyphenyl)imidazo[1',2':1,6]pyrido[2,3-d]pyrimidin-2-yl)amino)-5-((1-(2,2,2-trifluoroethyl)piperidin-4-yl)oxy)phenyl)acrylamide;

N-(2-((6-(2,6-dichloro-3,5-dimethoxyphenyl)imidazo[1',2':1,6]pyrido[2,3-d]pyrimidin-2-yl)amino)-5-((1-ethylpiperidin-4-yl)oxy)phenyl)acrylamide;

N-(6-((6-(2,6-dichloro-3,5-dimethoxyphenyl)imidazo[1',2':1,6]pyrido[2,3-d]pyrimidin-2-yl)amino)-2,3-dihydro-1H-inden-5-yl)acrylamide;

N-(2-((6-(2,6-dichloro-3,5-dimethoxyphenyl)imidazo[1',2':1,6]pyrido[2,3-d]pyrimidin-2-yl)amino)-3,5-dimethylphenyl)acrylamide;

(R)—N-(2-((6-(2,6-dichloro-3,5-dimethoxyphenyl)imidazo[1',2':1,6]pyrido[2,3-d]pyrimidin-2-yl)amino)-4-fluoro-5-((tetrahydrofuran-3-yl)oxy)phenyl)acrylamide;

(R)—N-(2-((6-(2,6-dichloro-3,5-dimethoxyphenyl)imidazo[1',2':1,6]pyrido[2,3-d]pyrimidin-2-yl)amino)-4-methyl-5-((tetrahydrofuran-3-yl)oxy)phenyl)acrylamide;

N-(2-((6-(2,6-dichloro-3,5-dimethoxyphenyl)imidazo[1',2':1,6]pyrido[2,3-d]pyrimidin-2-yl)amino)-4-methyl-5-morpholinophenyl)acrylamide;

N-(2-((6-(2,6-dichloro-3,5-dimethoxyphenyl)imidazo[1',2':1,6]pyrido[2,3-d]pyrimidin-2-yl)amino)-4-fluoro-5-((1-methylpiperidin-4-yl)oxy)phenyl)acrylamide;

N-(2-((6-(2,6-dichloro-3,5-dimethoxyphenyl)imidazo[1',2':1,6]pyrido[2,3-d]pyrimidin-2-yl)amino)-3-methyl-5-morpholinophenyl)acrylamide;

N-(2-((6-(2,6-dichloro-3,5-dimethoxyphenyl)imidazo[1',2':1,6]pyrido[2,3-d]pyrimidin-2-yl)amino)-5-fluoro-3-methylphenyl)acrylamide;

N-(2-((6-(2,6-dichloro-3,5-dimethoxyphenyl)imidazo[1',2':1,6]pyrido[2,3-d]pyrimidin-2-yl)amino)-3-methoxy-5-morpholinophenyl)acrylamide;

N-(2-((6-(2,6-dichloro-3,5-dimethoxyphenyl)imidazo[1',2':1,6]pyrido[2,3-d]pyrimidin-2-yl)amino)-5-(4-ethylpiperazin-1-yl)-3-fluorophenyl)acrylamide;

N-(2-((6-(2,6-dichloro-3,5-dimethoxyphenyl)imidazo[1',2':1,6]pyrido[2,3-d]pyrimidin-2-yl)amino)-3-fluoro-5-morpholinophenyl)acrylamide;

N-(3-chloro-2-((6-(2,6-dichloro-3,5-dimethoxyphenyl)imidazo[1',2':1,6]pyrido[2,3-d]pyrimidin-2-yl)amino)-5-morpholinophenyl)acrylamide;

N-(2-((6-(2,6-dichloro-3,5-dimethoxyphenyl)imidazo[1',2':1,6]pyrido[2,3-d]pyrimidin-2-yl)amino)pyridin-3-yl)acrylamide;

N-(2-((6-(2,6-dichloro-3,5-dimethoxyphenyl)imidazo[1',2':1,6]pyrido[2,3-d]pyrimidin-2-yl)amino)-5-morpholinopyridin-3-yl)acrylamide;

N-(3-((6-(2,6-dichloro-3,5-dimethoxyphenyl)imidazo[1',2':1,6]pyrido[2,3-d]pyrimidin-2-yl)amino)-1-methyl-1H-pyrazol-4-yl)acrylamide; N-(2-((6-(2,6-difluoro-3,5-dimethoxyphenyl)imidazo[1',2':1,6]pyrido[2,3-d]pyrimidin-2-yl)amino)-3-fluorophenyl)acrylamide;

N-(2-((6-(2,6-difluoro-3,5-dimethoxyphenyl)imidazo[1',2':1,6]pyrido[2,3-d]pyrimidin-2-yl)amino)-5-morpholinophenyl)acrylamide;

N-(3-((6-(2,6-difluoro-3,5-dimethoxyphenyl)imidazo[1',2':1,6]pyrido[2,3-d]pyrimidin-2-yl)amino)phenyl)acrylamide;

N-(2-((6-(2,6-difluoro-3,5-dimethoxyphenyl)imidazo[1',2':1,6]pyrido[2,3-d]pyrimidin-2-yl)amino)phenyl) acrylamide;

N-(2-((6-(2,6-difluoro-3,5-dimethoxyphenyl)imidazo[1',2':1,6]pyrido[2,3-d]pyrimidin-2-yl)amino)-3,5-difluorophenyl) acrylamide;

N-(2-((6-(2,6-difluoro-3,5-dimethoxyphenyl)imidazo[1',2':1,6]pyrido[2,3-d]pyrimidin-2-yl)amino)-4,5-difluorophenyl) acrylamide;

N-(2-((6-(2,6-difluoro-3,5-dimethoxyphenyl)imidazo[1',2':1,6]pyrido[2,3-d]pyrimidin-2-yl)amino)-3,4-difluorophenyl) acrylamide;

N-(3-chloro-2-((6-(2,6-difluoro-3,5-dimethoxyphenyl)imidazo[1',2':1,6]pyrido[2,3-d]pyrimidin-2-yl)amino)phenyl)acrylamide;

4-(3-(6-(2,6-dichloro-3,5-dimethoxyphenyl)imidazo[1',2':1,6]pyrido[2,3-d]pyrimidin-2-yl)phenyl)morpholine;

4-(5-(6-(2,6-dichloro-3,5-dimethoxyphenyl)imidazo[1',2':1,6]pyrido[2,3-d]pyrimidin-2-yl)pyridin-3-yl)morpholine;

N-(3-(6-(2,6-dichloro-3,5-dimethoxyphenyl)imidazo[1',2':1,6]pyrido[2,3-d]pyrimidin-2-yl)-5-morpholinophenyl)acrylamide;

N-(2-((4-(2,6-dichloro-3,5-dimethoxyphenyl)imidazo[1,2-a][1,6]naphthyridin-8-yl)amino)-5-morpholinophenyl)acrylamide;

N-(2-((4-(2,6-dichloro-3,5-dimethoxyphenyl)imidazo[1,2-a][1,6]naphthyridin-8-yl)amino)-5-((2S,6R)-2,6-dimethylmorpholino)phenyl) acrylamide;

N-(2-((4-(2,6-dichloro-3,5-dimethoxyphenyl)imidazo[1,2-a][1,6]naphthyridin-8-yl)amino)-5-(4-ethylpiperazin-1-yl)phenyl)acrylamide;

N-(2-((4-(2,6-dichloro-3,5-dimethoxyphenyl)imidazo[1,2-a][1,6]naphthyridin-8-yl)amino)-5-morpholinopyridin-3-yl)acrylamide; and N-(3-((4-(2,6-dichloro-3,5-dimethoxyphenyl)imidazo[1,2-a][1,6]naphthyridin-8-yl)amino)-1-methyl-1H-pyrazol-4-yl)acrylamide.

Methods of preparing the compound represented by Chemical Formula 1 are not particularly limited, and for example, the compound represented by Chemical Formula 1 may be synthesized using a preparation method of the following Reaction Formula 1, 2, 3, 4 or 5:

[Reaction Formula 1]

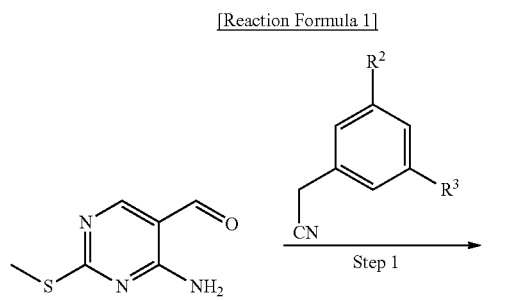

Chemical Formula 4

Step 1

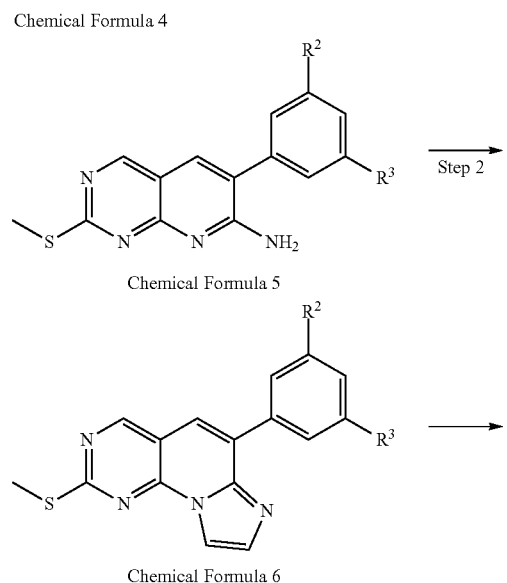

Chemical Formula 5

Chemical Formula 6

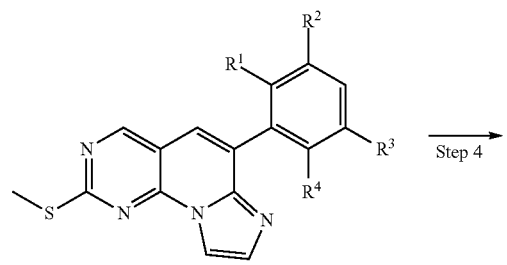

Chemical Formula 7

Step 4

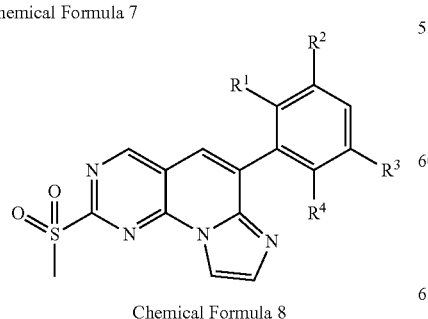

Chemical Formula 8

In Reaction Formula 1, $R^1$, $R^2$, $R^3$ and $R^4$ each have the same definition as in Chemical Formula 1.

In Reaction Formula 1, the compound represented by Chemical Formula 5 is synthesized through a condensation reaction of the compound of Chemical Formula 4 and 2-phenylacetonitrile having two substituents at 3 and 5 positions under the presence of a base such as NaH, and the compound represented by Chemical Formula 6 formed with three rings is synthesized by synthesizing an imidazole ring through reacting with 1,2-dichloroethyl ethyl ether or chloroacetaldehyde. The compound represented by Chemical Formula 7 is synthesized by introducing substituents of $R^1$ and $R^4$ through reacting the compound represented by Chemical Formula 6 with a material capable of functioning as a halogen donor such as $SO_2Cl_2$, and the compound represented by Chemical Formula 8 is synthesized by oxidizing the sulfide of the compound represented by Chemical Formula 7 using mCPBA or oxone.

[Reaction Formula 2]

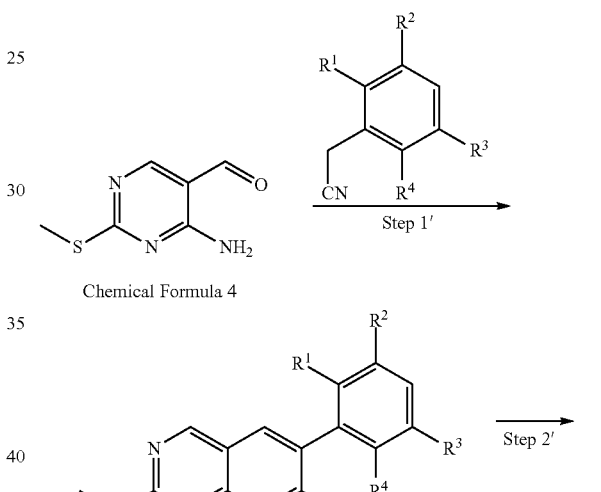

Chemical Formula 4

Step 1'

Chemical Formula 5'

Step 2'

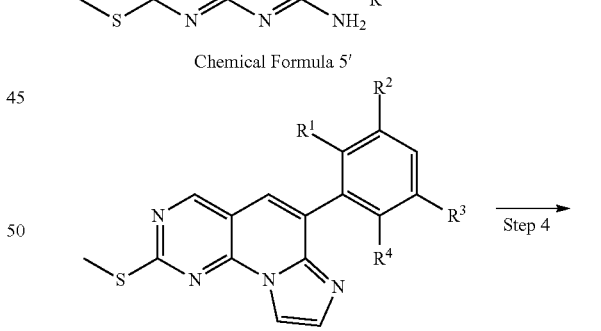

Chemical Formula 7

Step 4

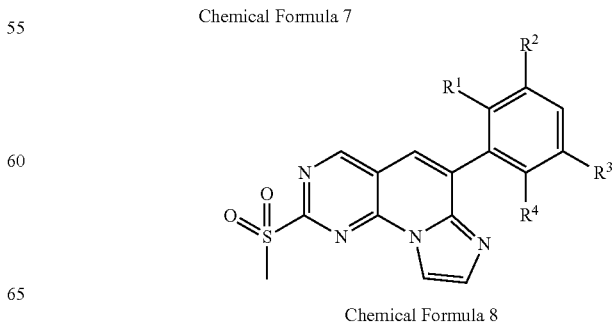

Chemical Formula 8

In Reaction Formula 2, the compound represented by Chemical Formula 5' is synthesized through a condensation reaction of the compound of Chemical Formula 4 and 2-phenylacetonitrile having 4 substituents at 2,3,4 and 5 positions under the presence of a base such as NaH, and the compound represented by Chemical Formula 7 formed with three rings is synthesized by synthesizing an imidazole ring through reacting with 1,2-dichloroethyl ethyl ether or chloroacetaldehyde. The compound represented by Chemical Formula 8 is synthesized by oxidizing the sulfide of the compound represented by Chemical Formula 7 using mCPBA or oxone.

[Reaction Formula 3]

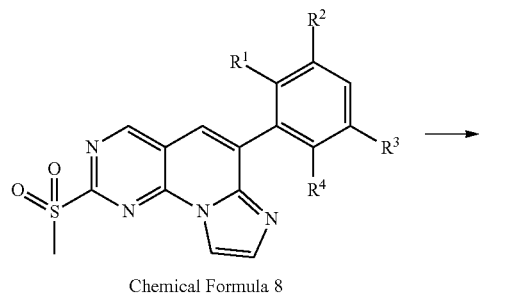

Chemical Formula 8

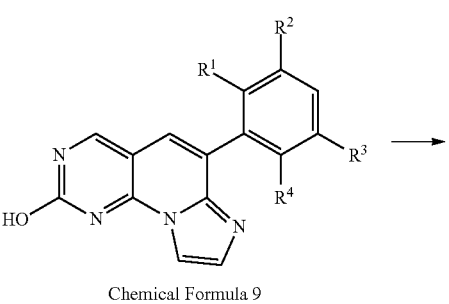

Chemical Formula 9

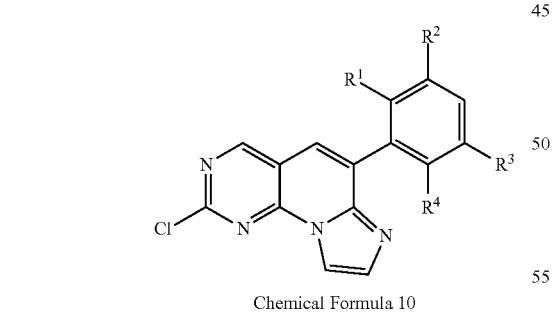

Chemical Formula 10

In Reaction Formula 3, the compound represented by Chemical Formula 9 is synthesized starting from the compound represented by Chemical Formula 8 by substituting the sulfonyl group with an OH group, and the compound of Chemical Formula 10 is synthesized by substituting the OH group with a chloro group through reacting the compound of Chemical Formula 9 with a material such as POCl₃, and is used for the next reaction.

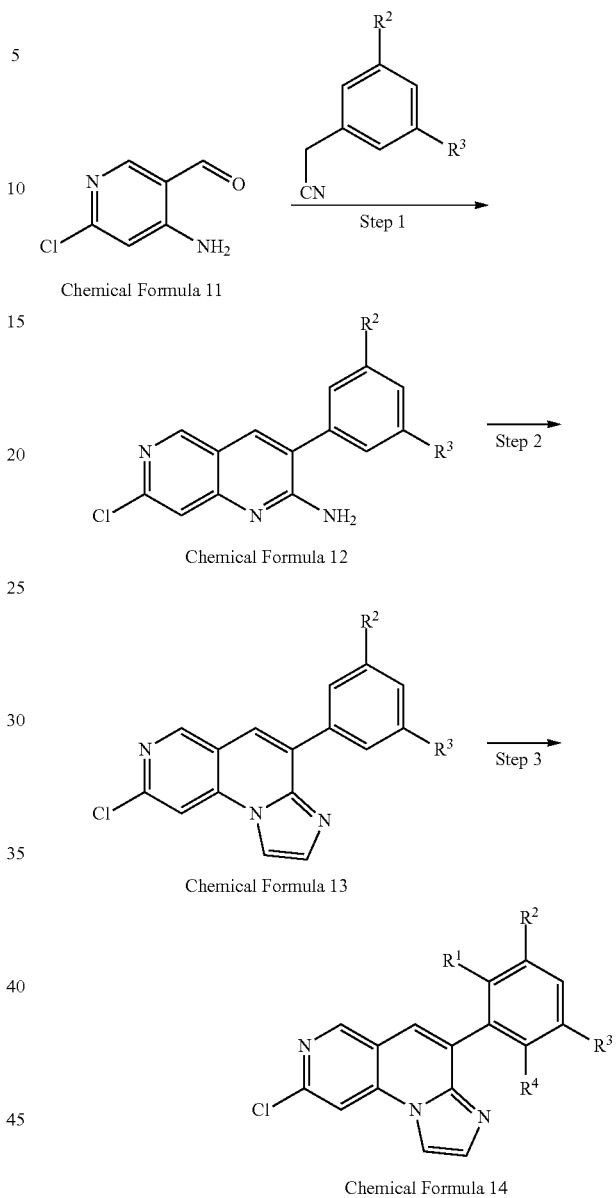

In Reaction Formula 4, $R^1$, $R^2$, $R^3$ and $R^4$ each have the same definition as in Chemical Formula 1.

In Reaction Formula 4, the compound represented by Chemical Formula 12 is synthesized through a condensation reaction of the compound of Chemical Formula 11 and 2-phenylacetonitrile having two substituents at 3 and 5 positions under the presence of a base such as NaH, and the compound represented by Chemical Formula 13 formed with three rings is synthesized by synthesizing an imidazole ring through reacting with 1,2-dichloroethyl ethyl ether or chloroacetaldehyde. The compound represented by Chemical Formula 14 is synthesized by introducing substituents of $R^1$ and $R^4$ through reacting the compound represented by Chemical Formula 13 with a material capable of functioning as a halogen donor such as $SO_2Cl_2$.

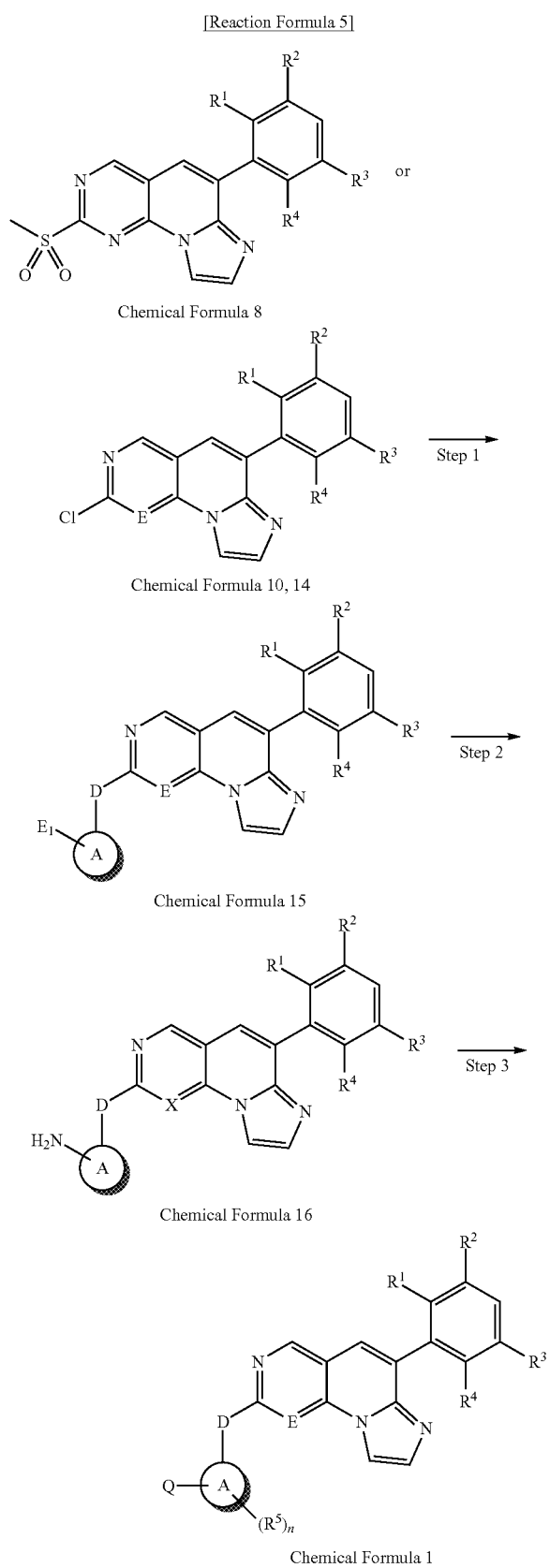

[Reaction Formula 5]

Chemical Formula 8

Chemical Formula 10, 14

Chemical Formula 15

Chemical Formula 16

Chemical Formula 1

In Reaction Formula 5, E1 is hygrogen, $NO_2$, $N_3$, NH-Boc; and

D, E, Q, $R^1$, $R^2$, $R^3$ and $R^4$ each have the same definition as in Chemical Formula 1.

In Reaction Formula 5, the compound represented by Chemical Formula 15 is synthesized through a reaction of the compounds represented by Chemical Formula 8, 9 and 14 with amine or aniline having a protected amine group under the presence of a base or a palladium catalyst, and the compound represented by Chemical Formula 16 is synthesized by deprotecting an amine protecting group under the presence of a reducing catalyst or an acid catalyst from the compound represented by Chemical Formula 15, and the compound represented by Chemical Formula 1 is synthsized by introducing an acryl group to the compound represented by Chemical Formula 16.

The compound according to the present invention may also form a pharmaceutically acceptable salt. Such a pharmaceutically acceptable salt is not particularly limited as long as it is an acid forming a nontoxic acid addition salt containing a pharmaceutically acceptable anion. Examples thereof may include an acid addition salt formed by an inorganic acid such as hydrochloric acid, sulfuric acid, nitric acid, phosphoric acid, hydrobromic acid and hydroiodic acid; an organic carboxylic acid such as tartaric acid, formic acid, citric acid, acetic acid, trichloroacetic acid, trifluoroacetic acid, gluconic acid, benzoic acid, lactic acid, fumaric acid and maleic acid; or a sulfonic acid such as methanesulfonic acid, benzenesulfonic acid, p-toluenesulfonic acid and naphthalenesulfonic acid.

Meanwhile, the compounds according to the present invention may have an asymmetric carbon center, and therefore, may be present as an R or S isomer, a racemic compound, a diastereomer mixture or an individual diastereomer, and all these isomers and mixtures are included in the scope of the present invention.

In addition thereto, solvate and hydrate forms of the indole compound of Chemical Formula 1 are also included in the scope of the present invention.

Another embodiment of the present invention provides a pharmaceutical composition containing the compound selected from the group consisting of the compounds of Chemical Formula 1 and a pharmaceutically acceptable salt thereof in a therapeutically effective amount.

In the pharmaceutical composition of the present invention, the compound represented by Chemical Formula 1 included therein inhibits fibroblast growth factor receptor (FGFR) activity, and as a result, the pharmaceutical composition is useful in preventing or treating various diseases relating to the FGFR.

According to another embodiment of the present invention, the pharmaceutical composition is a pharmaceutical composition for preventing or treating cancers or tumors, and specifically, the cancer may be selected from the group consisting of liver cancer, hepatocellular carcinoma, thyroid cancer, colorectal cancer, testicular cancer, bone cancer, oral cancer, basal cell carcinoma, ovarian cancer, brain tumor, gallbladder carcinoma, biliary tract cancer, head and neck cancer, colorectal cancer, vesical carcinoma, tongue cancer, esophageal cancer, glioma, glioblastoma, renal cancer, malignant melanoma, gastric cancer, breast cancer, sarcoma, pharynx carcinoma, uterine cancer, cervical cancer, prostate cancer, rectal cancer, pancreatic cancer, lung cancer, skin cancer and other solid cancers, but are not limited thereto.

Another embodiment of the present invention provides a pharmaceutical formulation including the pharmaceutical composition.

The pharmaceutical formulation of the present invention may have various oral administration forms such as tablets, pills, powders, capsules, syrups or emulsions, or parenteral administration forms such as intramuscular, intravenous or hypodermic injections, and preferably have oral administration forms.

In addition, the pharmaceutical formulation may be pharmaceutically prepared using common methods adding one or more members selected from the group consisting of, for example, carriers, adjuvants and vehicles as a common nontonxic pharmaceutically acceptable additive in addition to effective ingredients.

As the vehicle capable of being used in the pharmaceutical formulation of the present invention, a sweetening agent, a binding agent, a dissolvent, a dissolution aid, a humectant, an emulsifier, an isotonic agent, an adsorbent, a disintegrating agent, an antioxidant, an antiseptic, a glidant, a filler, a flavoring agent and the like may be included, however, the vehicle is not limited thereto. For example, lactose, dextrose, sucrose, mannitol, sorbitol, cellulose, glycine, silica, magnesium aluminum silicate, starch, gelatin, tragacanth rubber, alginic acid, sodium alginate, methyl cellulose, sodium carboxylmethyl cellulose, water, ethanol, polyethylene glycol, polyvinyl pyrrolidone, sodium chloride, potassium chloride, orange essence, strawberry essence, vanilla flavoring and the like may be used as the vehicle.

When the pharmaceutical formulation of the present invention has an oral administration form, examples of the carrier used may include cellulose, calcium silicate, corn starch, lactose, sucrose, dextrose, potassium phosphate, stearic acid, magnesium stearate, calcium stearate, gelatin, talc and the like, however, the carrier is not limited thereto.

When the pharmaceutical formulation of the present invention has an injection form, examples of the carrier may include water, a saline solution, an aqueous glucose solution, a similar aqueous sugar solution, alcohol, glycol, ether, oil, fatty acid, fatty acid ester, glyceride and the like, however, the carrier is not limited thereto.

In order to use the compound according to the present invention as drugs, the latter is prepared into a pharmaceutical formulation form, and this contains, in addition to active ingredients for oral or parenteral administration, suitable pharmaceutical organic or inorganic inactive carrier materials such as water, gelatin, arabia gum, lactose, starch, vegetable oil and polyalkylene glycol. The pharmaceutical formulation may be present in a solid form such as a tablet, a sugarcoated tablet, a suppositor or a capsule, or in a liquid form such as a liquid medicine, a suspension or an emulsion. In addition, these randomly contains an adjuvant such as an antiseptic, a stabilizer, a humectant or an emulsifier; a salt or a buffer for changing an osmotic pressure.

For parenteral administration, an injection liquid medicine or a suspension is particularly preferred.

As the carrier system, a surface activity aid such as cholate or animal or vegetable phospholipid, or a mixture thereof, and liposome or components thereof may also be used.

For oral administration, talc and/or hydrocarbon vehicle or binding agent, for example, tablets, sugarcoated tablets or capsules containing lactose, corn or potato starch are particularly suited. In addition, a liquid form, for example, a sweetening agent-added juice may be administered.

In addition, a dosage of the compound of Chemical Formula 1 according to the present invention for the human body is preferably in a range of 0.1 mg/day to 2,000 mg/day based on an adult patient with a 70 kg weight in general. The compound according to the present invention may be administered once to in several installments a day. However, the dosage may vary depending on health, age, weight and gender of a patient, and the type of administration and the degree of disease, and accordingly, the scope of the present invention is not limited to the dosage presented above.

Hereinafter, the present invention will be described in more detail with reference to the following preparation examples and examples, however, these are for illustrative purposes only, and the scope of the present invention is not limited thereto.

EXAMPLE

[Example 1] N-(2-((6-(2,6-dichloro-3,5-dimethoxyphenyl)imidazo[1',2':1,6]pyrido[2,3-d]pyrimidin-2-yl)amino)cyclopentyl)acrylamide [Compound 1]

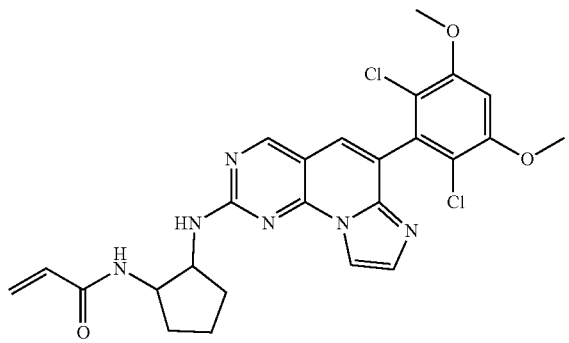 [SMILES: C=CC(=O)NC1CCCC1Nc1ncc2cc(-c3c(Cl)c(OC)cc(OC)c3Cl)c3nccn3c2n1]

Step 1. Preparation of 6-(3,5-dimethoxyphenyl)-2-(methylthio)pyrido[2,3-d]pyrimidine-7-amine

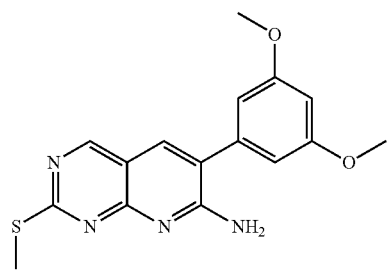 [SMILES: COc1cc(OC)cc(-c2cc3cnc(SC)nc3nc2N)c1]

To a solution of 3,5-dimethoxyphenylacetonitrile (2.89 g, 16.3 mmol) in tetrahydrofuran was added 60% NaH (720 mg, 17.9 mmol). The mixture was stirred at room temperature for 1 hour. 4-Amino-2-(methylsulfanyl)-5-pyrimidinecarbaldehyde (2.5 g, 14.8 mmol) was added, and then stirred for 6 hours. The mixture was concentrated under vacuum. The residue was dissolved in dichloromethane, washed with saturated ammonium chloride. Organic layer was dried over sodium sulfate, filtered and concentrated under vacuum to give a target compound (3.6 g) (J. Med. Chem. 2005, 48, 4628-4653).

Step 2. Preparation of 6-(3,5-dimethoxyphenyl)-2-(methylthio)imidazo[1',2':1,6]pyrido[2,3-d]pyrimidine

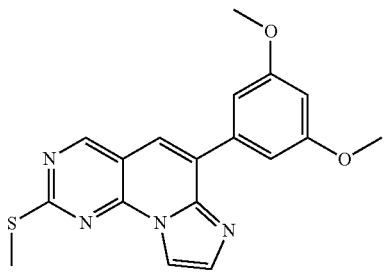 [SMILES: COc1cc(OC)cc(-c2cc3cnc(SC)nc3n3ccnc23)c1]

To a mixture of 6-(3,5-dimethoxyphenyl)-2-(methylthio)pyrido[2,3-d]pyrimidine-7-amine (2.59 g, 7.9 mmol) synthesized in [Step 1] and trimethylamine (6.6 ml, 47.6 mmol) in acetonitrile/water (1/1) was added 1,2-dichloroethyl ethyl ether (4 ml, 32 mmol) over 30 minutes. The mixture was stirred for overnight, and then refluxed for 4 hours. After cooling to room temperature, water was added. The precipitate was filtered to obtain a target compound (1.67 g).

Step 3. Preparation of 6-(2,6-dichloro-3,5-dimethoxyphenyl)-2-(methylthio)imidazo[1',2':1,6]pyrido[2,3-d]pyrimidine

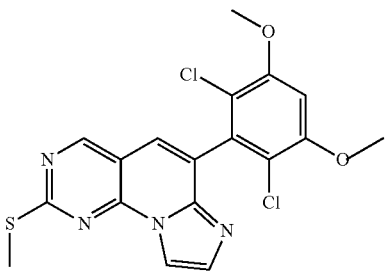

The 6-(3,5-dimethoxyphenyl)-2-(methylthio)imidazo[1',2':1,6]pyrido[2,3-d]pyrimidine compound (1.5 g, 4.25 mmol) synthesized in [Step 2] was dissolved in dichloromethane. Sulfuryl chloride (SO$_2$Cl$_2$, 1.14 g, 8.5 mmol) was added dropwise at −20 □., and then stirred for 30 minutes. When the reaction was completed, a small quantity of methanol was added thereto, and the reaction mixture was concentrated under vacuum. The residue was triturated in ethyl acetate for 30 minutes and then filtered to obtain a target compound (1.3 g).

Step 4. Preparation of 6-(2,6-dichloro-3,5-dimethoxyphenyl)-2-(methylsulfonyl)imidazo[1',2':1,6]pyrido[2,3-d]pyrimidine

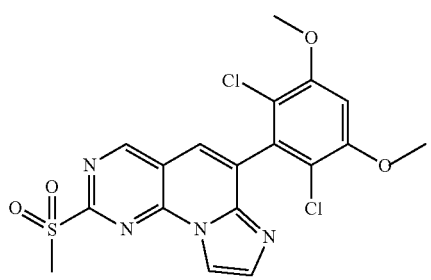

To a solution of 6-(2,6-dichloro-3,5-dimethoxyphenyl)-2-(methylsulfonyl)imidazo[1',2':1,6]pyrido[2,3-d]pyrimidine (1.2 g, 2.85 mmol) synthesized in [Step 3] in dichloromethane was added m-chloroperbenzoic acid (1.14 g, 8.5 mmol), and the mixture was reacted for 6 hours. When the reaction was completed, the solvent was concentrated under vacuum. The residue was titrated in ethyl acetate for 30 minutes and then filtered to obtain a target compound (1.0 g).

Step 5. Preparation of t-butyl(2-((6-(2,6-dichloro-3,5-dimethoxyphenyl)imidazo[1',2':1,6]pyrido[2,3-d]pyrimidin-2-yl)amino)cyclopentyl)carbamate

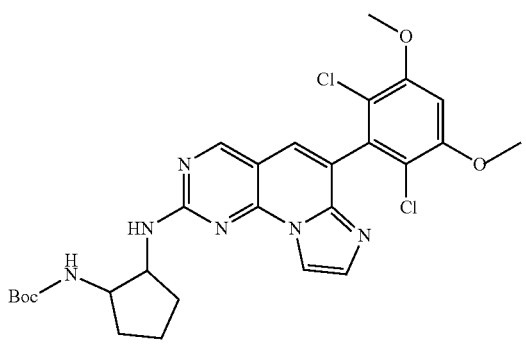

The 6-(2,6-dichloro-3,5-dimethoxyphenyl)-2-(methylsulfonyl)imidazo[1',2':1,6]pyrido[2,3-d]pyrimidine (200 mg, 0.44 mmol) synthesized in [Step 4] and (±)cis-t-butyl(2-aminocyclopentyl)carbamate (17 mg, 0.85 mmol) were added into N,N-dimethylformamide. The mixture was stirred at 100 □ for 30 minutes. After cooling to room temperature, water was added. The precipitate was filtered to obtain a target compound (100 mg). The next step was progressed without purification.

Step 6. Preparation of N$^1$-(6-(2,6-dichloro-3,5-dimethoxyphenyl)imidazo[1',2':1,6]pyrido[2,3-d]pyrimidin-2-yl)cyclopentane-1,2-diamine

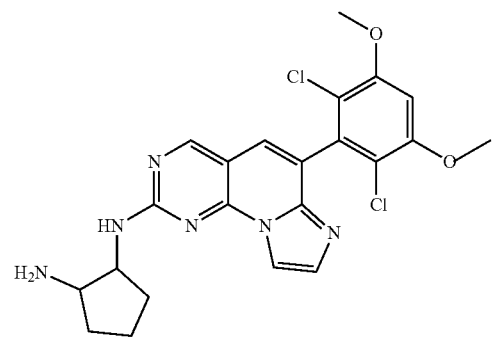

The t-butyl(2-((6-(2,6-dichloro-3,5-dimethoxyphenyl)imidazo[1',2':1,6]pyrido[2,3-d]pyrimidin-2-yl)amino)cyclopentyl)carbamate (100 mg, 0.17 mmol) synthesized in [Step 5] was dissolved in dichloromethane. Trifluoroacetic acid (1 ml) was added thereto, and the mixture was stirred for 2 hours at room temperature. The mixture was concentrated under vacuum, and the next step was progressed without purification.

Step 7. Preparation of N-(2-((6-(2,6-dichloro-3,5-dimethoxyphenyl)imidazo[1',2':1,6]pyrido[2,3-d]pyrimidin-2-yl)amino)cyclopentyl)acrylamide

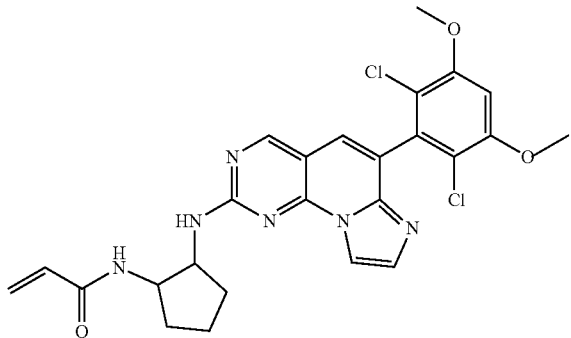

To a solution of $N^1$-(6-(2,6-dichloro-3,5-dimethoxyphenyl)imidazo[1',2':1,6]pyrido[2,3-d]pyrimidin-2-yl)cyclopentane-1,2-diamine (40 mg, 0.16 mmol) synthesized in [Step 6] in tetrahydrofuran/water (4/1) was added sodium bicarbonate (42 mg, 0.5 mmol) at 0 □. Acryloyl chloride (22 mg, 0.24 mmol) was added, and the mixture was stirred for 1 hour. The mixture was concentrated under vacuum, and extracted with a mixed solvent of chloroform/isopropyl alcohol (4/1). The organic layer was dried over sodium sulfate, and concentrated under vacuum. The crude material was purified by Chromatography to give the target compound (30 mg) as solid.

| # | Structure 1H NMR spectrum (300 MHz) | Name | MS [M + H]+ |
|---|---|---|---|
| 1 | | N-(2-(((6-(2,6-dichloro-3,5-dimethoxyphenyl)imidazo[1',2':1,6]pyrido[2,3-d]pyrimidin-2-yl)amino)cyclopentyl)acrylamide | 527.1 |
| 2 | | N-(2-(((6-(2,6-dichloro-3,5-dimethoxyphenyl)imidazo[1',2':1,6]pyrido[2,3-d]pyrimidin-2-yl)amino)cyclohexyl)acrylamide | 541.1 |

| # | Structure 1H NMR spectrum (300 MHz) | Name | MS [M + H]+ |
|---|---|---|---|
| 3 | (CDCl3) δ 8.84 (s, 1H), 8.24 (s, 1H), 7.59 (s, 1H), 7.24 (s, 1H), 6.69 (s, 1H), 6.16 (m, 2H), 5.51 (m, 1H), 4.94 (brs, 1H), 4.61 (brs, 1H), 4.28 (brs, 1H), 4.16 (m, 1H), 3.95 (s, 6H), 3.81 (m, 1H) | N-(4-((6-(2,6-dichloro-3,5-dimethoxyphenyl)imidazo[1',2':1,6]pyrido[2,3-d]pyrimidin-2-yl)amino)tetrahydrofuran-3-yl)acrylamide | 529.1 |

[Example 4] N-((3S,4S)-3-((6-(2,6-dichloro-3,5-dimethoxyphenyl)imidazo[1',2':1,6]pyrido[2,3-d]pyrimidin-2-yl)amino)tetrahydro-2H-pyran-4-yl)acrylamide [Compound 4]

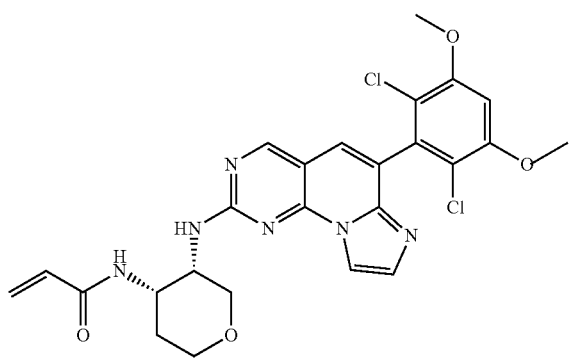

Step 1. Preparation of N-((3S,4S)-4-azidotetrahydro-2H-pyran-3-yl)-6-(2,6-dichloro-3,5-dimethoxyphenyl)imidazo[1',2':1,6]pyrido[2,3-d]pyrimidine-2-amine

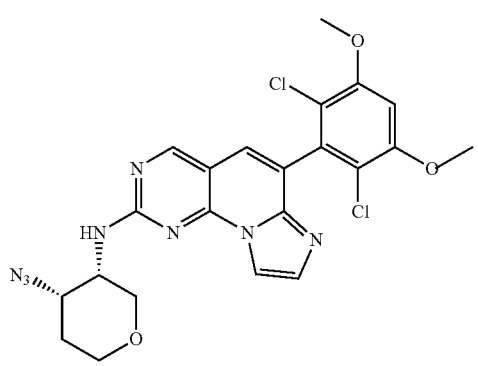

The 6-(2,6-dichloro-3,5-dimethoxyphenyl)-2-(methylsulfonyl)imidazo[1',2':1,6]pyrido[2,3-d]pyrimidine (170 mg, 0.375 mmol) synthesized in [Step 4] of [Example 1], (3S,4S)-4-azidotetrahydro-2H-pyran-3-amine hydrochloride (87 mg, 0.487 mmol) were taken up in N-methylpyrrolidine and sodium bicarbonate (95 mg, 1.125 mmol) were added. The mixture was heated to 100 □, and stirred for 4 hours. After cooling to room temperature, water was added. The mixture was extracted with ethyl acetate. The organic layer was dried over sodium sulfate, filtered and concentrated under vacuum. The crude material was purified by Chromatography to give the target compound (60 mg) as solid.

Step 2. Preparation of (3S,4S)—N³-(6-(2,6-dichloro-3,5-dimethoxyphenyl)imidazo[1',2':1,6]pyrido[2,3-d]pyrimidin-2-yl)tetrahydro-2H-pyran-3,4-diamine

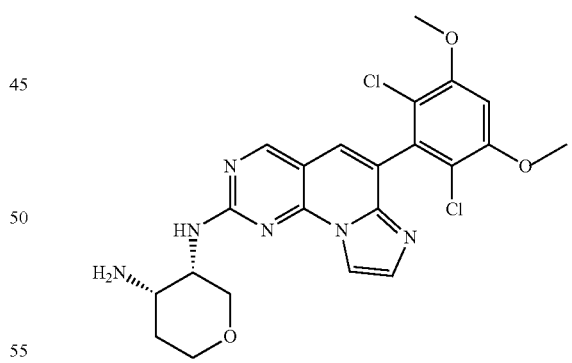

The N-((3S,4S)-4-azidotetrahydro-2H-pyran-3-yl)-6-(2,6-dichloro-3,5-dimethoxyphenyl)imidazo[1',2':1,6]pyrido[2,3-d]pyrimidine-2-amine (60 mg, 0.11 mmol) synthesized in [Step 1] was dissolved in tetrahydrofuran/methanol (1/1). Excess Raney Ni was added, and the mixture was stirred for 2 hours under a hydrogen balloon condition. The mixture was filtered using a celite, and a residue was concentrated under vacuum. The crude material was purified by Chromatography to give the target compound (25 mg) as solid.

Step 3. Preparation of N-((3S,4S)-3-((6-(2,6-dichloro-3,5-dimethoxyphenyl)imidazo[1',2':1,6]pyrido[2,3-d]pyrimidin-2-yl)amino)tetrahydro-2H-pyran-4-yl)acrylamide

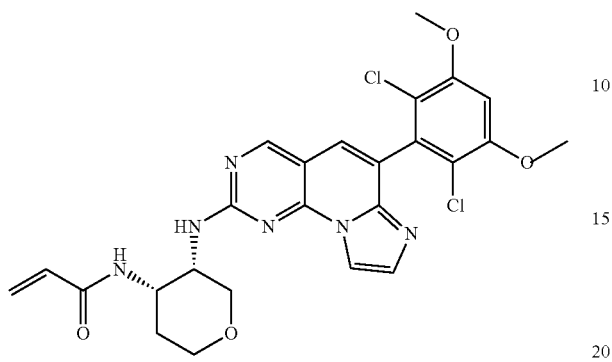

A target compound (69 mg) was obtained by the synthesis method of [Step 7] of [Example 1] using the (3S,4S)—N³-(6-(2,6-dichloro-3,5-dimethoxyphenyl)imidazo[1',2':1,6]pyrido[2,3-d]pyrimidin-2-yl)tetrahydro-2H-pyran-3,4-diamine (120 mg, 0.245 mmol) synthesized in [Step 2].

| 4 | 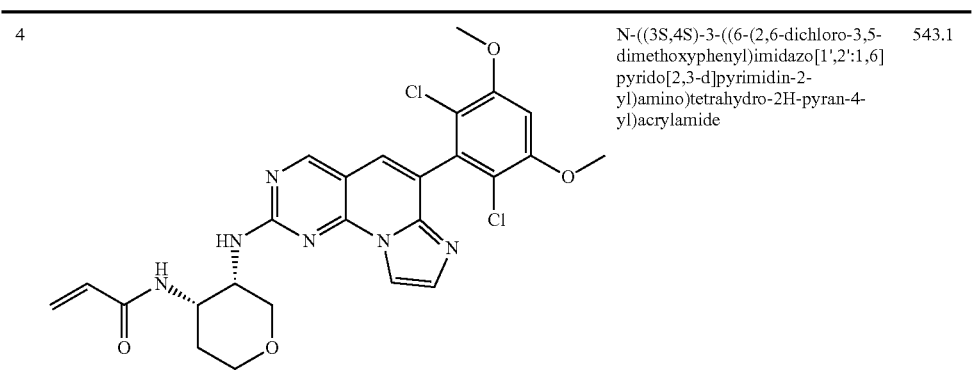 | N-((3S,4S)-3-((6-(2,6-dichloro-3,5-dimethoxyphenyl)imidazo[1',2':1,6]pyrido[2,3-d]pyrimidin-2-yl)amino)tetrahydro-2H-pyran-4-yl)acrylamide | 543.1 |
|---|---|---|---|
| | (DMSO-$d_6$) δ 9.01 (s, 1H), 8.28 (s, 1H), 8.03-8.00 (d, 1H), 7.69-7.66 (d, 1H), 7.47 (brs, 1H), 7.43 (s, 1H), 7.05 (s, 1H), 6.13-5.91 (m, 2H), 5.35-5.32 (d, 1H), 4.58 (m, 1H), 4.30 (m, 1H), 3.98 (s, 6H), 3.93-3.90 (m, 2H), 3.71-3.52 (m, 2H), 2.01-1.94 (m, 1H), 1.68-1.65 (m, 1H) | | |
| 5 | 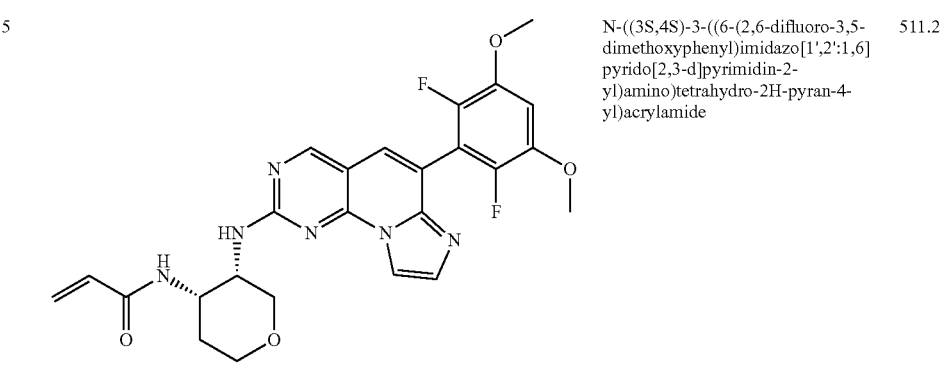 | N-((3S,4S)-3-((6-(2,6-difluoro-3,5-dimethoxyphenyl)imidazo[1',2':1,6]pyrido[2,3-d]pyrimidin-2-yl)amino)tetrahydro-2H-pyran-4-yl)acrylamide | 511.2 |
| | (DMSO-$d_6$) δ 9.01 (s, 1H), 8.30 (s, 1H), 8.06 (d, 1H), 7.77 (d, 1H), 7.61 (s, 1H), 7.53 (s, 1H), 6.10 (m, 2H), 5.79 (t, 1H), 4.24 (m, 2H), 3.92 (s, 6H), 3.82 (m, 2H), 1.97 (m, 2H), 1.89 (m, 2H) | | |

[Example 6] N-(2-((6-(2,6-dichloro-3,5-dimethoxyphenyl)imidazo[1',2':1,6]pyrido[2,3-d]pyrimidin-2-yl)amino)phenyl)acrylamide [Compound 6]

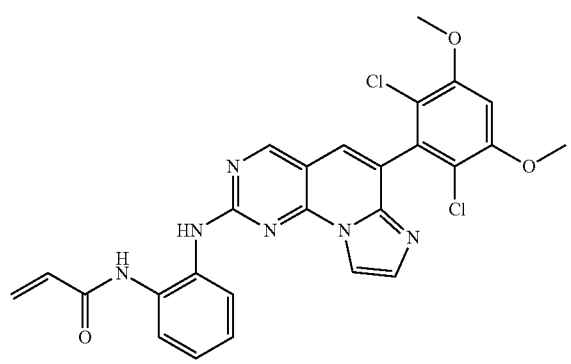 [SMILES: C=CC(=O)Nc1ccccc1Nc1ncc2cc(-c3c(Cl)c(OC)cc(OC)c3Cl)c3nccn3c2n1]

Step 1. Preparation of 6-(2,6-dichloro-3,5-dimethoxyphenyl)-N-(2-nitrophenyl)imidazo[1',2':1,6]pyrido[2,3-d]pyrimidine-2-amine

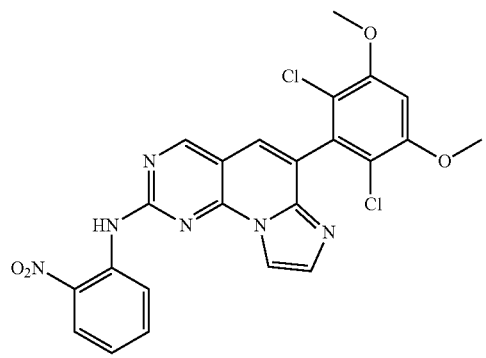

The 6-(2,6-dichloro-3,5-dimethoxyphenyl)-2-(methylsulfonyl)imidazo[1',2':1,6]pyrido[2,3-d]pyrimidine (150 mg, 0.33 mmol) synthesized in [Step 4] of [Example 1] and 2-nitroaniline (68 mg, 0.66 mmol) were taken up in N,N-dimethylformamide. Potassium t-butoxide (110 mg, 0.99 mmol) was added, and the mixture was stirred for 30 minutes. After cooling to room temperature, water was added, and the precipitate was filtered to obtain a target compound (120 mg).

Step 2. Preparation of N1-(6-(2,6-dichloro-3,5-dimethoxyphenyl)imidazo[1',2':1,6]pyrido[2,3-d]pyrimidin-2-yl)benzene-1,2-diamine

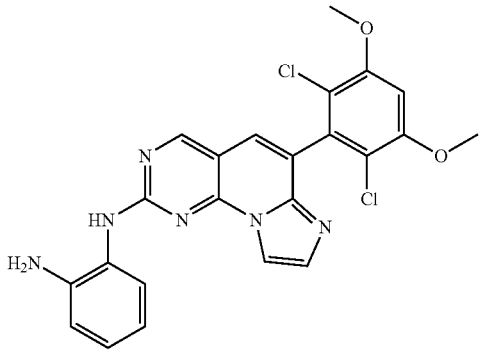 [SMILES: COc1cc(OC)c(Cl)c(-c2cc3cnc(Nc4ccccc4[N+](=O)[O-])nc3n3ccnc23)c1Cl]

A target compound (84 mg) was obtained by the synthesis method of [Step 6] of [Example 1] using the 6-(2,6-dichloro-3,5-dimethoxyphenyl)-N-(2-methoxy-6-nitro-4-(pyrrolidin-1-yl)phenyl)imidazo[1',2':1,6]pyrido[2,3-d]pyrimidine-2-amine (120 g, 0.23 mmol) synthesized in [Step 1].

Step 3. Preparation of N-(2-((6-(2,6-dichloro-3,5-dimethoxyphenyl)imidazo[1',2':1,6]pyrido[2,3-d]pyrimidin-2-yl)amino)phenyl)acrylamide

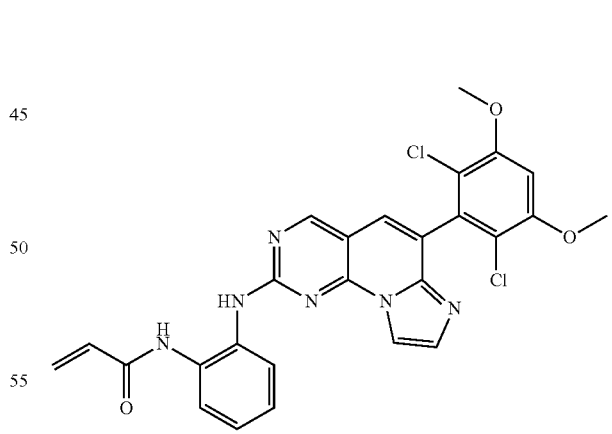

A target compound (13 mg) was obtained by the synthesis method of [Step 7] of [Example 1] using the N1-(6-(2,6-dichloro-3,5-dimethoxyphenyl)imidazo[1',2':1,6]pyrido[2,3-d]pyrimidin-2-yl)benzene-1,2-diamine (84 mg, 0.18 mmol) synthesized in [Step 2].

| 6 | 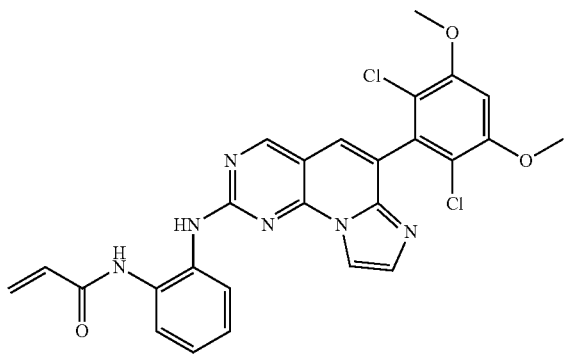 [SMILES: C=CC(=O)Nc1ccccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)phenyl)acrylamide | 535.1 |

(CDCl₃) δ 8.89 (s, 1H), 8.47 (s, 1H), 8.20 (s, 1H), 8.09 (s, 1H), 7.82 (s, 1H), 7.71 d, 1H), 7.51 (s, 1H), 7.24 (m 3H), 6.62 (s, 1H), 6.32 (dd, 1H), 6.12 (m, 1H), 5.63 (dd, 1H), 3.92 (s, 6H)

| 7 | 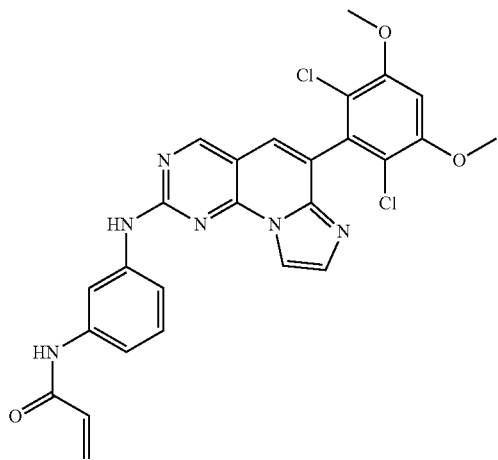 [SMILES: C=CC(=O)Nc1cccc(Nc2ncc3cc(-c4c(Cl)c(OC)cc(OC)c4Cl)c4nccn4c3n2)c1] | N-(3-((6-(2,6-dichloro-3,5-dimethoxyphenyl)imidazo[1',2':1,6]pyrido[2,3-d]pyrimidin-2-yl)amino)phenyl)acrylamide | 535.1 |

(CDCl₃) δ 8.93 (s, 1H), 8.62 (m, 2H), 8.22 (m, 1H), 7.77 (s, 1H), 7.66 (s, 1H), 7.27 (m, 4H), 7.15 (m, 1H), 6.44 (m, 2H), 5.73 (m, 1H), 3.89 (s, 6H)

| 8 | 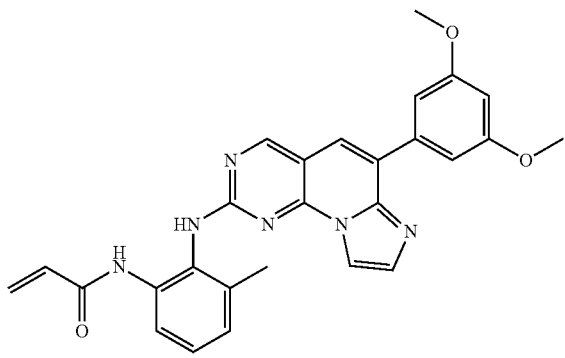 [SMILES: C=CC(=O)Nc1cccc(C)c1Nc1ncc2cc(-c3cc(OC)cc(OC)c3)c3nccn3c2n1] | N-(2-((6-(3,5-dimethoxyphenyl)imidazo[1',2':1,6]pyrido[2,3-d]pyrimidin-2-yl)amino)-3-methylphenyl)acrylamide | 481.2 |

(CD₃OD) δ 8.88 (s, 1H), 8.10 (br, 1H), 7.55 (s, H), 7.52 (m, 2H) 7.50 (br, 1 H), 7.17 (m, 2H) 6.91 (m, 2H), 6.45 (m, 2H) 6.25 (m, 2H), 5.56 (d, 1H) 3.74 (s, 6H), 2.22 (s, 3H)

-continued

| 9 | 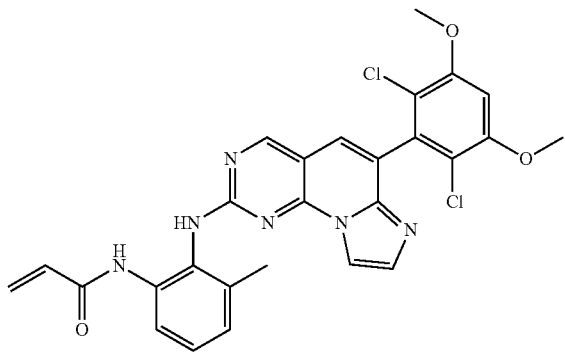 [SMILES: C=CC(=O)Nc1cccc(C)c1Nc1ncc2cc(-c3c(Cl)c(OC)cc(OC)c3Cl)c3nccn3c2n1] | N-(2-((6-(2,6-dichloro-3,5-dimethoxyphenyl)imido[1',2':1,6]pyrido[2,3-d]pyrimidin-2-yl)amino)-3-methylphenyl)acrylamide | 549.2 |

(CDCl$_3$) δ 9.07 (s, 1H), 7.75 (brs, 2H), 7.51 (s, 1H), 7.26 (m, 3H) 6.91 (s, 1H), 3.38 (m, 2H), 5.67 (d, 1H) 4.13 (s, 6H), 2.36 (s, 3H)

| 10 | 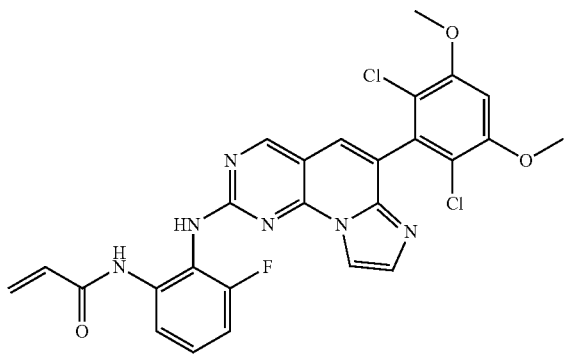 | N-(2-((6-(2,6-dichloro-3,5-dimethoxyphenyl)imidazo[1',2':1,6]pyrido[2,3-d]pyrimidin-2-yl)amino)-3-fluorophenyl)acrylamide | 553.1 |

(DMSO-d$_6$) δ 9.57 (s, 1H), 8.07 (d, 1H), 7.83-7.81 (m, 1H), 7.49-7.48 (m, 2H), 7.33-7.28 (m, 1H), 7.14-7.04 (m, 1H), 7.04 (s, 1H), 6.59-6.50 (m, 1H), 6.24-6.18 (m, 1H), 5.70-5.62 (m, 1H), 3.96 (s, 6H)

| 11 | 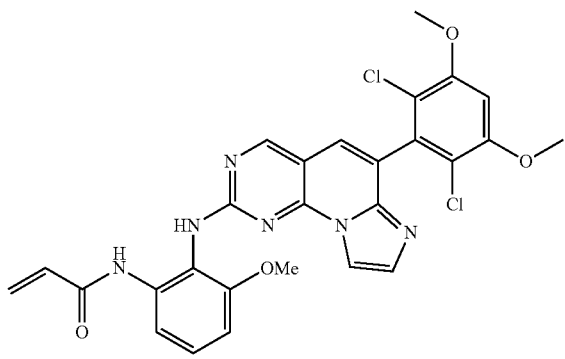 [SMILES: C=CC(=O)Nc1cccc(OC)c1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-3-methoxyphenyl)acrylamide | 565.1 |

(CDCl$_3$) δ 8.92 (s, 1H), 8.71 (s, 1H), 8.12 (s, 1H), 7.79 (s, 1H), 7.55 (t, 1H), 7.28 (m, 2H), 6.78 (d, 1H), 6.66 (s, 1H), 6.32 (dd, 1H), 6.12 (m, 1H), 5.63 (dd, 1H), 3.94 (s, 6H), 3.84 (s, 3H)

| 12 | 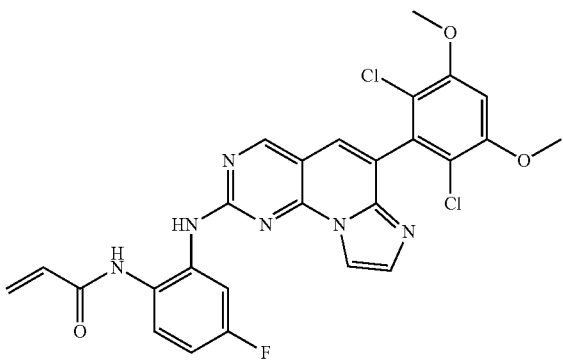 [SMILES: C=CC(=O)Nc1ccc(F)cc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-4-fluorophenyl)acrylamide | 553.1 |

(DMSO-d$_6$) δ 9.82 (brs, 1H), 9.71 (brs, 1H), 9.03 (s, 1H), 8.37 (s, 1H), 7.83 (m, 1H), 7.54 (m, 3H), 6.52 (m, 1H), 6.20 (m, 1H), 5.71 (m, 1H)

| 13 | 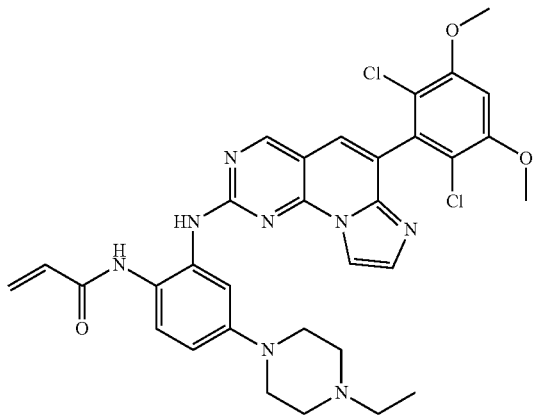 [SMILES: C=CC(=O)Nc1ccc(N2CCN(CC)CC2)cc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-4-(4-ethylpiperazin-1-yl)phenyl)acrylamide | 647.2 |

(DMSO-d$_6$) δ 9.76 (brs, 1H), 9.40 (brs, 1H), 9.16 (s, 1H), 8.12 (s, 1H), 7.57-7.51 (m, 3H), 7.41-7.38 (d, 1H), 7.06 (s, 1H), 6.86-6.82 (dd, 1H), 6.51-6.42 (m, 1H), 6.25-6.20 (d, 1H), 5.72-5.68 (d, 1H), 3.99 (s, 6H), 3.19 (t, 4H), 2.50 (t, 4H), 2.40-2.33 (q, 2H), 1.05-1.01 (t, 3H)

| 14 | 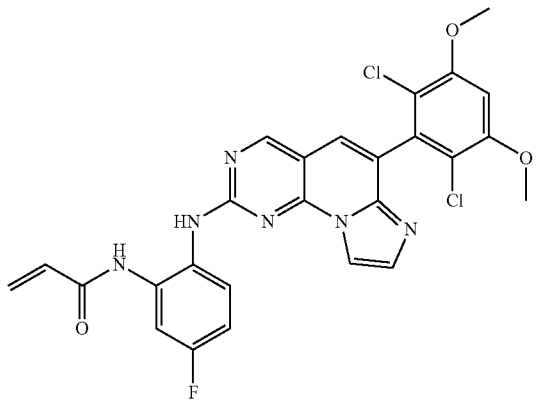 [SMILES: C=CC(=O)Nc1cc(F)ccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-fluorophenyl)acrylamide | 553.1 |

(DMSO-d$_6$) δ 9.74 (brs, 1H), 9.55 (brs, 1H), 9.13 (s, 1H), 8.12 (s, 1H), 7.80-7.69 (m, 2H), 7.52-7.50 (m, 2H), 7.12-7.06 (m, 2H), 6.56-6.47 (m, 1H), 6.26-6.20 (dd, 1H), 5.73-5.69 (dd, 1H), 3.99 (s, 6H)

| 15 | 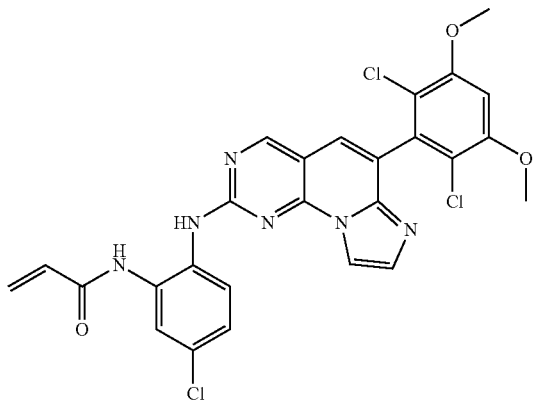 [SMILES: C=CC(=O)Nc1cc(Cl)ccc1Nc1ncc2cc(-c3c(Cl)c(OC)cc(OC)c3Cl)c3nccn3c2n1] | N-(5-chloro-2-((6-(2,6-dichloro-3,5-dimethoxyphenyl)imidazo[1',2':1,6]pyrido[2,3-d]pyrimidin-2-yl)amino)phenyl)acrylamide | 569.1 |

(DMSO-d$_6$) δ 9.77 (brs, 1H), 9.12 (s, 1H), 8.16 (s, 1H), 7.92 (d, 1H), 7.85-7.83 (d, 1H), 7.54-7.51 (m, 2H), 7.33-7.29 (dd, 1H), 7.06 (s, 1H), 6.55-6.46 (m, 1H), 6.26-6.20 (d, 1H), 5.76-5.69 (dd, 1H), 3.99 (s, 6H)

| 16 | 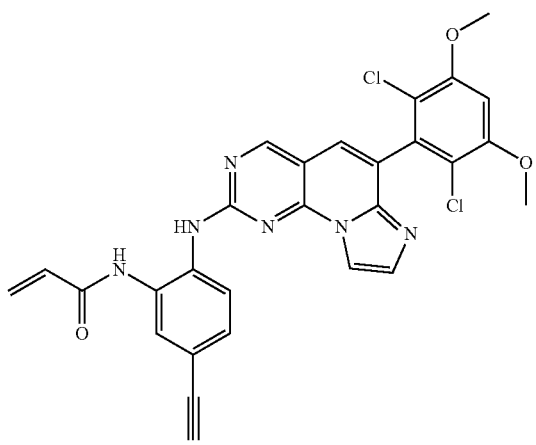 [SMILES: C#Cc1ccc(Nc2ncc3cc(-c4c(Cl)c(OC)cc(OC)c4Cl)c4nccn4c3n2)c(NC(=O)C=C)c1] | N-(2-((6-(2,6-dichloro-3,5-dimethoxyphenyl)imidazo[1',2':1,6]pyrido[2,3-d]pyrimidin-2-yl)amino)-5-ethynylphenyl)acrylamide | 559.1 |

(DMSO-d$_6$) δ 9.93 (m, 2H), 9.27 (s, 1H), 8.30 (s, 1H), 7.93-7.90 (d, 1H), 7.83-7.79 (m, 3H), 7.41-7.38 (dd, 1H), 7.11 (s, 1H), 6.50-6.44 (m, 1H), 6.25-6.19 (d, 1H), 5.73-5.69 (d, 1H), 4.21 (s, 1H), 4.00 (s, 6H)

| 17 | 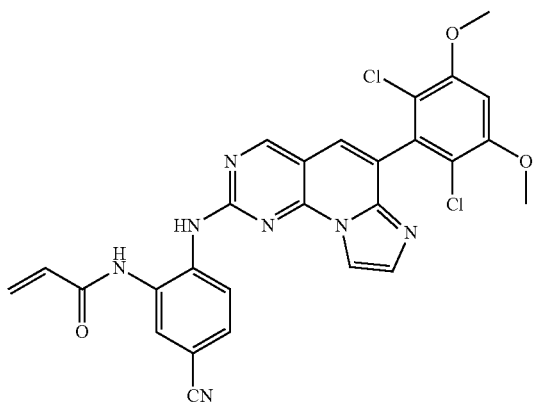 [SMILES: C=CC(=O)Nc1cc(C#N)ccc1Nc1ncc2cc(-c3c(Cl)c(OC)cc(OC)c3Cl)c3nccn3c2n1] | N-(5-cyano-2-((6-(2,6-dichloro-3,5-dimethoxyphenyl)imidazo[1',2':1,6]pyrido[2,3-d]pyrimidin-2-yl)amino)phenyl)acrylamide | 560.1 |

(DMSO-d$_6$) δ 9.96 (brs, 2H), 9.22 (s, 1H), 8.28-8.25 (m, 2H), 8.18 (s, 1H), 7.71-7.68 (d, 1H), 7.57-7.55 (m, 2H), 7.07 (s, 1H), 6.56-6.47 (m, 1H), 6.29-6.24 (dd, 1H), 5.78-5.75 (d, 1H), 3.99 (s, 6H)

| | | | |
|---|---|---|---|
| 18 | 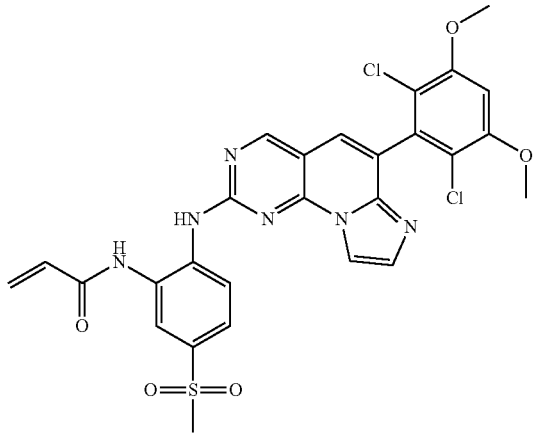 [SMILES: C=CC(=O)Nc1cc(S(C)(=O)=O)ccc1Nc1ncc2cc(-c3c(Cl)c(OC)cc(OC)c3Cl)c3nccn3c2n1]<br>(DMSO-d$_6$) δ 10.0 (brs, 2H), 9.23 (s, 1H), 8.33-8.28 (m, 3H), 7.83-7.80 (dd, 1H), 7.58-7.55 (m, 2H), 7.07 (s, 1H), 6.60-6.49 (m, 1H), 6.32-6.26 (d, 1H), 5.80-5.75 (dd, 1H), 3.99 (s, 6H), 3.24 (s, 3H) | N-(2-((6-(2,6-dichloro-3,5-dimethoxyphenyl)imidazo[1',2':1,6]pyrido[2,3-d]pyrimidin-2-yl)amino)-5-(methylsulfonyl)phenyl)acrylamide | 613.1 |
| 19 | 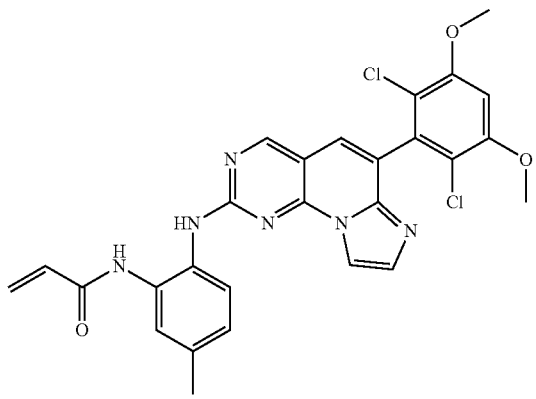 [SMILES: C=CC(=O)Nc1cc(C)ccc1Nc1ncc2cc(-c3c(Cl)c(OC)cc(OC)c3Cl)c3nccn3c2n1]<br>(DMSO-d$_6$) δ 9.75 (brs, 1H), 9.42 (brs, 1H), 9.12 (s, 1H), 8.13 (s, 1H), 7.72-7.69 (d, 1H), 7.51-7.50 (m, 3H), 7.11-7.06 (m, 2H), 6.54-6.45 (m, 1H), 6.26-6.19 (dd, 1H), 5.72-5.68 (dd, 1H), 3.99 (s, 6H), 2.34 (s, 3H) | N-(2-((6-(2,6-dichloro-3,5-dimethoxyphenyl)imidazo[1',2':1,6]pyrido[2,3-d]pyrimidin-2-yl)amino)-5-methylphenyl)acrylamide | 549.1 |
| 20 | 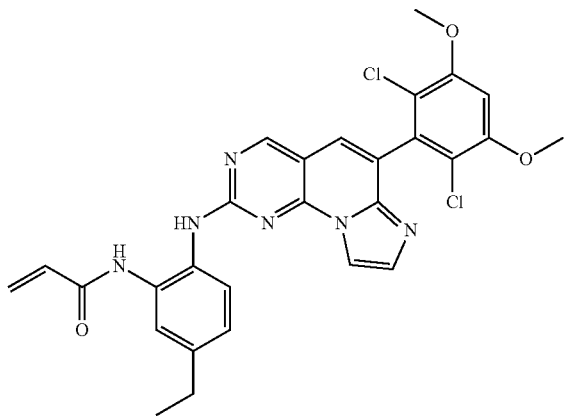 [SMILES: C=CC(=O)Nc1cc(CC)ccc1Nc1ncc2cc(-c3c(Cl)c(OC)cc(OC)c3Cl)c3nccn3c2n1]<br>(CDCl$_3$) δ 8.87 (s, 1H), 8.51 (s, 1H), 8.05 (s, 1H), 7.61 (s, 1H), 7.43 (s, 1H), 7.22 (s, 1H), 7.11 (d, 1H), 6.63 (s, 1H), 6.35 (m, 2H), 5.67 (m, 1H), 3.91 (s, 6H), 2.67 (q, 2H), 1.27 (t, 3H) | N-(2-((6-(2,6-dichloro-3,5-dimethoxyphenyl)imidazo[1',2':1,6]pyrido[2,3-d]pyrimidin-2-yl)amino)-5-ethylphenyl)acrylamide | 563.1 |

| | | | |
|---|---|---|---|
| 21 | 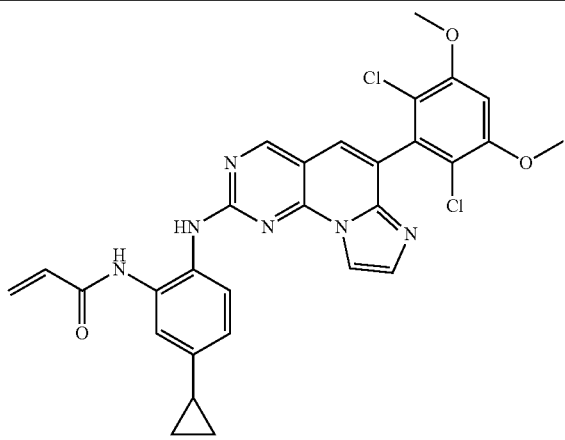 (CDCl₃) δ 8.88 (s, 1H), 8.44 (s, 1H), 8.05 (s, 1H), 7.96 (s, 1H), 7.56 (brs, 2H), 7.47 (s, 1H), 6.97 (d, 1H), 6.45 (s, 1H), 6.30 (d, 1H), 6.23 (m, 1H), 5.60 (d, 1H), 3.94 (s, 6H), 1.93 (m, 1H), 1.00 (m, 2H), 0.74 (m, 2H) | N-(5-cyclopropyl-2-((6-(2,6-dichloro-dimethoxyphenyl)imidazo[1',2':1,6]pyrido[2,3-d]pyrimidin-2-yl)amino)phenyl)acrylamide | 575.1 |
| 22 | 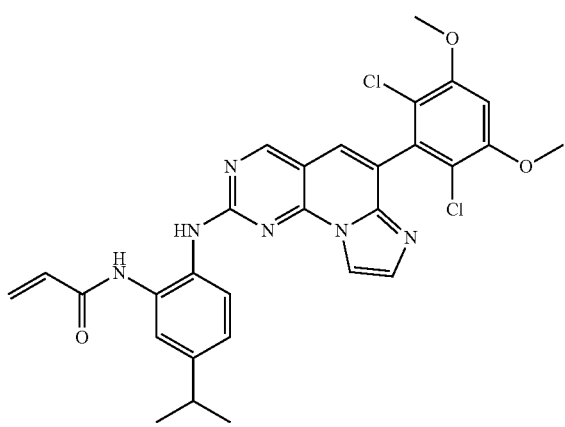 [SMILES: C=CC(=O)Nc1cc(C(C)C)ccc1Nc1ncc2cc(-c3c(Cl)c(OC)cc(OC)c3Cl)c3nccn3c2n1] (CDCl₃) δ 8.89 (s, 1H), 8.35 (s, 1H), 8.10 (s, 1H), 7.94 (s, 1H), 7.67 (s, 1H), 7.63 (s, 1H), 7.50 (s, 1H), 7.165 (dd, 1), 6.66 (s, 1H), 6.45 (m, 1H), 6.32 (m, 1H), 5.72 (dd, 1H), 3.94 (s, 6H), 2.95 (m, 1H), 1.29 (d, 6H) | N-(2-((6-(2,6-dichloro-3,5-dimethoxyphenyl)imidazo[1',2':1,6]pyrido[2,3-d]pyrimidin-2-yl)amino)-5-isopropylphenyl)acrylamide | 577.2 |
| 23 | 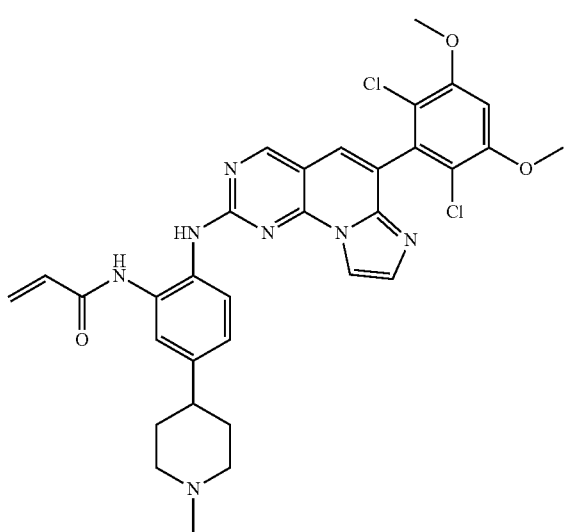 [SMILES: C=CC(=O)Nc1cc(C2CCN(C)CC2)ccc1Nc1ncc2cc(-c3c(Cl)c(OC)cc(OC)c3Cl)c3nccn3c2n1] (CDCl₃) δ 8.90 (s, 1H), 8.18 (s, 1H), 8.07 (m, 2H), 7.72 (m, 1H), 7.68 (m, 1H), 7.56 (m, 1H), 6.68 (s, 1H), 6.45 (d, 1H), 6.25 (d, 1H), 5.76 (d, 1H), 3.96 (s, 6H), 2.98 (m, 2H), 2.34 (s, 3H), 2.11-1.92 (m, 7H) | N-(2-((6-(2,6-dichloro-3,5-dimethoxyphenyl)imidazo[1',2':1,6]pyrido[2,3-d]pyrimidin-2-yl)amino)-5-(1-methylpiperidin-4-yl)phenyl)acrylamide | 632.2 |

| | | | |
|---|---|---|---|
| 24 | 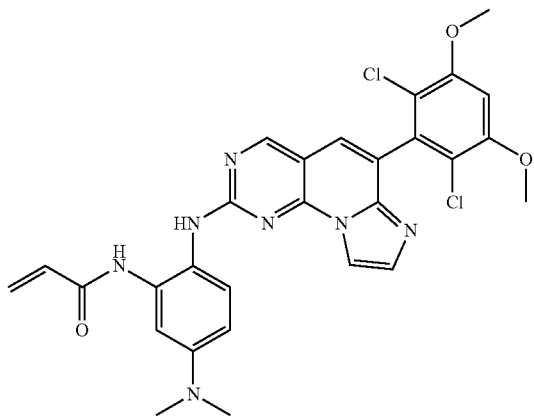 [SMILES: C=CC(=O)Nc1cc(N(C)C)ccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-(dimethylamino)phenyl)acrylamide | 578.1 |

(DMSO-d$_6$) δ 9.72 (brs, 1H), 9.17 (brs, 1H), 9.06 (s, 1H), 8.10 (s, 1H), 7.48 (m, 3H), 7.09-7.06 (m, 2H), 6.70-6.68 (d, 1H), 6.54-6.45 (m, 1H), 6.26-6.20 (dd, 1H), 5.72-5.68 (dd, 1H), 3.98 (s, 6H), 2.93 (s, 6H)

| | | | |
|---|---|---|---|
| 25 | 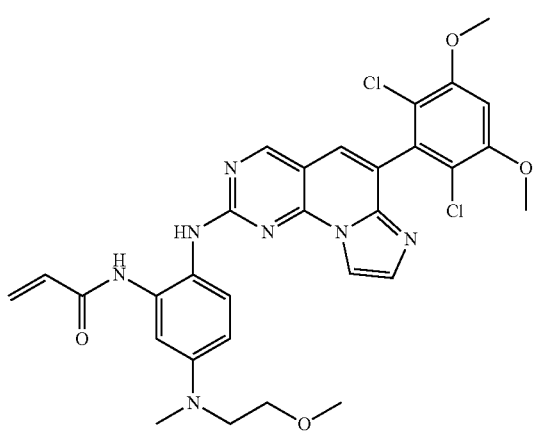 [SMILES: C=CC(=O)Nc1cc(N(C)CCOC)ccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-((2-methoxyethyl)(methyl)amino)phenyl)acrylamide | 622.2 |

(DMSO-d$_6$) δ 9.69 (brs, 1H), 9.14 (brs, 1H), 9.06 (s, 1H), 8.11 (s, 1H), 7.48 (m, 3H), 7.05 (m, 2H), 6.67-6.65 (m, 1H), 6.54-6.45 (m, 1H), 6.26-6.20 (dd, 1H), 5.72-5.68 (dd, 1H), 3.98 (s, 6H), 3.52 (s, 4H), 3.28 (s, 3H), 2.95 (s, 3H)

| | | | |
|---|---|---|---|
| 26 | 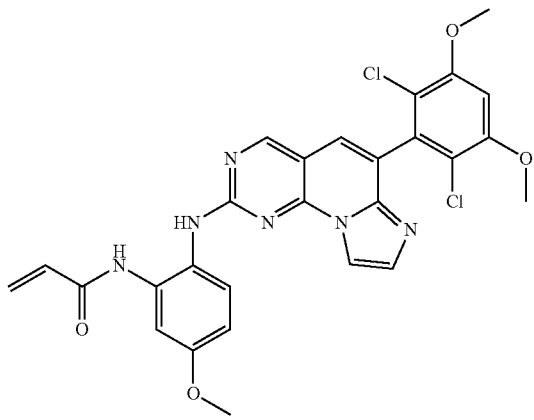 [SMILES: C=CC(=O)Nc1cc(OC)ccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-methoxyphenyl)acrylamide | 565.1 |

(DMSO-d$_6$) δ 9.68 (brs, 1H), 9.35 (brs, 1H), 9.09 (s, 1H), 8.11 (s, 1H), 7.62-7.60 (d, 1H), 7.50 (m, 2H), 7.44 (s, 1H), 7.06 (s, 1H), 6.88-6.84 (m, 1H), 6.55-6.46 (m, 1H), 6.26-6.19 (m, 1H), 5.71-5.67 (m, 1H), 3.99 (s, 6H), 3.79 (s, 3H)

| 27 | 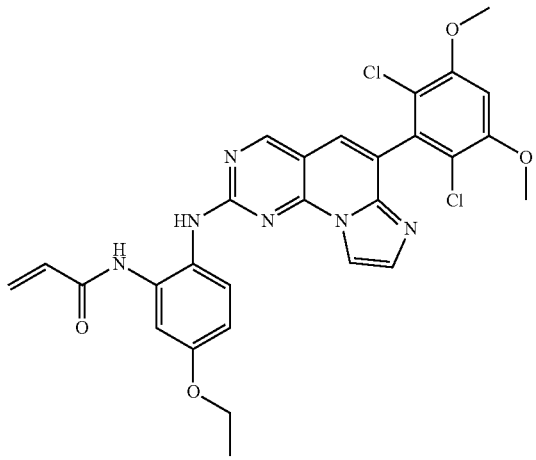 [SMILES: C=CC(=O)Nc1cc(OCC)ccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-ethoxyphenyl)acrylamide | 579.1 |
(DMSO-d$_6$) δ 9.67 (brs, 1H), 9.35 (brs, 1H), 9.09 (s, 1H), 8.10 (s, 1H), 7.60-7.57 (d, 1H), 7.50-7.49 (d, 2H), 7.43 (s, 1H), 7.06 (s, 1H), 6.85-6.82 (dd, 1H), 6.55-6.46 (m, 1H), 6.25-6.19 (d, 1H), 5.70-5.67 (d, 1H), 4.09-4.02 (q, 2H), 3.99 (s, 6H), 1.39-1.34 (t, 3H)
| 28 | 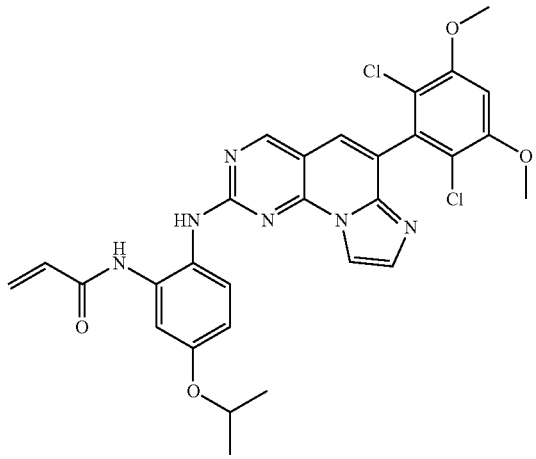 [SMILES: C=CC(=O)Nc1cc(OC(C)C)ccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-isopropoxyphenyl)acrylamide | 593.1 |
(DMSO-d$_6$) δ 9.60 (brs, 2H), 9.09 (s, 1H), 8.12 (s, 1H), 7.57 (m, 1H), 7.50 (s, 2H), 7.42 (s, 1H), 7.06 (s, 1H), 6.84-6.81 (d, 1H), 6.55-6.46 (m, 1H), 6.25-6.19 (d, 1H), 5.71-5.67 (d, 1H), 4.63-4.55 (m, 1H), 3.99 (s, 6H), 1.32-1.30 (d, 6H)

| | | | |
|---|---|---|---|
| 29 | 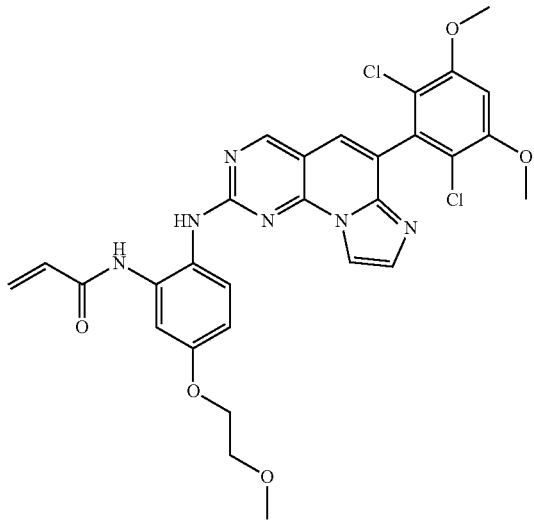 [SMILES: C=CC(=O)Nc1cc(OCCOC)ccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-(2-methoxyethoxy)phenyl)acrylamide | 609.1 |
(DMSO-d$_6$): δ 9.36 (brs, 1H), 9.09 (s, 1H), 8.11 (s, 1H), 7.61-7.58 (d, 1H), 7.50-7.49 (d, 2H), 7.44 (s, 1H), 7.06 (s, 1H), 6.87-6.84 (dd, 1H), 6.55-6.46 (m, 1H), 6.25-6.19 (d, 1H), 5.71-5.67 (d, 1H), 4.12-4.10 (t, 2H), 3.98 (s, 6H), 3.71-3.68 (t, 2H), 3.32 (s, 3H)
| | | | |
|---|---|---|---|
| 30 | 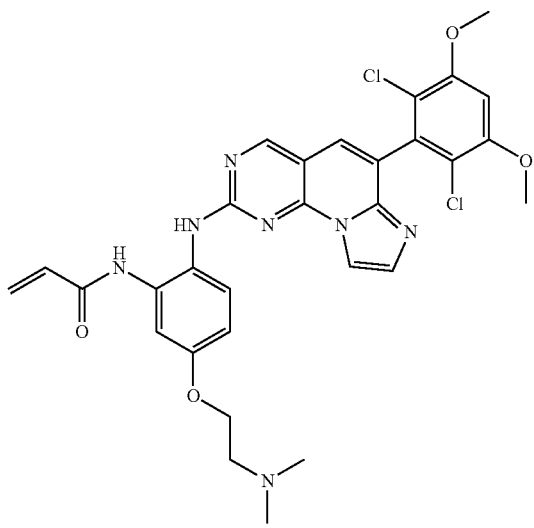 [SMILES: C=CC(=O)Nc1cc(OCCN(C)C)ccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-(2-(dimethylamino)ethoxy)phenyl)acrylamide | 622.2 |
(DMSO-d$_6$) δ 9.69 (brs, 1H), 9.36 (brs, 1H), 9.09 (s, 1H), 8.11 (s, 1H), 7.61-7.55 (m, 1H), 7.50-7.49 (d, 2H), 7.44 (s, 1H), 7.06 (s, 1H), 6.87-6.84 (d, 1H), 6.55-6.46 (m, 1H), 6.25-6.19 (d, 1H), 5.71-5.67 (d, 1H), 4.09-4.05 (t, 2H), 3.98 (s, 6H), 2.67-2.63 (t, 2H), 2.24 (s, 6H)

| 31 | 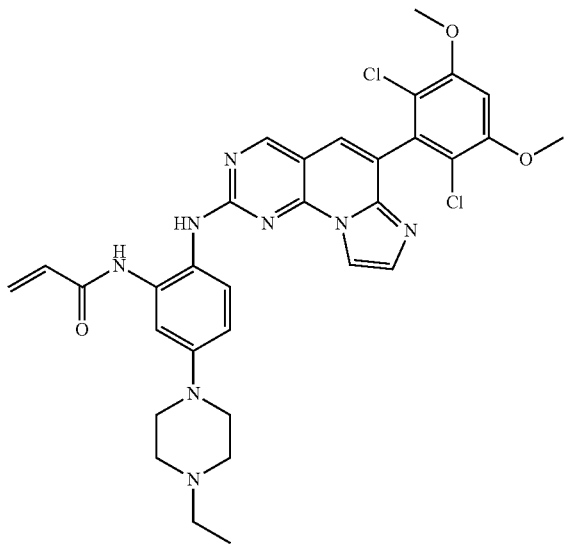 [SMILES: C=CC(=O)Nc1cc(N2CCN(CC)CC2)ccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-(4-ethylpiperazin-1-yl)phenyl)acrylamide | 647.2 |
(DMSO-d$_6$) δ 9.72 (brs, 1H), 9.25 (s, 1H), 9.08 (s, 1H), 8.12 (brs, 1H), 7.66 (brs, 1H), 7.49 (s, 2H), 7.29 (s, 1H), 7.05 (s, 1H), 6.90-6.87 (d, 1H), 6.53-6.44 (m, 1H), 6.25-6.20 (d, 1H), 5.71-5.68 (d, 1H), 3.98 (s, 6H), 3.16 (t, 4H), 2.50 (t, 4H), 2.42-2.35 (q, 2H), 1.07-1.02 (t, 3H)
| 32 | 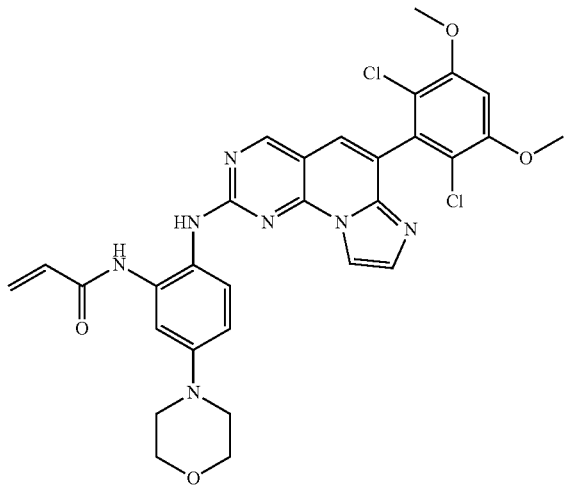 [SMILES: C=CC(=O)Nc1cc(N2CCOCC2)ccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-morpholinophenyl)acrylamide | 620.1 |
(CDCl$_3$) δ 8.88 (s, 1H), 8.44 (s, 1H), 8.05 (s, 1H), 7.96 (s, 1H), 7.56 (brs, 2H), 7.47 (s, 1H), 6.97 (d, 1H), 6.45 (s, 1H), 6.30 (d, 1H), 6.23 (m, 1H), 5.60 (d, 1H), 3.94 (s, 6H), 3.82 (t, 4H), 3.31 (t, 4H)

| 33 | 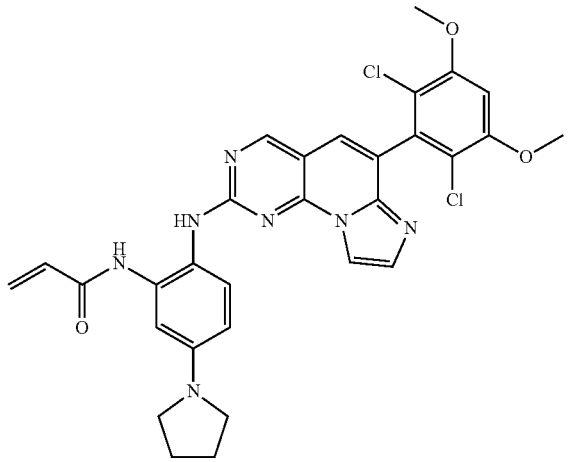 [SMILES: C=CC(=O)Nc1cc(N2CCCC2)ccc1Nc1ncc2cc(-c3c(Cl)c(OC)cc(OC)c3Cl)c3nccn3c2n1] (CDCl₃) δ 8.92 (s, 1H), 8.12 (s, 1H), 7.97 (s, 1H), 7.52 (s, 1H), 7.31 (m, 1H), 7.21 (m, 2H), 6.66 (s, 1H), 6.46 (m, 2H), 6.21 (m, 1H), 5.63 (dd, 1H), 3.94 (s, 6H), 3.39 (m, 4H), 2.09 (m, 4H) | N-(2-((6-(2,6-dichloro-3,5-dimethoxyphenyl)imidazo[1',2':1,6]pyrido[2,3-d]pyrimidin-2-yl)amino)-5-(pyrrolidin-1-yl)phenyl)acrylamide | 604.2 |
|---|---|---|---|
| 34 | 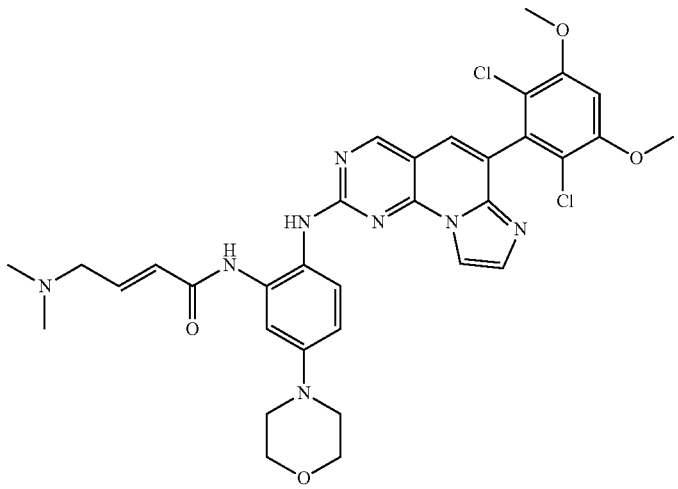 (CDCl₃) δ 8.88 (brs, 1H), 8.17 (brs, 1H), 8.09 (s, 1H), 7.73 (brs, 1H) 7.61 (brs, 1H), 7.44 (m, 2H), 7.26 (s, 1H), 6.95 (m, 1H), 6.76 (m, 1H), 6.65 (s, 1H), 6.03 (d, 1H), 3.94 (s, 6H), 3.86 (m, 4H), 3.21 (m, 4H), 3.01 (m, 2H), 2.18 (s, 6H) | (E)-N-(2-((6-(2,6-dichloro-3,5-dimethoxyphenyl)imidazo[1',2':1,6]pyrido[2,3-d]pyrimidin-2-yl)amino)-5-morpholinophenyl)-4-(dimethylamino)but-2-eneamide | 677.2 |

| 35 | 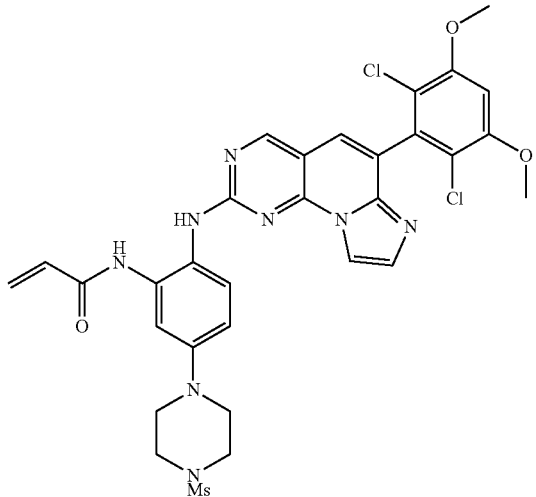 | N-(2-((6-(2,6-dichloro-3,5-dimethoxyphenyl)imidazo[1',2':1,6]pyrido[2,3-d]pyrimidin-2-yl)amino)-5-(4-(methylsulfonyl)piperazin-1-yl)phenyl)acrylamide | 697.1 |
(DMSO-d₆) δ 9.74 (brs, 1H), 9.30 (brs, 1H), 9.09 (s, 1H), 8.12 (s, 1H), 7.50 (brs, 1H), 7.36 (s, 2H), 7.20 (s, 1H), 7.06 (s, 1H), 6.95-6.92 (d, 1H), 6.50-6.45 (m, 1H), 6.26-6.20 (d, 1H), 5.72-5.68 (d, 1H), 3.99 (s, 6H), 3.42-3.28 (m, 8H), 2.94 (s, 3H)
| 36 | 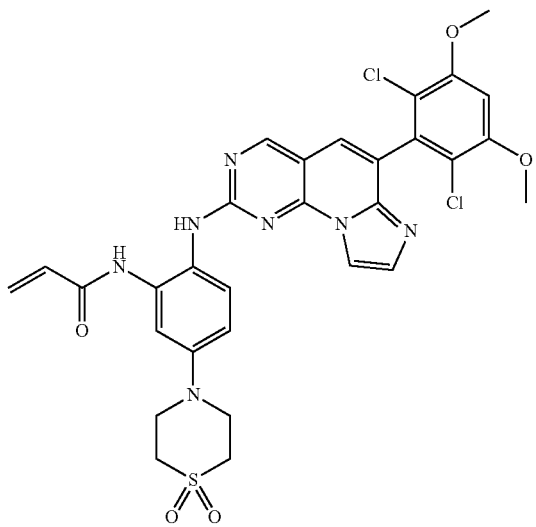 [SMILES: C=CC(=O)Nc1cc(N2CCS(=O)(=O)CC2)ccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-(1,1-dioxidothiomorpholino)phenyl)acrylamide | 668.1 |
(DMSO-d₆) δ 9.75 (brs, 1H), 9.31 (s, 1H), 9.09 (s, 1H), 8.14 (s, 1H), 7.65 (s, 1H), 7.50 (s, 2H), 7.38 (s, 1H), 7.06 (s, 1H), 7.00-6.98 (d, 1H), 6.54-6.45 (m, 1H), 6.27-6.21 (d, 1H), 5.73-5.70 (d, 1H), 3.99 (s, 6H), 3.79 (m, 4H), 3.19 (m, 4H)

| | | | |
|---|---|---|---|
| 37 | 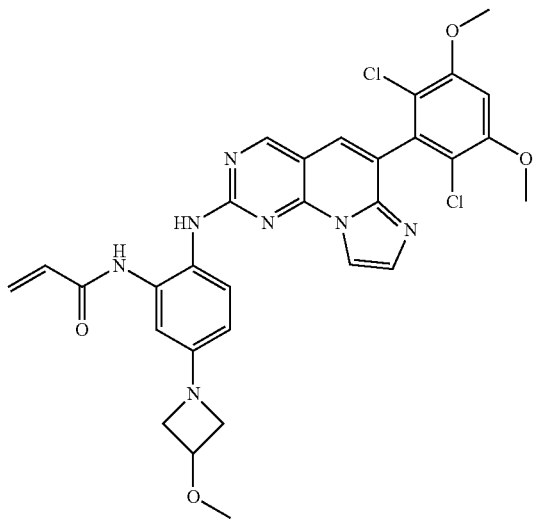 [SMILES: C=CC(=O)Nc1cc(N2CC(OC)C2)ccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-(3-methoxyazetidin-1-yl)phenyl)acrylamide | 620.1 |
| | (DMSO-d$_6$) δ 9.64 (brs, 1H), 9.20 (brs, 1H), 9.06 (s, 1H), 8.09 (s, 1H), 7.48 (s, 3H), 7.06 (s, 1H), 6.88 (s, 1H), 6.53-6.44 (m, 1H), 6.39-6.36 (d, 1H), 6.24-6.18 (d, 1H), 5.70-5.66 (d, 1H), 4.34 (m, 1H), 4.10-4.05 (t, 2H), 3.98 (s, 6H), 3.64-3.60 (m, 2H), 3.26 (s, 3H) | | |
| 38 | 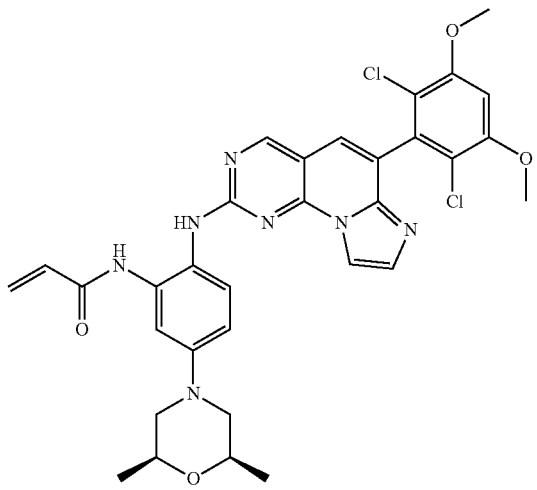 [SMILES: C=CC(=O)Nc1cc(N2C[C@@H](C)O[C@@H](C)C2)ccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-((2S,6R)-2,6-dimethylmorpholino)phenyl)acrylamide | 648.2 |
| | (DMSO-d$_6$) δ 9.73 (s, 1H), 9.27 (s, 1H), 9.09 (s, 1H), 8.11 (s, 1H), 7.61-7.57 (m, 1H), 7.29 (s, 1H), 7.06 (s, 1H), 6.92-6.89 (d, 1H), 6.54-6.45 (m, 1H), 6.26-6.20 (d, 1H), 5.72-5.68 (d, 1H), 3.99 (s, 6H), 3.72 (m, 2H), 3.59-3.55 (d, 2H), 2.33-2.26 (t, 2H), 1.19-1.17 (d, 6H) | | |

| 39 | 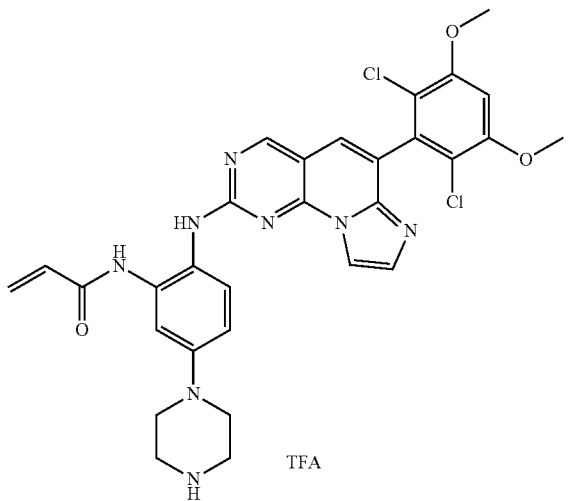 [SMILES: C=CC(=O)Nc1cc(N2CCNCC2)ccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-(piperazin-1-yl)phenyl)acrylamide trifluoroacetate | 719.2 |
(DMSO-d₆): δ 9.69 (s, 1H), 9.43 (s, 1H), 9.13 (s, 1H), 8.76 (m, 2H) 8.14 (s, 1H), 7.58 (m, 2H), 7.07 (m, 2H), 6.49 (m, 1H), 6.23 (m, 1H), 5.75 (m, 2H), 3.98 (s, 6H), 3.29 (m, 4H), 2.51 (m, 4H).
| 40 | 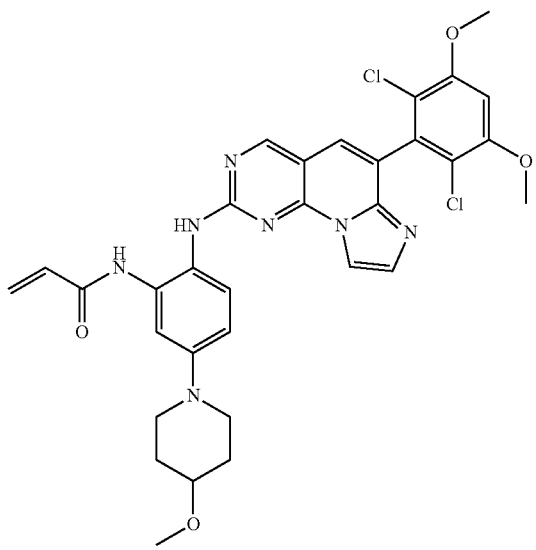 [SMILES: C=CC(=O)Nc1cc(N2CCC(OC)CC2)ccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-(4-methoxypiperidin-1-yl)phenyl)acrylamide | 648.2 |
(DMSO-d₆) δ 9.72 (brs, 1H), 9.27 (brs, 1H), 9.08 (s, 1H), 8.11 (s, 1H), 7.57 (brs, 1H), 7.49 (s, 2H), 7.31 (s, 1H), 7.06 (s, 1H), 6.90-6.87 (d, 1H), 6.54-6.45 (m, 1H), 6.25-6.20 (d, 1H), 5.71-5.68 (d, 1H), 3.98 (s, 6H), 3.52-3.26 (m, 6H), 2.96-2.89 (t, 2H), 1.99-1.95 (m, 2H), 1.56-1.53 (m, 2H)

| 41 | 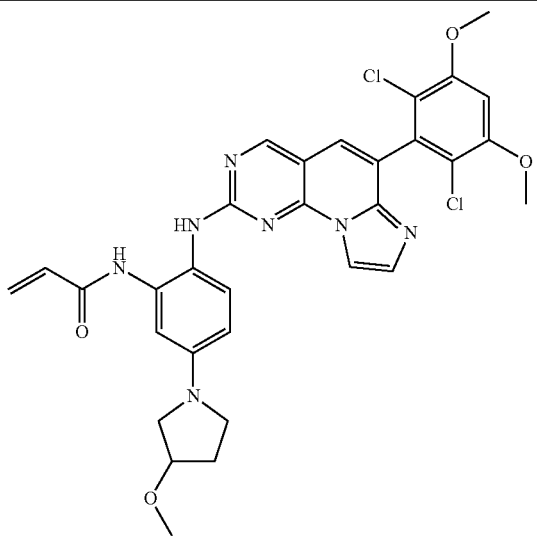 | N-(2-((6-(2,6-dichloro-3,5-dimethoxyphenyl)imidazo[1',2':1,6]pyrido[2,3-d]pyrimidin-2-yl)amino)-5-(3-methoxypyrrolidin-1-yl)phenyl)acrylamide | 634.2 |
|---|---|---|---|
| | (DMSO-$d_6$) δ 9.69 (brs, 1H), 9.14 (s, 1H), 9.06 (s, 1H), 8.08 (s, 1H), 7.48 (m, 3H), 7.05 (s, 1H), 6.93 (s, 1H), 6.54-6.45 (m, 2H), 6.25-6.19 (d, 1H), 5.70-5.67 (d, 1H), 4.11 (m, 1H), 3.98 (s, 6H), 3.48-3.25 (m, 7H), 2.08 (m, 2H) | | |
| 42 | 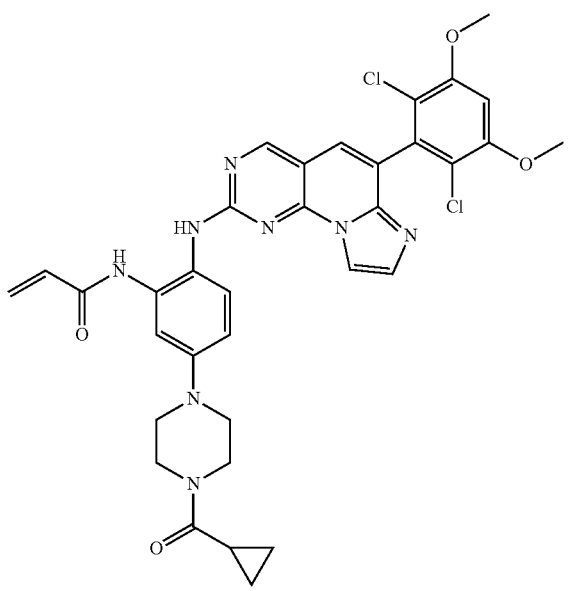 [SMILES: C=CC(=O)Nc1cc(N2CCN(C(=O)C3CC3)CC2)ccc1Nc1ncc2cc(-c3c(Cl)c(OC)cc(OC)c3Cl)c3nccn3c2n1] | N-(5-(4-(cyclopropanecarbonyl)piperazin-1-yl)-2-((6-(2,6-dichloro-3,5-dimethoxyphenyl)imidazo[1',2':1,6]pyrido[2,3-d]pyrimidin-2-yl)amino)phenyl)acrylamide | 687.2 |
| | (CDCl$_3$) δ 10.54 (brs, 1H), 9.74 (brs, 1H), 9.08 (s, 1H), 8.12 (s, 1H), 7.63 (m, 1H), 7.35 (m, 1H), 7.06 (m, 2H), 6.51 (m, 1H), 6.19 (m, 1H), 5.67 (m, 1H), 3.98 (s, 6H), 3.86 (m, 4H), 3.21 (m, 4H), 2.08 (m, 1H), 0.75 (m, 4H) | | |

| 43 | 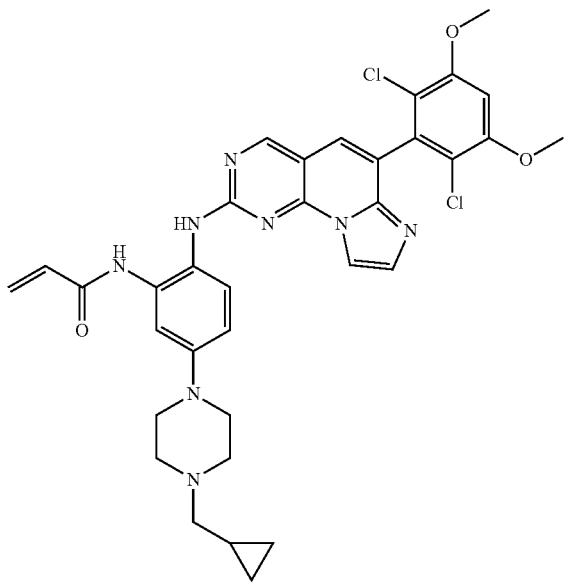 [SMILES: C=CC(=O)Nc1cc(N2CCN(CC3CC3)CC2)ccc1Nc1ncc2cc(-c3c(Cl)c(OC)cc(OC)c3Cl)c3nccn3c2n1] | N-(5-(4-(cyclopropylmethyl)piperazin-1-yl)-2-((6-(2,6-dichloro-3,5-dimethoxyphenyl)imidazo[1',2':1,6]pyrido[2,3-d]pyrimidin-2-yl)amino)phenyl)acrylamide | 673.2 |
(DMSO-d$_6$): δ 9.76 (s, 1H), 9.26 (s, 1H), 9.06 (s, 1H), 8.09 (m, 1H) 7.47 (m, 3H), 6.88 (m, 1H), 6.49 (m, 1H), 6.23 (m, 1H), 5.69 (m, 2H), 5.01 (m, 1H), 3.96 (s, 6H), 3.15 (m, 4H), 3.23 (4, 4H), 2.32 (m, 2H), 0.90 (m, 1H), 0.53 (m, 2H), 0.17 (m, 2H)
| 44 | 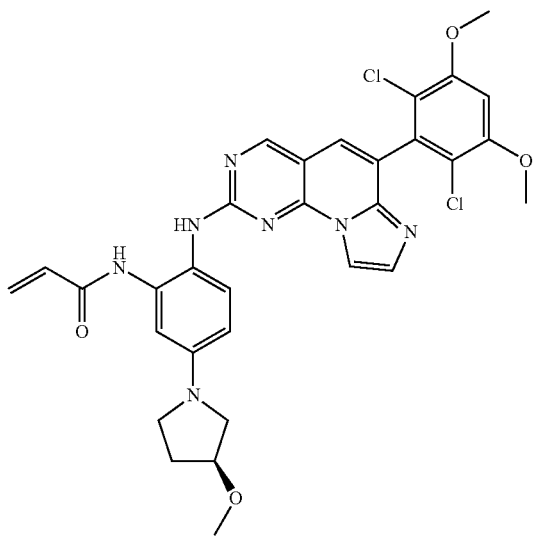 [SMILES: C=CC(=O)Nc1cc(N2CC[C@H](OC)C2)ccc1Nc1ncc2cc(-c3c(Cl)c(OC)cc(OC)c3Cl)c3nccn3c2n1] | (S)-N-(2-((6-(2,6-dichloro-3,5-dimethoxyphenyl)imidazo[1',2':1,6]pyrido[2,3-d]pyrimidin-2-yl)amino)-5-(3-methoxypyrrolidin-1-yl)phenyl)acrylamide | 634.2 |
(DMSO-d$_6$) δ 9.69 (s, 1H), 9.14 (s, 1H), 9.06 (s, 1H), 8.08 (s, 1H), 7.51-7.45 (m, 3H), 7.05 (s, 1H), 6.93 (s, 1H), 6.54-6.45 (m, 2H), 6.25-6.19 (d, 1H), 5.71-5.67 (d, 1H), 4.11 (m, 1H), 3.95 (s, 6H), 3.37-3.26 (m, 7H), 2.08 (m, 2H)

| | | | |
|---|---|---|---|
| 45 | 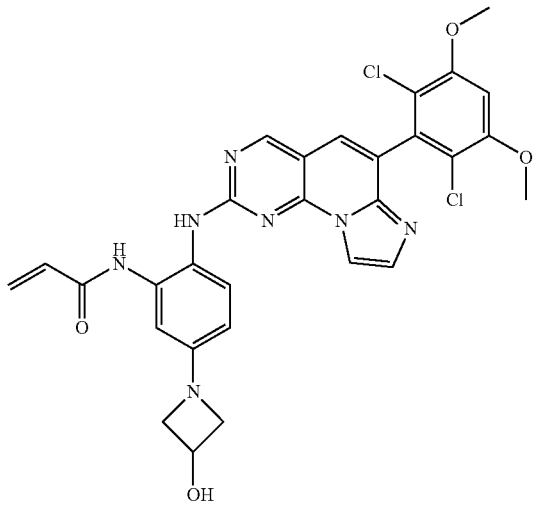 [SMILES: C=CC(=O)Nc1cc(N2CC(O)C2)ccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-(3-hydroxyazetidin-1-yl)phenyl)acrylamide | 606.1 |
| | (DMSO-$d_6$) δ 9.67 (brs, 1H), 9.21 (brs, 1H), 9.06 (s, 1H), 8.09 (s, 1H), 7.48-7.46 (m, 3H), 7.06 (s, 1H), 6.85 (s, 1H), 6.54-6.45 (m, 1H), 6.38-6.35 (d, 1H), 6.24-6.18 (d, 1H), 5.71-5.67 (d, 1H), 4.81 (brs, 1H), 4.58 (m, 1H), 4.12-4.07 (t, 2H), 3.98 (s, 6H), 3.56-3.52 (t, 2H) | | |
| 46 | 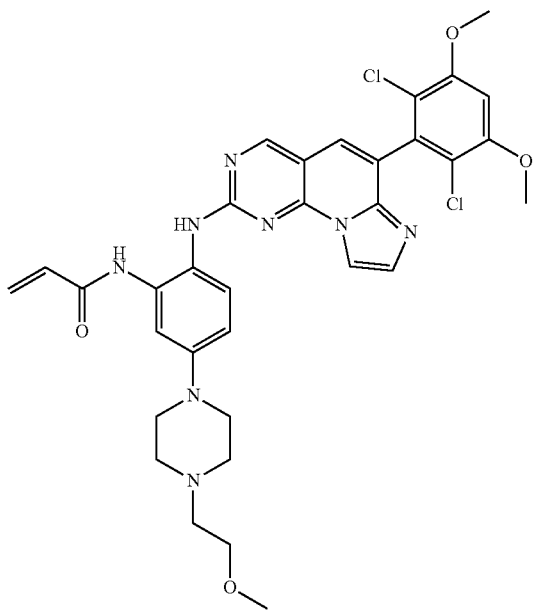 [SMILES: C=CC(=O)Nc1cc(N2CCN(CCOC)CC2)ccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-(4-(2-methoxyethyl)piperazin-1-yl)phenyl)acrylamide | — |
| | (DMSO-$d_6$): δ 9.72 (brs, 1H), 9.26 (brs, 1H), 9.08 (s, 1H), 8.12 (s, 1H), 7.49 (m, 3H), 7.30 (s, 1H), 7.06 (s, 1H), 6.90-6.88 (d, 1H), 6.54-6.45 (m, 1H), 5.72-5.68 (d, 1H), 3.98 (s, 6H), 3.39 (m, 2H), 3.27 (s, 3H), 3.17 (m, 4H), 2.50 (m, 6H) | | |

| 47 | 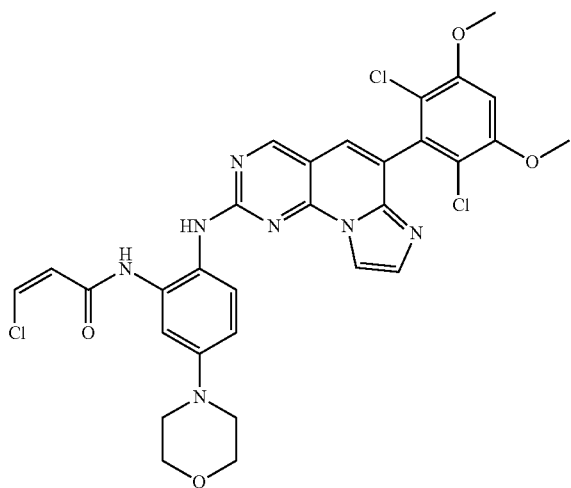 [SMILES: COc1cc(OC)c(Cl)c(-c2cc3cnc(Nc4ccc(N5CCOCC5)cc4NC(=O)/C=C\Cl)nc3n3ccnc23)c1Cl] | (Z)-3-chloro-N-(2-((6-(2,6-dichloro-3,5-dimethoxyphenyl)imidazo[1',2':1,6]pyrido[2,3-d]pyrimidin-2-yl)amino)-5-morpholinophenyl)acrylamide | 654.1 |
(DMSO-d₆): δ 9.96 (s, 1H), 8.87 (d, 2H), 8.48 (m, 2H), 8.27 (m, 2H), 7.62 (m, 2H), 6.63 (s, 1H), 3.96 (s, 6H), 3.57 (m, 2H), 3.24 (m, 2H), 2.16 (m, 4H)
| 48 | 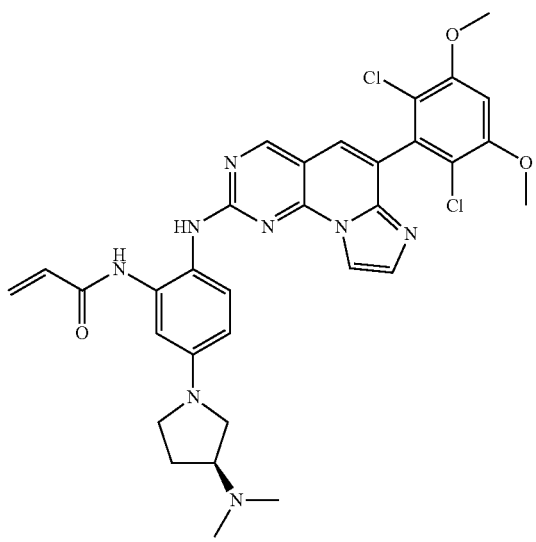 [SMILES: C=CC(=O)Nc1cc(N2CC[C@H](N(C)C)C2)ccc1Nc1ncc2cc(-c3c(Cl)c(OC)cc(OC)c3Cl)c3nccn3c2n1] | (S)-N-(2-((6-(2,6-dichloro-3,5-dimethoxyphenyl)imidazo[1',2':1,6]pyrido[2,3-d]pyrimidin-2-yl)amino)-5-(3-(dimethylamino)pyrrolidin-1-yl)phenyl)acrylamide | 647.2 |
(DMSO-d6) δ 9.70 (s, 1H), 9.15 (s, 1H), 9.06 (s, 1H), 8.08 (s, 1H), 7.52-7.48 (m, 3H), 7.05 (s, 1H), 6.90 (s, 1H), 6.54-6.45 (m, 2H), 6.25-6.19 (d, 1H), 5.70-5.67 (d, 1H), 3.98 (s, 6H), 3.35 (m, 3H), 3.09-3.03 (t, 1H), 2.83 (t, 1H), 2.21 (s, 6H), 2.17 (m, 1H), 1.87-1.80 (t, 1H)

| 49 | 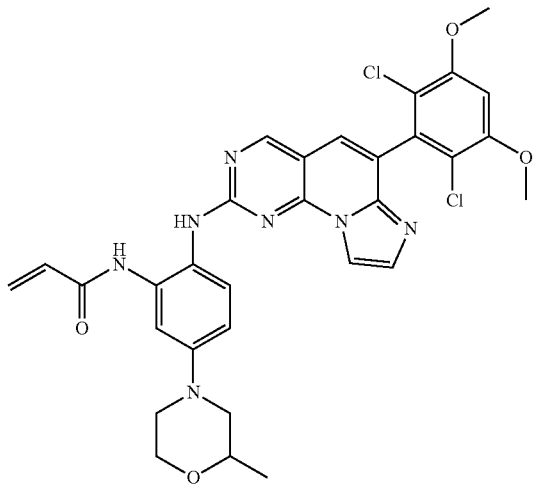 [SMILES: C=CC(=O)Nc1cc(N2CCOC(C)C2)ccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-(2-methylmorpholino)phenyl)acrylamide | 634.2 |
(DMSO-d$_6$) δ 9.72 (s, 1H), 9.27 (s, 1H), 9.08 (s, 1H), 8.11 (s, 1H), 7.61 (s, 1 H), 7.46 (m, 2H), 7.30 (s, 1H), 7.06 (s, 1H), 6.92-6.89 (d, 1H), 6.53-6.45 (m, 1H), 6.25-6.20 (d, 1H), 5.72-5.68 (d, 1H), 4.01-3.92 (m, 7H), 3.69-3.46 (m, 4H), 2.72-2.65 (t, 1H), 2.41-2.33 (t, 1H), 1.19-1.17 (d, 3H)
| 50 | 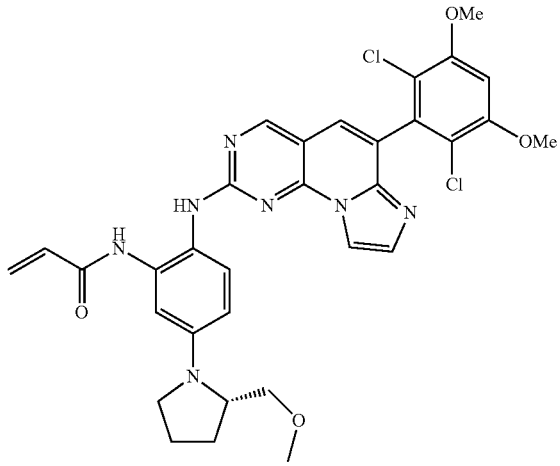 [SMILES: C=CC(=O)Nc1cc(N2CCC[C@H]2COC)ccc1Nc1ncc2cc(-c3c(Cl)c(OC)cc(OC)c3Cl)c3nccn3c2n1] | (S)-N-(2-((6-(2,6-dichloro-3,5-dimethoxyphenyl)imidazo[1',2':1,6]pyrido[2,3-d]pyrimidin-2-yl)amino)-5-(2-(methoxymethyl)pyrrolidin-1-yl)phenyl)acrylamide | 648.2 |
(CDCl$_3$) δ 8.90 (s, 1H), 7.94 (s, 1H), 7.38 (m 3H), 7.24 (s, 2H), 6.63 (s, 1H), 6.52 (dd, 1H), 6.36 (m, 2H), 5.64 (m, 1H), 3.93 (s, 6H), 3.55 (m, 2H), 3.39 (s, 3H), 3.24 (m, 2H), 2.01 (m, 5H)

| 51 | 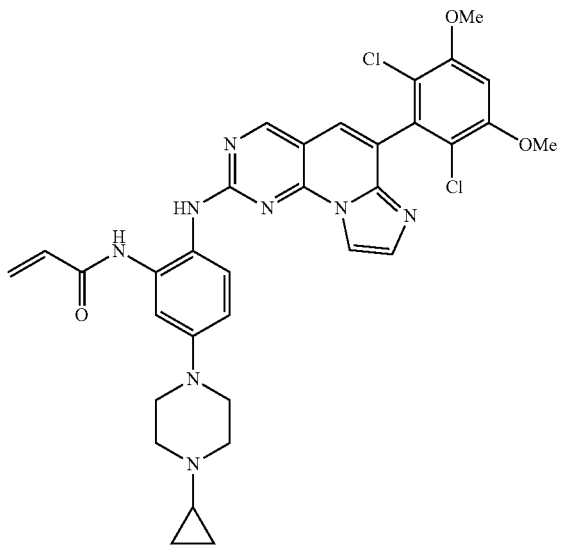 [SMILES: C=CC(=O)Nc1cc(N2CCN(C3CC3)CC2)ccc1Nc1ncc2cc(-c3c(Cl)c(OC)cc(OC)c3Cl)c3nccn3c2n1] | N-(5-(4-cyclopropylpiperazin-1-yl)-2-((6-(2,6-dichloro-3,5-dimethoxyphenyl)imidazo[1',2':1,6]pyrido[2,3-d]pyrimidin-2-yl)amino)phenyl)acrylamide | 659.2 |
|---|---|---|---|
(DMSO-d$_6$) δ 9.71 (s, 1H), 9.27 (s, 1H), 9.07 (s, 1H), 8.25 (s, 1H), 7.56 (s, 1H), 7.49 (m, 1H), 7.29 (m, 1H), 6.89 (m, 1H), 6.58 (m, 1H), 6.25 (m, 1H), 5.54 (m, 1H), 3.98 (s, 6H), 3.11 (m, 4H), 2.69 (m, 4H), 0.85 (m, 1H), 0.36 (m, 4H)
| 52 | 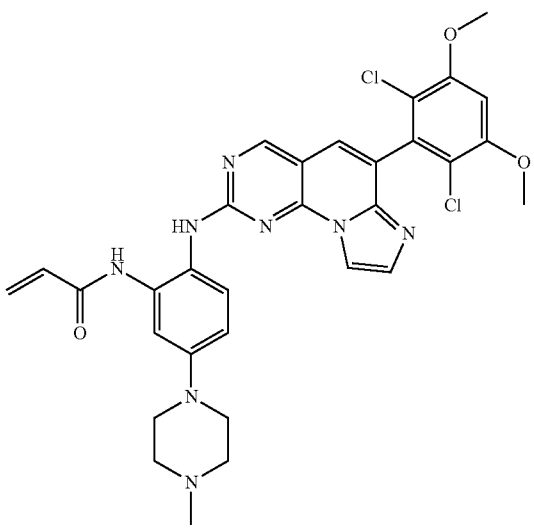 [SMILES: C=CC(=O)Nc1cc(N2CCN(C)CC2)ccc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-(4-methylpiperazin-1-yl)phenyl)acrylamide | 633.2 |
|---|---|---|---|
(DMSO-d$_6$) δ 9.72 (s, 1H), 9.27 (s, 1H), 9.08 (s, 1H), 8.12 (s, 1H), 7.59 (brs, 1H), 7.49 (s, 2H), 7.30 (s, 1H), 7.06 (s, 1H), 6.91-6.88 (d, 1H), 6.53-6.45 (m, 1H), 6.25-6.19 (d, 1H), 5.72-5.68 (d, 1H), 3.99 (s, 6H), 3.15 (m, 4H), 2.50 (m, 4H), 2.24 (s, 3H)

| 53 | 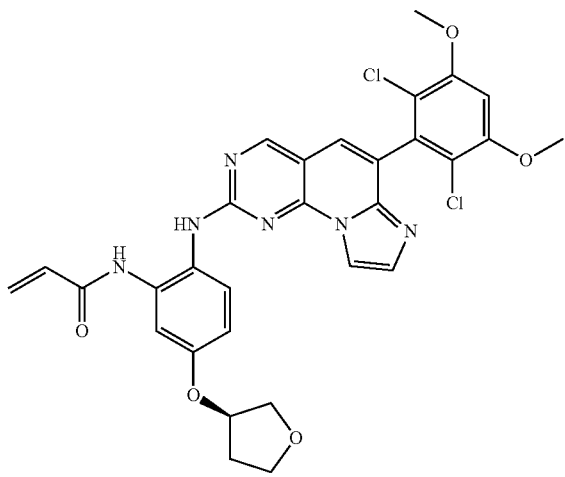 [SMILES: C=CC(=O)Nc1cc(O[C@@H]2CCOC2)ccc1Nc1ncc2cc(-c3c(Cl)c(OC)cc(OC)c3Cl)c3nccn3c2n1] | (R)-N-(2-((6-(2,6-dichloro-3,5-dimethoxyphenyl)imidazo[1',2':1,6]pyrido[2,3-d]pyrimidin-2-yl)amino)-5-((tetrahydrofuran-3-yl)oxy)phenyl)acrylamide | 621.1 |
(DMSO-d$_6$) δ 9.71 (brs, 1H), 9.41 (brs, 1H), 9.10 (s, 1H), 8.11 (s, 1H), 7.61-7.59 (d, 1H), 7.50 (s, 2H), 7.44 (s, 1H), 7.06 (s, 1H), 6.85-6.82 (dd, 1H), 6.56-6.47 (m, 1H), 6.26-6.20 (d, 1H), 5.71-5.67 (m, 1H), 5.03 (m, 1H), 5.03 (m, 1H), 4.04-3.76 (m, 10H), 2.28-2.22 (m, 1H), 2.08-1.99 (m, 1H)
| 54 | 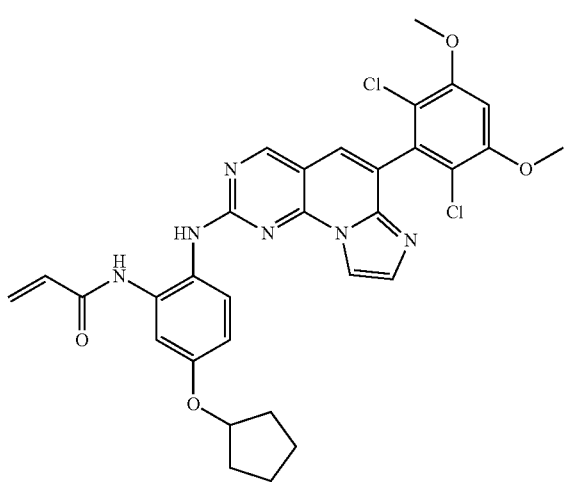 [SMILES: C=CC(=O)Nc1cc(OC2CCCC2)ccc1Nc1ncc2cc(-c3c(Cl)c(OC)cc(OC)c3Cl)c3nccn3c2n1] | N-(5-(cyclopentyloxy)-2-((6-(2,6-dichloro-3,5-dimethoxyphenyl)imidazo[1',2':1,6]pyrido[2,3-d]pyrimidin-2-yl)amino)phenyl)acrylamide | 619.2 |
(DMSO-d$_6$) δ 9.64 (s, 1H), 9.44 (s, 1H), 9.34 (s, 1H), 9.09 (s, 1H), 8.11 (s, 1H), 7.56 (s, 1H), 7.50 (s, 2H), 7.41 (s, 1H), 7.06 (s, 1H), 6.82-6.79 (dd, 1H), 6.55-6.46 (m, 1H), 6.25-6.19 (dd, 1H), 5.71-5.67 (d, 1H), 4.81 (m, 1H), 3.99 (s, 6H), 1.99-1.94 (m, 2H), 1.75-1.61 (m, 6H)

| # | Structure | Name | MW |
|---|---|---|---|
| 55 | 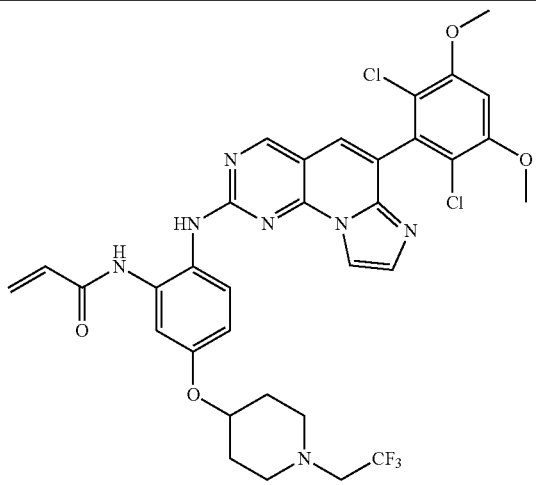 (DMSO-d₆): δ 9.67 (brs, 1H), 9.35 (brs, 1H), 9.09 (s, 1H), 8.12 (s, 1H), 7.59 (d, 1H), 7.50 (d, 2H), 7.44 (s, 1H), 7.06 (s, 1H), 6.88-6.86 (d, 1H), 6.54-6.45 (m, 1H), 6.25-6.20 (d, 1H), 5.71-5.68 (d, 1H), 4.40 (m, 1H), 3.99 (s, 6H), 3.26-3.16 (q, 2H), 2.88 (m, 2H), 2.63-2.60 (m, 2H), 1.99 (m, 2H), 1.71-1.68 (m, 2H) | N-(2-((6-(2,6-dichloro-3,5-dimethoxyphenyl)imidazo[1',2':1,6]pyrido[2,3-d]pyrimidin-2-yl)amino)-5-((1-(2,2,2-trifluoroethyl)piperidin-4-yl)oxy)phenyl)acrylamide | 716.2 |
| 56 | 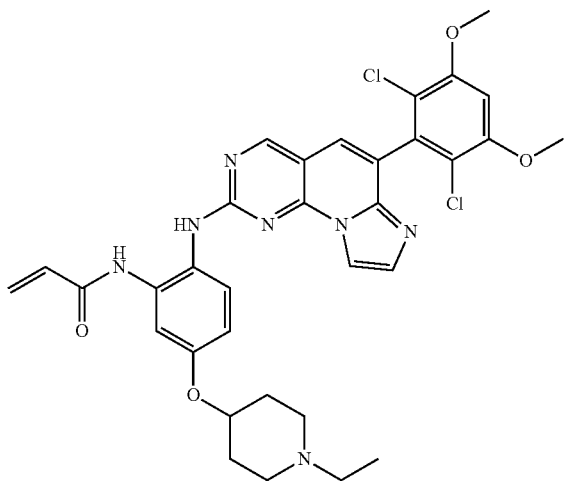 [SMILES: C=CC(=O)Nc1cc(OC2CCN(CC)CC2)ccc1Nc1ncc2cc(-c3c(Cl)c(OC)cc(OC)c3Cl)c3nccn3c2n1] (CDCl₃) δ 8.86 (s, 1H), 8.68 (brs, 1H), 7.91 (s, 1H), 7.76 (s, 1H), 7.38 (m, 3H), 6.79 (m, 1H), 6.64 (s, 1H), 6.34 (m, 2H), 5.66 (m, 1H), 4.40 (m, 1H), 3.93 (s, 6H), 2.76 (m, 2H), 2.46 (m, 4H), 1.90 (m, 6H). | N-(2-((6-(2,6-dichloro-3,5-dimethoxyphenyl)imidazo[1',2':1,6]pyrido[2,3-d]pyrimidin-2-yl)amino)-5-((1-ethylpiperidin-4-yl)oxy)phenyl)acrylamide | 662.2 |
| 57 | 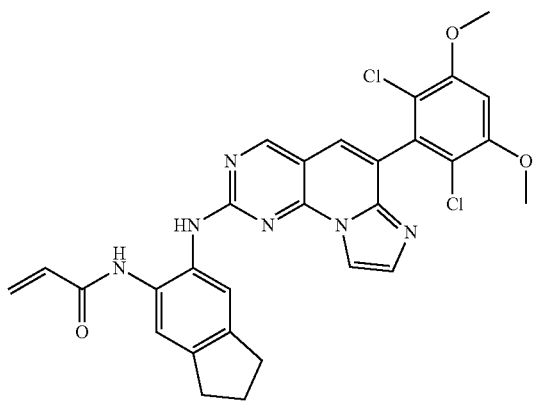 [SMILES: C=CC(=O)Nc1cc2c(cc1Nc1ncc3cc(-c4c(Cl)c(OC)cc(OC)c4Cl)c4nccn4c3n1)CCC2] (DMSO-d₆): δ 9.67 (s, 1H), 9.38 (s, 1H), 9.11 (s, 1H), 8.13 (s, 1H), 7.63 (s, 1H), 7.51 (m, 3H), 7.06 (s, 1H), 6.51-6.42 (m, 1H), 6.22-6.17 (d, 1H), 5.69-5.65 (d, 1H), 3.99 (s, 6H), 2.91 (m, 4H), 2.10-2.05 (m, 2H) | N-(6-((6-(2,6-dichloro-3,5-dimethoxyphenyl)imidazo[1',2':1,6]pyrido[2,3-d]pyrimidin-2-yl)amino)-2,3-dihydro-1H-inden-5-yl)acrylamide | 575.1 |

| | | | |
|---|---|---|---|
| 58 | 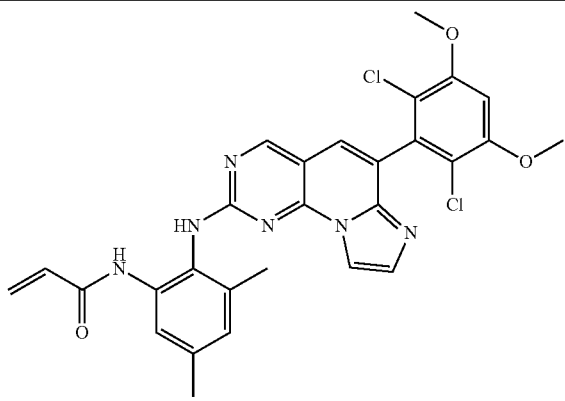 (CDCl₃) δ 9.33 (s, 1H), 8.37 (d, 1H), 8.17 (s, 1H), 7.77 (m, 2H), 7.50 (m, 1H), 6.97 (s, 1H), 6.26 (m, 2H), 5.58 (m, 1H), 4.00 (s, 6H), 2.44 (s, 3H), 2.31 (s, 3H). | N-(2-((6-(2,6-dichloro-3,5-dimethoxyphenyl)imidazo[1',2':1,6]pyrido[2,3-d]pyrimidin-2-yl)amino)-3,5-dimethylphenyl)acrylamide | 563.1 |
| 59 | 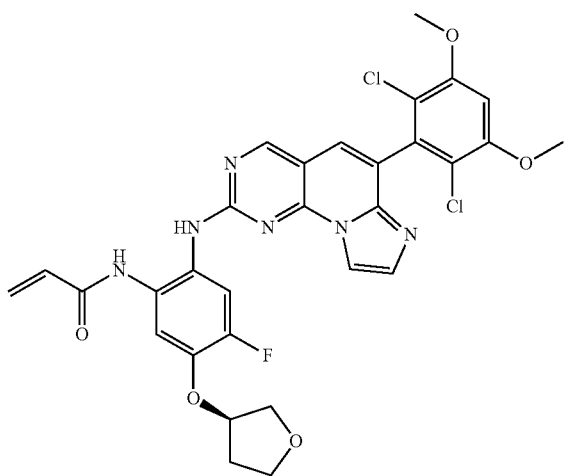 (DMSO-d₆) δ 9.77 (s, 1H), 9.44 (s, 1H), 9.14 (s, 1H), 8.14 (s, 1H), 7.74-7.69 (d, 1H), 7.55-7.52 (m, 3H), 7.06 (s, 1H), 6.54-6.45 (m, 1H), 6.28-6.21 (dd, 1H), 5.75-5.71 (dt, 1H), 5.06 (m, 1H), 3.99 (s, 6H), 3.93-3.27 (m, 4H), 2.28-2.22 (m, 1H), 2.09-1.99 (m, 1H) | (R)-N-(2-((6-(2,6-dichloro-3,5-dimethoxyphenyl)imidazo[1',2':1,6]pyrido[2,3-d]pyrimidin-2-yl)amino)-4-fluoro-5-((tetrahydrofuran-3-yl)oxy)phenyl)acrylamide | 639.1 |
| 60 | 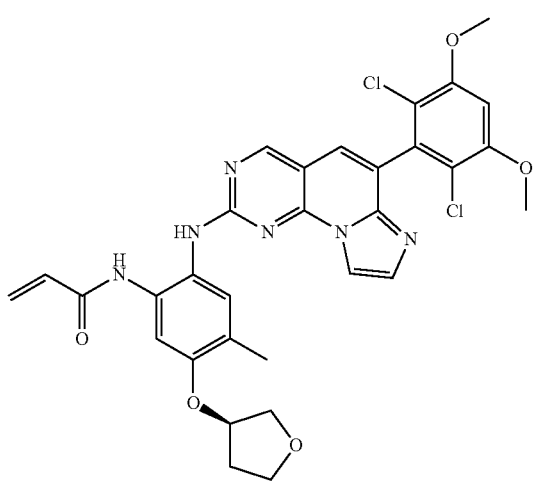 [SMILES: C=CC(=O)Nc1cc(O[C@@H]2CCOC2)c(C)cc1Nc1ncc2cc(-c3c(Cl)c(OC)cc(OC)c3Cl)c3nccn3c2n1] (DMSO-d₆) δ 9.70 (brs, 1H), 9.32 (brs, 1H), 9.09 (s, 1H), 8.10 (s, 1H), 7.50 (s, 3H), 7.37 (s, 1H), 7.06 (s, 1H), 6.54-6.45 (m, 1H), 6.25-6.20 (dd, 1H), 5.71-5.67 (dd, 1H), 4.99 (m, 1H), 3.99 (s, 6H), 3.96-3.79 (m, 4H), 2.28-2.05 (m, 5H) | (R)-N-(2-((6-(2,6-dichloro-3,5-dimethoxyphenyl)imidazo[1',2':1,6]pyrido[2,3-d]pyrimidin-2-yl)amino)-4-methyl-5-((tetrahydrofuran-3-yl)oxy)phenyl)acrylamide | 635.2 |

| 61 | 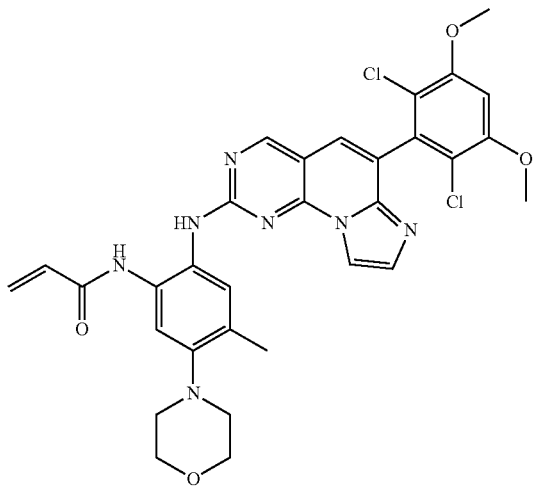 [SMILES: C=CC(=O)Nc1cc(N2CCOCC2)c(C)cc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-4-methyl-5-morpholinophenyl)acrylamide | 634.2 |
(DMSO-d$_6$) δ 10.37 (s, 1H), 9.51 (s, 1H), 9.20 (s, 1H), 9.10 (brs, 1H), 8.88 (brs, 1H), 7.60 (d, 1H), 7.55 (s, 1H), 7.14 (s, 1H), 7.07 (s, 1H), 6.70-6.61 (m, 1H), 6.38-6.32 (d, 1H), 5.86-5.82 (d, 1H), 4.00 (s, 6H), 3.79 (m, 4H), 3.30 (m, 4H), 2.27 (s, 3H)
| 62 | 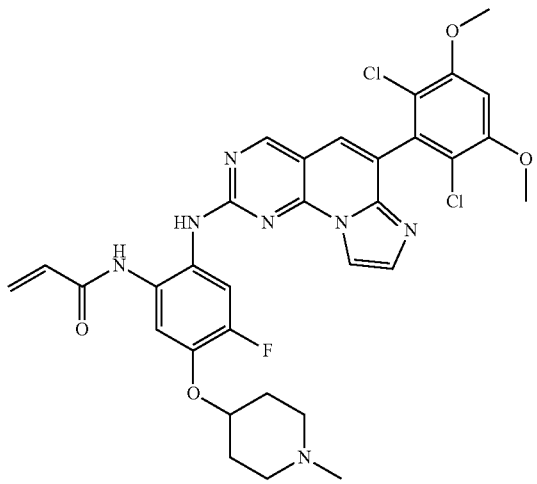 [SMILES: C=CC(=O)Nc1cc(OC2CCN(C)CC2)c(F)cc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-4-fluoro-5-((1-methylpiperidin-4-yl)oxy)phenyl)acrylamide | 666.2 |
(DMSO-d$_6$) δ 9.78 (brs, 1H), 9.45 (brs, 1H), 9.14 (s, 1H), 8.14 (s, 1H), 7.73-7.68 (d, 1H), 7.56-7.52 (m, 3H), 7.06 (s, 1H), 6.53-6.44 (m, 1H), 6.27-6.21 (d, 1H), 5.74-5.70 (d, 1H), 4.65 (m, 1H), 3.99 (s, 6H), 2.52 (m, 2H), 2.27-2.15 (m, 5H), 1.98 (m, 2H), 1.73 (m, 2H)

| | | | |
|---|---|---|---|
| 63 | 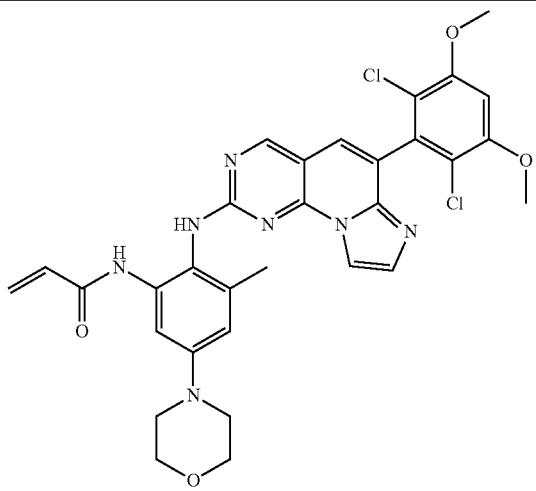 (DMSO-d$_6$): δ 9.45-9.30 (d, 1H), 9.11-9.06 (d, 1H), 8.95 (s, 1H), 8.30-7.79 (d, 1H), 7.48-7.41 (m, 2H), 7.31 (s, 1H), 7.05 (s, 1H), 6.79 (d, 1H), 6.50 (m, 1 H), 6.16 (m, 1H), 5.63 (m, 1H), 3.98 (s, 6H), 3.76 (m, 4H), 3.13 (m, 4H), 2.49 (s, 3H) | N-(2-((6-(2,6-dichloro-3,5-dimethoxyphenyl)imidazo[1',2':1,6]pyrido[2,3-d]pyrimidin-2-yl)amino)-3-methyl-5-morpholinophenyl)acrylamide | 634.2 |
| 64 | 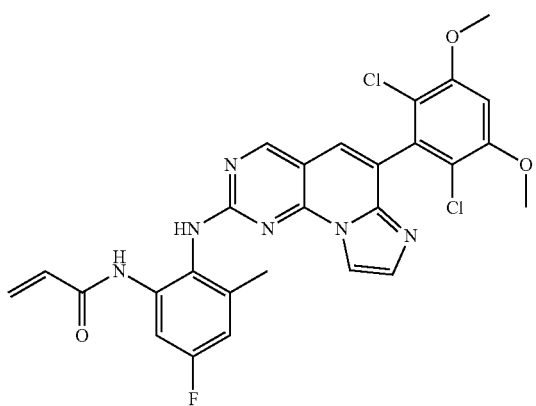 [SMILES: C=CC(=O)Nc1cc(F)cc(C)c1Nc1ncc2cc(-c3c(Cl)c(OC)cc(OC)c3Cl)c3nccn3c2n1] (DMSO-d$_6$): δ 9.49 (s, 1H), 9.24 (s, 1H), 8.99 (s, 1H), 8.31 (s, 1H), 7.78 (m, 1H), 7.50 (m, 2H), 7.06-7.01 (m, 2H), 6.56 (m, 1H), 6.20 (m, 1H), 5.66 (m, 1H), 3.98 (s, 6H), 2.20 (s, 3H) | N-(2-((6-(2,6-dichloro-3,5-dimethoxyphenyl)imidazo[1',2':1,6]pyrido[2,3-d]pyrimidin-2-yl)amino)-5-fluoro-3-methylphenyl)acrylamide | 567.1 |
| 65 | 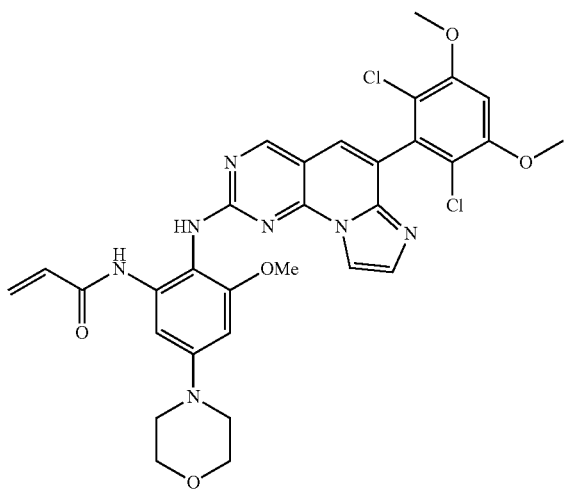 [SMILES: C=CC(=O)Nc1cc(N2CCOCC2)cc(OC)c1Nc1ncc2cc(-c3c(Cl)c(OC)cc(OC)c3Cl)c3nccn3c2n1] (CDCl$_3$) δ 8.91 (s, 1H), 8.63 (brs, 1H), 8.10 (s, 1H), 7.61 (brs, 1H), 7.53 (s, 1 H), 7.26 (m, 2H), 6.95 (brs, 1H), 6.89 (s, 1H), 6.34 (m, 1H), 6.19 (m, 1H), 5.45 (d, 1H), 3.97 (s, 6H), 3.89 (m, 4H), 3.82 (s, 3H), 3.27 (m, 4H). | N-(2-((6-(2,6-dichloro-3,5-dimethoxyphenyl)imidazo[1',2':1,6]pyrido[2,3-d]pyrimidin-2-yl)amino)-3-methoxy-5-morpholinophenyl)acrylamide | 650.1 |

| 66 | 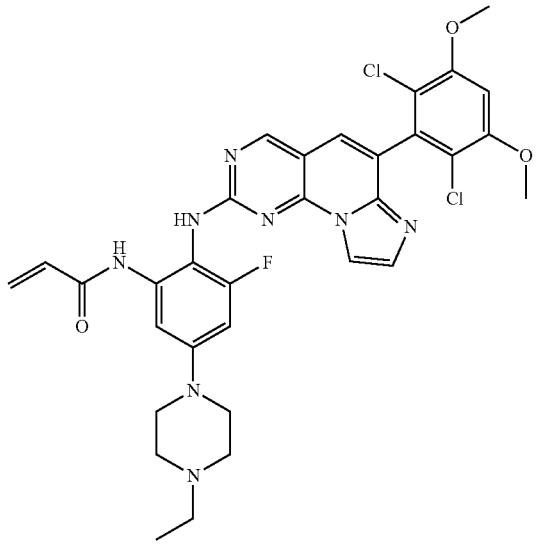 [SMILES: C=CC(=O)Nc1cc(N2CCN(CC)CC2)cc(F)c1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-(4-ethylpiperazin-1-yl)-3-fluorophenyl)acrylamide | 665.2 |
(DMSO-d$_6$) δ 9.56 (s, 1H), 9.11 (m, 2H), 8.30 (s, 1H), 7.84 (s, 1H), 7.50 (m, 2H), 7.06 (s, 1H), 6.75 (s, 1H), 6.55 (s, 1H), 6.25-6.19 (d, 1H), 5.71-5.70 (d, 1H), 3.98 (s, 6H), 3.19 (t, 4H), 2.50 (t, 4H), 2.42-2.35 (q, 2H), 1.09-1.02 (t, 3H)
| 67 | 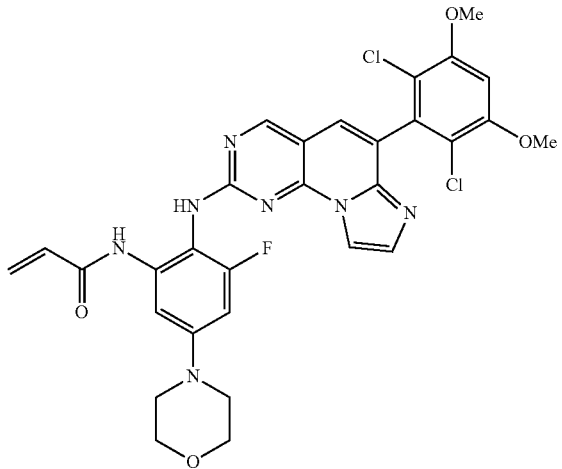 [SMILES: C=CC(=O)Nc1cc(N2CCOCC2)cc(F)c1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-3-fluoro-5-morpholinophenyl)acrylamide | 638.1 |
(CDCl$_3$): δ 8.92 (s, 1H), 8.17 (s, 1H), 7.57 (s, 1H), 6.69 (s, 1H), 6.43 (d, 1H), 6.24 (m 1H), 6.16 (dd, 1H), 5.73 (dd, 1H) 3.97 (s, 6H), 3.87 (t, 4H), 3.18 (t, 4H)

-continued

| | | | |
|---|---|---|---|
| 68 | 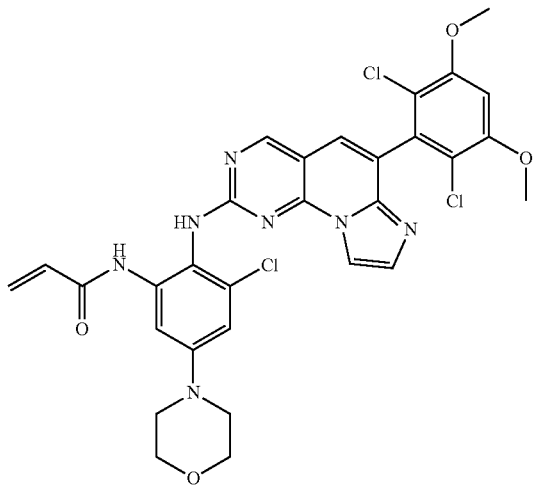 [SMILES: C=CC(=O)Nc1cc(N2CCOCC2)cc(Cl)c1Nc1ncc2cc(-c3c(Cl)c(OC)cc(OC)c3Cl)c3nccn3c2n1] | N-(3-chloro-2-((6-(2,6-dichloro-3,5-dimethoxyphenyl)imidazo[1',2':1,6]pyrido[2,3-d]pyrimidin-2-yl)amino)-5-morpholinophenyl)acrylamide | 654.1 |

(DMSO-$d_6$) δ 9.76-9.46 (d, 1H), 9.24-9.15 (d, 1H), 8.98 (s, 1H), 8.32 (s, 1H), 7.77 (s, 1H), 7.56-7.42 (m, 2H), 7.06 (s, 1H), 6.99-6.93 (d, 1H), 6.56 (m, 1H), 6.25-6.20 (m, 1H), 5.68 (m, 1H), 3.99 (s, 6H), 3.76 (m, 4H), 3.17 (m, 3H)

| | | | |
|---|---|---|---|
| 69 | 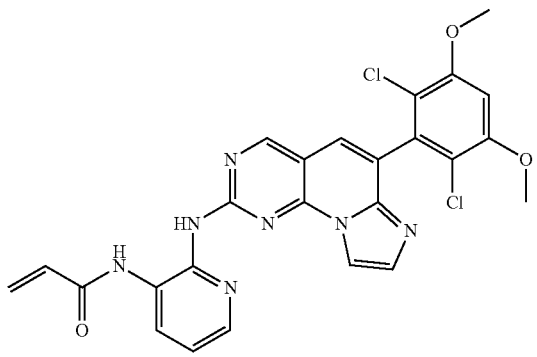 [SMILES: C=CC(=O)Nc1cccnc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)pyridin-3-yl)acrylamide | 535.1 |

(DMSO-$d_6$) δ 9.84 (s, 1H), 9.11 (s, 1H), 8.13 (s, 1H), 7.87 (m, 1H), 7.69 (m, 2H) 7.18 (m, 1H), 7.00 (m, 2H), 6.70 (s, 1H), 6.40 (m 1H), 6.20 (m 1H), 5.71 (dd, 1H), 3.99 (s, 6H)

| | | | |
|---|---|---|---|
| 70 | 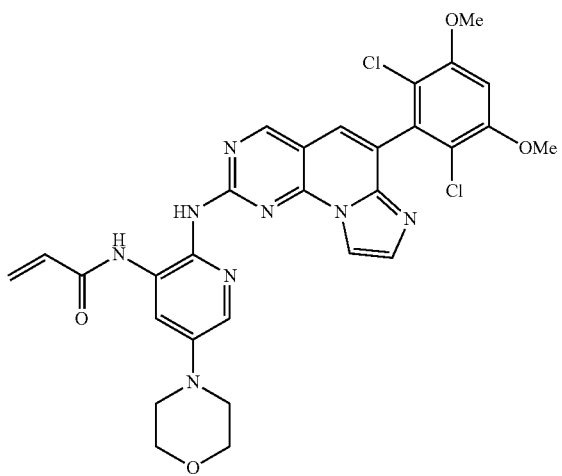 [SMILES: C=CC(=O)Nc1cc(N2CCOCC2)cnc1Nc1ncc2cc(-c3c(Cl)c(OC)cc(OC)c3Cl)c3nccn3c2n1] | N-(2-((6-(2,6-dichloro-3,5-dimethoxyphenyl)imidazo[1',2':1,6]pyrido[2,3-d]pyrimidin-2-yl)amino)-5-morpholinopyridin-3-yl)acrylamide | 621.2 |

(CDCl$_3$) δ 9.28 (s, 1H), 8.98 (s, 1H), 8.27 (s, 1H), 8.10 (m, 2H), 7.56 (s, 1H), 7.32 (s, 1H), 6.70 (s, 1H), 6.40 (m 1H), 6.20 (m 1H), 5.71 (dd, 1H), 3.98 (s, 6H), 3.92 (t, 4H), 3.29 (t, 4H)

| 71 | 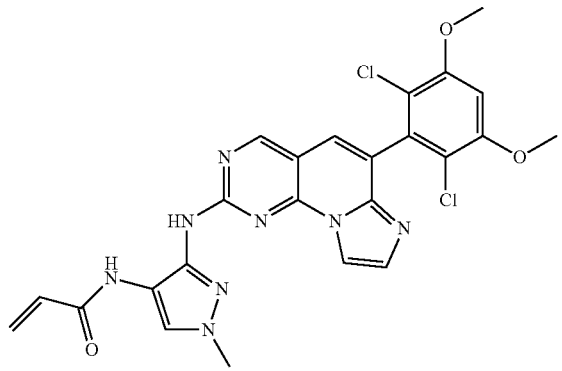 [SMILES: C=CC(=O)Nc1cn(C)nc1Nc1ncc2cc(-c3c(Cl)c(OC)cc(OC)c3Cl)c3nccn3c2n1] | N-(3-((6-(2,6-dichloro-3,5-dimethoxyphenyl)imidazo[1',2':1,6]pyrido[2,3-d]pyrimidin-2-yl)amino)-1-methyl-1H-pyrazol-4-yl)acrylamide | 539.1 |
|---|---|---|---|

(DMSO-d$_6$) δ 9.45 (s, 1H), 9.40 (s, 1H), 9.08 (s, 1H), 8.19 (s, 1H), 7.98 (m, 1H), 7.50 (m, 2H), 7.04 (m, 1H), 6.48 (m, 1H), 6.16 (m, 1H), 5.54 (m, 1H), 3.97 (s, 6H), 3.79 (s, 3H)

[Example 72] N-(2-((6-(2,6-difluoro-3,5-dimethoxyphenyl)imidazo[1',2':1,6]pyrido[2,3-d]pyrimidin-2-yl)amino)-3-fluorophenyl)acrylamide [Compound 72]

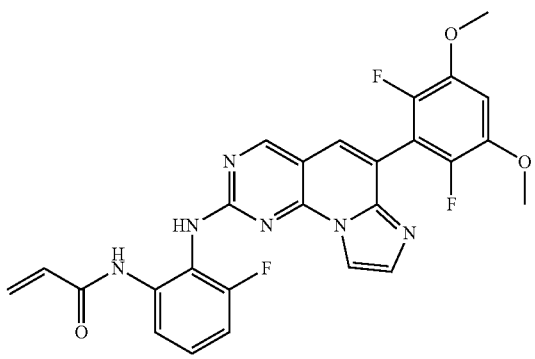 [SMILES: C=CC(=O)Nc1cccc(F)c1Nc1ncc2cc(-c3c(F)c(OC)cc(OC)c3F)c3nccn3c2n1]

Step 1. Preparation of 6-(2,6-difluoro-3,5-dimethoxyphenyl)-2-(methylthio)pyrido[2,3-d]pyrimidine-7-amine

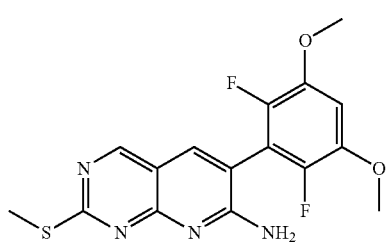

To a solution of 2-(2,6-difluoro-3,5-dimethoxyphenyl) acetonitrile (5.26 g, 24.6 mmol) in N,N-dimethylformamide was added 60% NaH (1.5 mg, 33.69 mmol). The mixture was stirred at room temperature for 1 hour. 4-amino-2-(methylsulfanyl)-5-pyrimidinecarbaldehyde (3.8 g, 22.4 mmol) was added, and then stirred for overnight. Water was added. The precipitate was filtered to obtain a target compound (6.4 g).

Step 2. Preparation of 6-(2,6-difluoro-3,5-dimethoxyphenyl)-2-(methylthio)imidazo[1',2':1,6]pyrido[2,3-d]pyrimidine

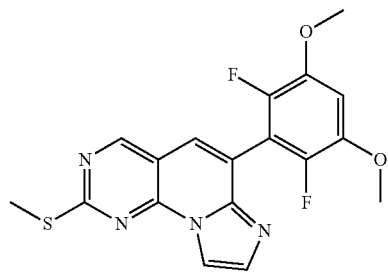

A target compound (4.5 g) was obtained by the synthesis method of [Step 2] of [Example 1] using the 6-(2,6-difluoro-3,5-dimethoxyphenyl)-2-(methylthio)pyrido[2,3-d]pyrimidine-7-amine (6.4 g) synthesized in [Step 1].

Step 3. Preparation of 6-(2,6-difluoro-3,5-dimethoxyphenyl)-2-(methylsulfonyl)imidazo[1',2':1,6]pyrido[2,3-d]pyrimidine

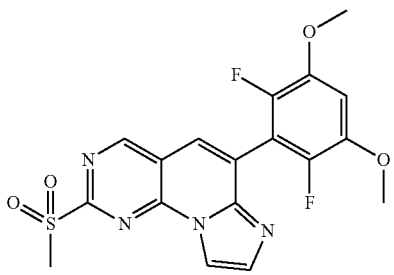 [SMILES: COc1cc(OC)c(F)c(-c2cc3cnc(S(C)(=O)=O)nc3n3ccnc23)c1F]

A target compound (0.74 g) was obtained by the synthesis method of [Step 4] of [Example 1] using the 6-(2,6-difluoro-3,5-dimethoxyphenyl)-2-(methylthio)pyrido[2,3-d]pyrimidine-7-amine (1.0 g, 2.57) synthesized in [Step 2].

Step 5. Preparation of N1-(6-(2,6-difluoro-3,5-dimethoxyphenyl)imidazo[1',2':1,6]pyrido[2,3-d]pyrimidin-2-yl)-6-fluorobenzene-1,2-diamine

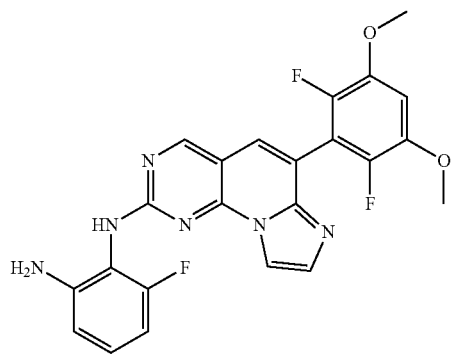 [SMILES: COc1cc(OC)c(F)c(-c2cc3cnc(Nc4c(N)cccc4F)nc3n3ccnc23)c1F]

6-(2,6-difluoro-3,5-dimethoxyphenyl)-N-(2-fluoro-6-nitrophenyl)imidazo[1',2':1,6]pyrido[2,3-d]pyrimidine-2-amine was obtained by the synthesis method of [Step 1] of [Example 5] using the 6-(2,6-difluoro-3,5-dimethoxyphenyl)-2-(methylsulfonyl)imidazo[1',2':1,6]pyrido[2,3-d]pyrimidine (100 mg, 0.023 mmol) synthesized in [Step 3] and 2-fluoro-6-nitrophenylaniline (56 mg, 0.035 mmol). Using this compound, a target compound (80 mg) was obtained by the synthesis method of [Step 6] of [Example 1].

Step 6. Preparation of N-(2-((6-(2,6-difluoro-3,5-dimethoxyphenyl)imidazo[1',2':1,6]pyrido[2,3-d]pyrimidin-2-yl)amino)-3-fluorophenyl)acrylamide

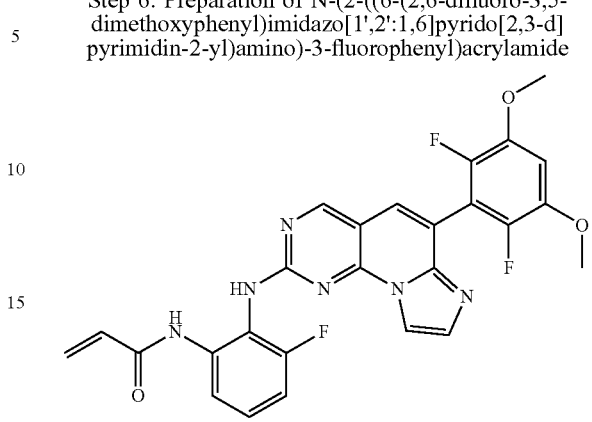

A target compound (40 mg) was obtained by the synthesis method of [Step 7] of [Example 1] using the N1-(6-(2,6-difluoro-3,5-dimethoxyphenyl)imidazo[1',2':1,6]pyrido[2,3-d]pyrimidin-2-yl)-6-fluorobenzene-1,2-diamine (80 mg, 0.17 mmol) synthesized in [Step 5].

| 72 | 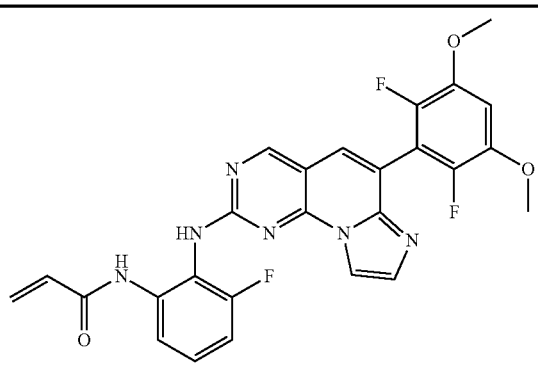 | N-(2-((6-(2,6-difluoro-3,5-dimethoxyphenyl)imidazo[1',2':1,6]pyrido[2,3-d]pyrimidin-2-yl)amino)-3-fluorophenyl)acrylamide | 521.2 |

(DMSO-d$_6$)δ 9.73 (brs, 1H), 9.45 (brs, 1H), 9.11 (s, 1H), 8.31 (d, 1H), 7.71 (s, 1H), 7.54 (brs, 1H), 7.36 (m, 1H), 7.17 (m, 2H), 6.92-6.89 (d, 1H), 6.53-6.44 (q, 1H), 6.26-6.20 (dd, 1H), 5.72-5.68 (d, 1H), 3.99 (s, 6H)

| 73 | 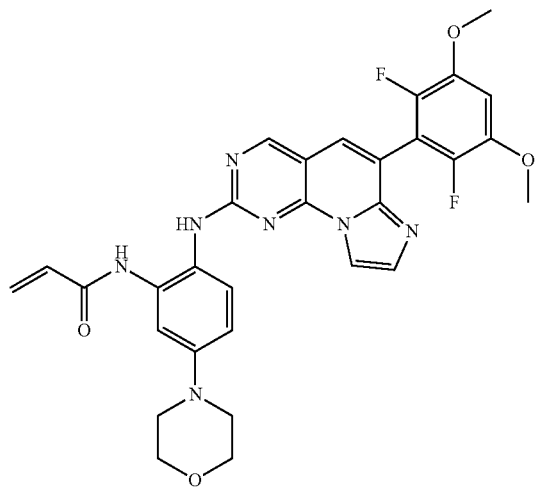 [SMILES: C=CC(=O)Nc1cc(N2CCOCC2)ccc1Nc1ncc2cc(-c3c(F)c(OC)cc(OC)c3F)c3nccn3c2n1] | N-(2-((6-(2,6-difluoro-3,5-dimethoxyphenyl)imidazo[1',2':1,6]pyrido[2,3-d]pyrimidin-2-yl)amino)-5-morpholinophenyl)acrylamide | 588.2 |

(DMSO-d$_6$)δ 9.72 (brs, 1H), 9.33 (brs, 1H), 9.09 (s, 1H), 8.13 (s, 1H), 7.68 (s, 1H), 7.62 (brs, 2H), 7.54 (s, 1H), 7.31 (s, 1H), 7.17-7.11 (t, 1H), 6.92-6.89 (d, 1H), 6.53-6.44 (q, 1H), 6.26-6.20 (dd, 1H), 5.72-5.68 (d, 1H), 3.93 (s, 6H), 3.78-3.75 (t, 4H), 3.17-3.13 (t, 4H)

| | | | |
|---|---|---|---|
| 74 | 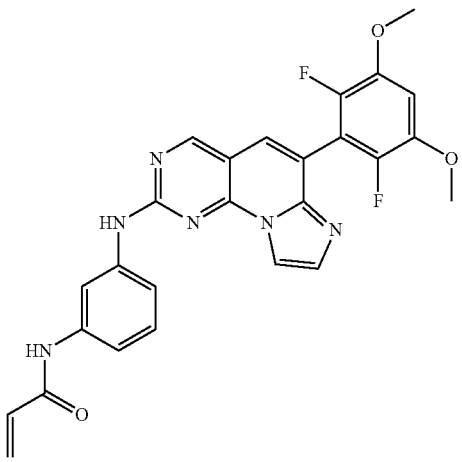 [SMILES: C=CC(=O)Nc1cccc(Nc2ncc3cc(-c4c(F)c(OC)cc(OC)c4F)c4nccn4c3n2)c1] (DMSO-d₆) δ 10.49 (s, 1H), 10.23 (s, 1 H), 9.21 (s, 1H), 8.90 (1H), 8.90 (m, 2H), 7.94-7.64 (m, 2H), 7.40-7.13 (m, 3H), 6.51-6.32 (m, 3H), 5.80 (m, 1H), 3.93 (s, 6H) | N-(3-((6-(2,6-difluoro-3,5-dimethoxyphenyl)imidazo[1',2':1,6]pyrido[2,3-d]pyrimidin-2-yl)amino)phenyl)acrylamide | 503.2 |
| 75 | 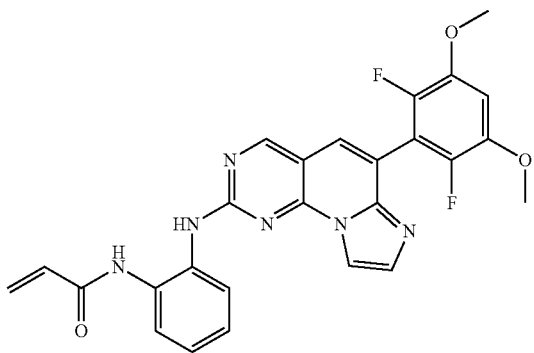 [SMILES: C=CC(=O)Nc1ccccc1Nc1ncc2cc(-c3c(F)c(OC)cc(OC)c3F)c3nccn3c2n1] (DMSO-d₆) δ 9.81 (s, 1H), 9.55 (s, 1H), 9.14 (s, 1H), 8.17 (1H), 7.86 (d, 1H), 7.70 (m, 2H), 7.56 (s, 1H), 7.31-7.12 (m, 3H), 6.53 (dd, 1H), 5.72 (dd, 1H) 3.96(s, 6H) | N-(2-((6-(2,6-difluoro-3,5-dimethoxyphenyl)imidazo[1',2':1,6]pyrido[2,3-d]pyrimidin-2-yl)amino)phenyl)acrylamide | 503.2 |
| 76 | 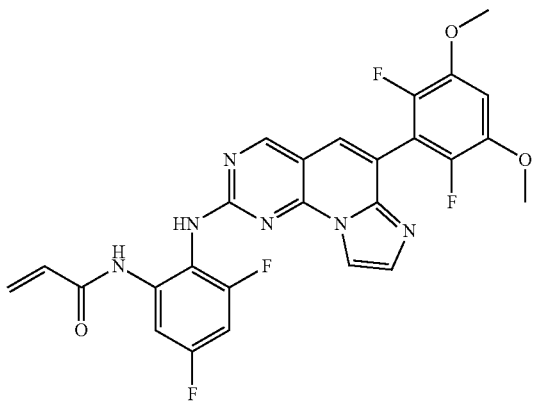 [SMILES: C=CC(=O)Nc1cc(F)cc(F)c1Nc1ncc2cc(-c3c(F)c(OC)cc(OC)c3F)c3nccn3c2n1] (DMSO-d₆) δ 10.07 (s, 1H), 10.02 (s, 1H), 9.19 (s, 1H), 8.55 (s, 1H), 7.73 (s, 1H), 7.59 (s, 1H), 7.50 (t, 1H), 7.15 (t, 1H), 6.63 (dd, 1H), 6.33 (dd, 1H), 5.81 (d, 1H), 3.93 (s, 6H) | N-(2-((6-(2,6-difluoro-3,5-dimethoxyphenyl)imidazo[1',2':1,6]pyrido[2,3-d]pyrimidin-2-yl)amino)-3,5-difluorophenyl)acrylamide | 539.1 |

| 77 | 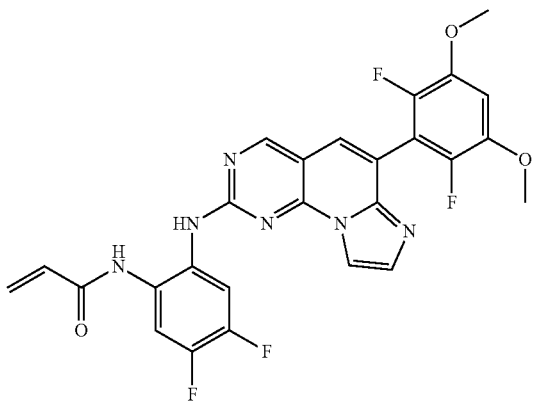 [SMILES: C=CC(=O)Nc1cc(F)c(F)cc1Nc1ncc2cc(-c3c(F)c(OC)cc(OC)c3F)c3nccn3c2n1] (DMSO-d$_6$) δ 9.83 (s, 1H), 9.71 (s, 1H), 9.18 (s, 1H), 8.17 (s, 1H), 7.93-7.77 (m, 2H), 7.74 (s, 1H), 7.57 (s, 1H), 7.15 (t, 1H), 6.49 (dd, 1H), 6.28 (ss, 1H), 5.71 (dd, 1H), 3.93 (s, 6H) | N-(2-((6-(2,6-difluoro-3,5-dimethoxyphenyl)imidazo[1',2':1,6]pyrido[2,3-d]pyrimidin-2-yl)amino)-4,5-difluorophenyl)acrylamide | 539.1 |
|---|---|---|---|
| 78 | 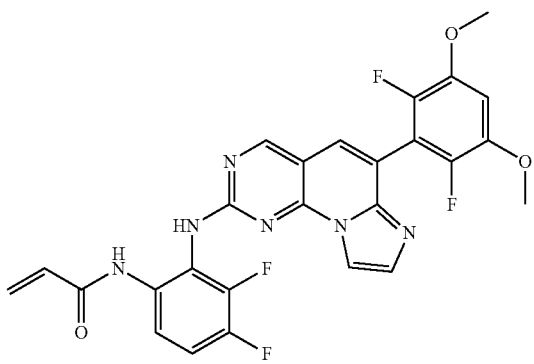 [SMILES: C=CC(=O)Nc1ccc(F)c(F)c1Nc1ncc2cc(-c3c(F)c(OC)cc(OC)c3F)c3nccn3c2n1] (DMSO-d$_6$): δ 9.65-9.46 (m, 1H), 9.15 (s, 1H), 8.31 (s, 1H), 7.73 (s, 2H), 7.56 (s, 1H), 7.48-7.38 (m, 1H), 7.15 (t, 1H), 6.56-6.41 (m, 1H), 6.22 (d, 1H), 5.72 (t, 1H), 3.93 (s, 6H) | N-(2-((6-(2,6-difluoro-3,5-dimethoxyphenyl)imidazo[1',2':1,6]pyrido[2,3-d]pyrimidin-2-yl)amino)-3,4-difluorophenyl)acrylamide | 539.1 |
| 79 | 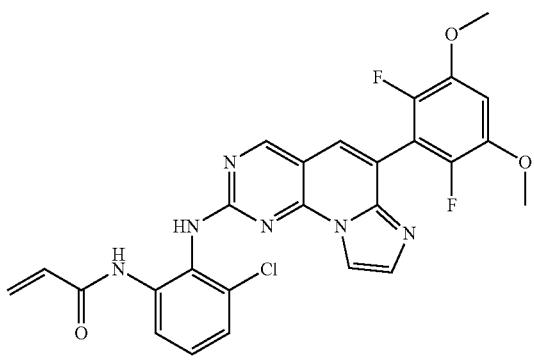 (DMSO-d$_6$) δ 9.63 (s, 1H), 9.56 (s, 1H), 9.09 (s, 1H), 7.71 (s, 1H), 7.44 (s, 1H), 7.36 (t, 2H), 7.14 (t, 1H), 6.55 (dd, 1H), 6.21 (d, 1H), 5.68 (d, 1H), 3.93 (s, 6H) | N-(3-chloro-2-((6-(2,6-difluoro-3,5-dimethoxyphenyl)imidazo[1',2':1,6]pyrido[2,3-d]pyrimidin-2-yl)amino)phenyl)acrylamide | 537.1 |

[Example 80] 4-(3-(6-(2,6-dichloro-3,5-dimethoxyphenyl)imidazo[1',2':1,6]pyrido[2,3-d]pyrimidin-2-yl)phenyl)morpholine [Compound 80]

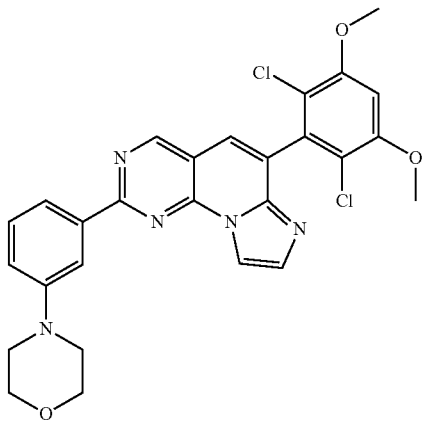 [SMILES: COc1cc(OC)c(Cl)c(-c2cc3cnc(-c4cccc(N5CCOCC5)c4)nc3n3ccnc23)c1Cl]

Step 1. Preparation of 2-chloro-6-(2,6-dichloro-3,5-dimethoxyphenyl)imidazo[1',2':1,6]pyrido[2,3-d]pyrimidine

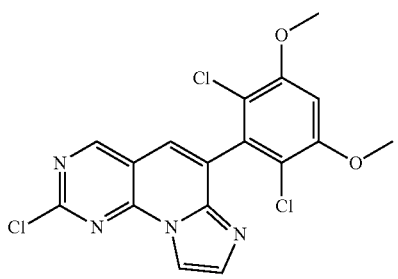 [SMILES: COc1cc(OC)c(Cl)c(-c2cc3cnc(Cl)nc3n3ccnc23)c1Cl]

The 6-(2,6-dichloro-3,5-dimethoxyphenyl)-2-(methylsulfonyl)imidazo[1',2':1,6]pyrido[2,3-d]pyrimidine (2 g, 4.31 mmol) synthesized in [Step 4] of [Example 1] was dissolved in tetrahydrofuran/water (30 ml:30 ml). Potassium hydroxide (726 mg, 12.9 mmol) was added, and the mixture was stirred for 3 hours at room temperature. The pH of the mixture was adjusted to about 2 with 6 N hydrochloric acid, the precipitate was filtered to obtain 6-(2,6-dichloro-3,5-dimethoxyphenyl)imidazo[1',2':1,6]pyrido[2,3-d]pyrimidin-2-ol. Acetonitrile (50 ml) and then POCl₃ (5.7 ml, 61.3 mmol) were added, and the mixture was stirred under reflux for 3 hours. After cooling to room temperature, methanol/water (10 ml/20 ml) was added, the precipitate was filtered, and then recrystallized with acetone to obtain a target compound (1.2 g).

Step 2. Preparation of 4-(3-(6-(2,6-dichloro-3,5-dimethoxyphenyl)imidazo[1',2':1,6]pyrido[2,3-d]pyrimidin-2-yl)phenyl)morpholine

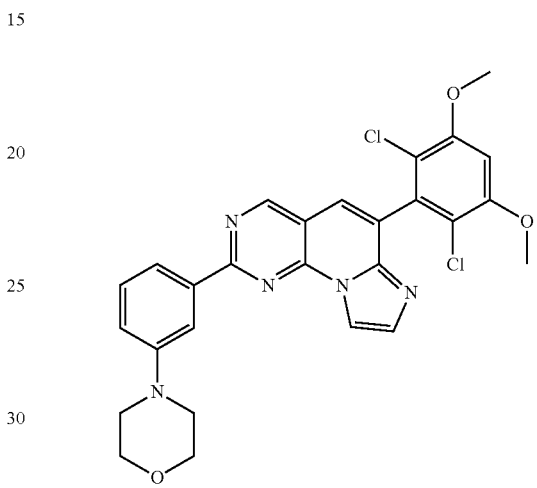

The 2-chloro-6-(2,6-dichloro-3,5-dimethoxyphenyl)imidazo[1',2':1,6]pyrido[2,3-d]pyrimidine (100 mg, 0.244 mmol) synthesized in [Step 1], 4-(3-(4,4,5,5-tetramethyl-1,3,2-dioxaborolan-2-yl)phenyl)morpholine (141 mg, 0.488 mmol) and Pd(dppf)Cl₂ (10 mg, 0.012 mmol) were taken up in t-butanol/water (3 ml/3 ml). Sodium carbonate (78 mg, 0.732 mmol) was added. The mixture was heated to 90 □, and stirred for 3 hours. When the reaction was completed, the mixture was extracted with dichloromethane and saturated ammonium chloride. The organic layer was dried over sodium sulfate, filtered and concentrated under vacuum. The crude material was purified by Chromatography to give the target compound (67 mg) as solid.

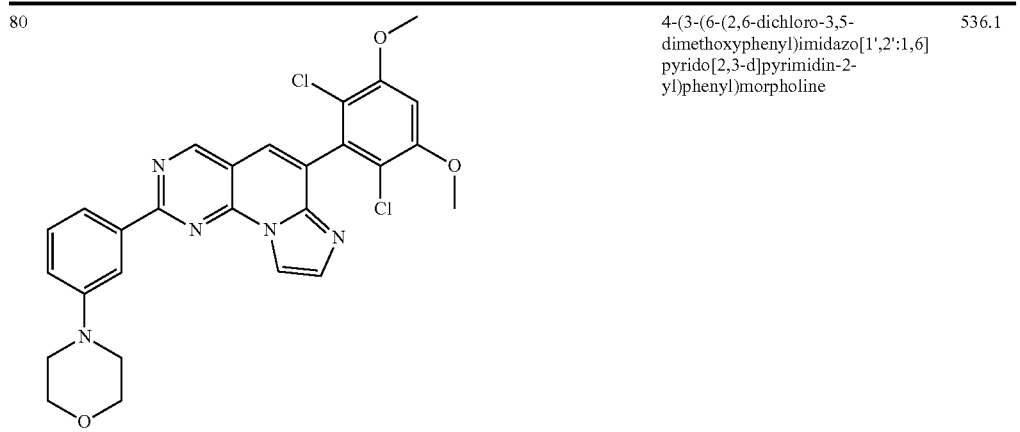

| 80 | | 4-(3-(6-(2,6-dichloro-3,5-dimethoxyphenyl)imidazo[1',2':1,6]pyrido[2,3-d]pyrimidin-2-yl)phenyl)morpholine | 536.1 |

(CDCl₃)δ 9.60 (s, 1H), 8.87 (s, 1H), 8.23 (s, 1H), 8.16-8.13 (d, 1H), 7.77 (s, 1H), 7.68 (s, 1H), 7.50-7.45 (t, 1H), 7.23-7.21 (d, 1H), 7.10 (s, 1H), 4.01 (s, 6H), 3.81 (t, 4H), 3.27 (t, 4H)

| | | | |
|---|---|---|---|
| 81 | 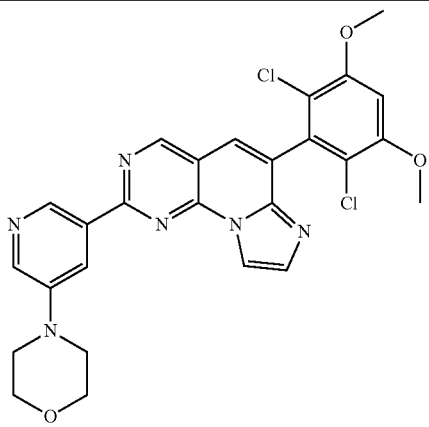 | 4-(5-(6-(2,6-dichloro-3,5-dimethoxyphenyl)imidazo[1',2':1,6]pyrido[2,3-d]pyrimidin-2-yl)pyridin-3-yl)morpholine | 537.1 |
| | (CDCl₃): δ 9.64 (s, 1H), 9.27 (d, 1H), 8.96 (d, 1H), 8.55 (d, 1H), 8.41 (s, 1H), 7.80 (s, 1H), 7.70 (d, 1H), 7.11 (s, 1H), 4.01 (s, 6H), 3.84-3.81 (t, 4H), 3.42-3.39 (t, 4H) | | |
| 82 | 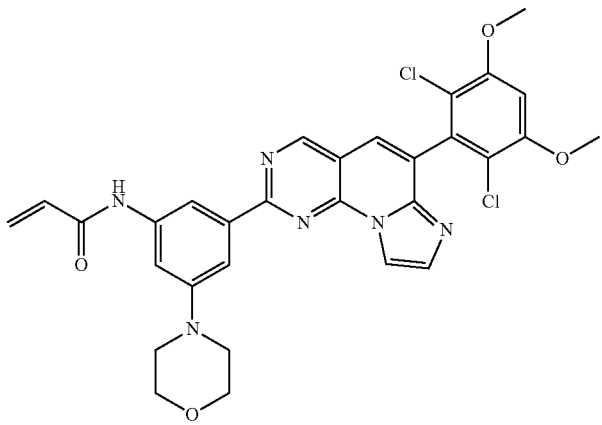 [SMILES: C=CC(=O)Nc1cc(-c2ncc3cc(-c4c(Cl)c(OC)cc(OC)c4Cl)c4nccn4c3n2)cc(N2CCOCC2)c1] | N-(3-(6-(2,6-dichloro-3,5-dimethoxyphenyl)imidazo[1',2':1,6]pyrido[2,3-d]pyrimidin-2-yl)-5-morpholinophenyl)acrylamide | 643.1 |
| | (CDCl₃)δ 9.27 (s, 1H), 8.54 (s, 2H), 7.98 (m, 3H), 7.68 (m, 1H), 7.42 (s, 1H), 6.69 (s, 1H), 6.45 (m, 1H), 6.24 (m, 1H), 5.78 (d, 1H), 3.96 (s, 6H), 3.88 (m, 4H), 3.36 (m, 4H) | | |

[Example 83] N-(2-((4-(2,6-dichloro-3,5-dimethoxyphenyl)imidazo[1,2-a][1,6]naphthyridin-8-yl)amino)-5-morpholinophenyl)acrylamide [Compound 83]

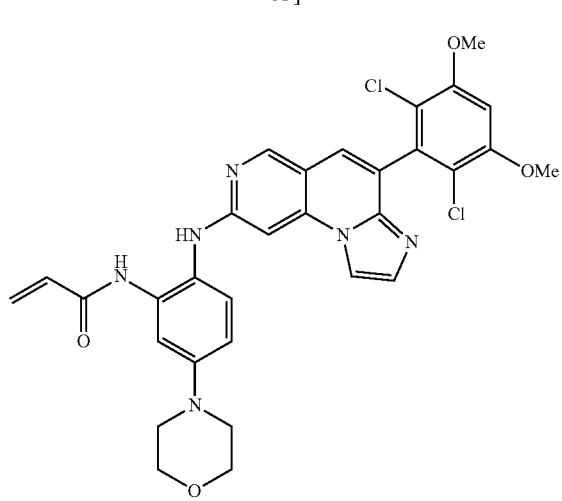

Step 1. Preparation of 7-chloro-3-(3,5-dimethoxyphenyl)-1,6-naphthyridine-2-amine

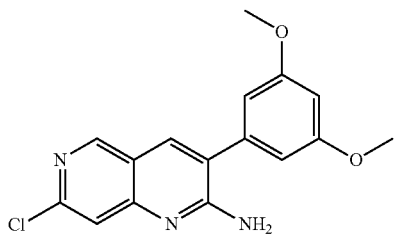 [SMILES: COc1cc(OC)cc(-c2cc3cnc(Cl)cc3nc2N)c1]

To a solution of 3,5-dimethoxyphenylacetonitrile (1.24 g, 7.03 mmol, ARK Pharm) in tetrahydrofuran (25 ml) was added 60% NaH (0.38 g, 7.7 mmol). The mixture was stirred at room temperature for 1 hour. 4-amino-6-chloronicotinic aldehyde (1.0 g, 6.4 mmol, ARK Phram) was added. The mixture was stirred at room temperature for 6 hours. The mixture was concentrated under vacuum. The residue was dissolved in dichloromethane and washed with saturated ammonium chloride. The organic layer was dried over sodium sulfate, filtered and concentrated under vacuum to give a target compound (1.56 g).

Step 2. Preparation of 2-chloro-6-(3,5-dimethoxyphenyl)imidazo[1',2':1,6]pyrido[2,3-d]pyrimidine

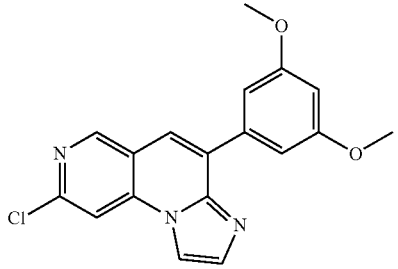 [SMILES: COc1cc(OC)cc(-c2cc3cnc(Cl)cc3n3ccnc23)c1]

To a mixture of 7-chloro-3-(3,5-dimethoxyphenyl)-1,6-naphthyridine-2-amine (1.56 g, 4.9 mmol) synthesized in [Step 1] and trimethylamine (4.13 ml, 29.6 mmol) in acetonitrile/water (50 ml/50 ml) was added 1,2-dichloroethyl ethyl (2.4 ml, 19.8 mmol) over 30 minutes. The mixture was refluxed for overnight. After cooling to room temperature, water (45 ml) was added. The precipitate was filtered to obtain a target compound (0.92 g).

Step 3. Preparation of 8-chloro-4-(2,6-dichloro-3,5-dimethoxyphenyl)imidazo[1,2-a][1,6]naphthyridine

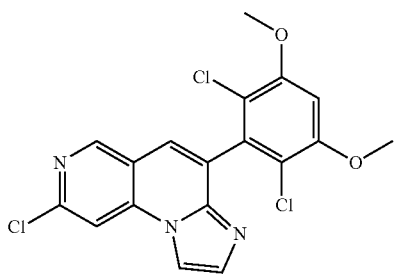 [SMILES: COc1cc(OC)c(Cl)c(-c2cc3cnc(Cl)cc3n3ccnc23)c1Cl]

The 2-chloro-6-(3,5-dimethoxyphenyl)imidazo[1',2':1,6]pyrido[2,3-d]pyrimidine (930 mg, 2.7 mmol) synthesized in [Step 2] in [Step 2] was dissolved in dichloromethane (30 ml). Sulfuryl chloride ($SO_2Cl_2$, 730 mg, 5.4 mmol) was added dropwise at −20 □., and then stirred for 30 minutes. When the reaction was completed, a small quantity of methanol was added thereto, and the reaction mixture was concentrated under vacuum. The residue was titrated in ethyl acetate (30 ml) for 30 minutes and then filtered to obtain a target compound (900 mg).

Step 4. Preparation of N1-(4-(2,6-dichloro-3,5-dimethoxyphenyl)imidazo[1,2-a][1,6]naphthyridin-8-yl)-4-morpholinobenzene-1,2-diamine

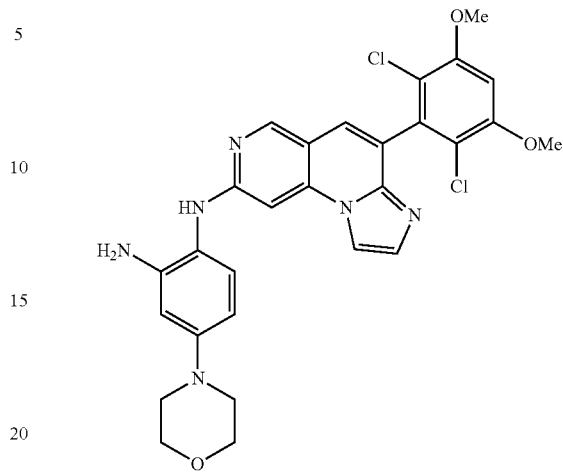

The 8-chloro-4-(2,6-dichloro-3,5-dimethoxyphenyl)imidazo[1,2-a][1,6]naphthyridine (100 mg, 0.24 mmol) synthesized in [Step 3] and 4-morpholino-2-nitroaniline (55 mg, 0.24 mmol) were taken up in 1,4-dioxane (4 ml). $Pd(OAc)_2$ (5.4 mg, 0.024 mmol), Xantphos (23 mg, 0.048 mmol) and $Cs_2CO_3$ (156 mg, 0.48 mmol) were added. The mixture was stirred for 3 hours at 100 □ under argon atmospheric condition. After cooling to room temperature, the mixture was filtered using a celite, and ethyl acetate was added. The solution was washed with water and brine, then dried over magnesium sulfate and filtered, and the filtrate was concentrated under vacuum. The residue was purified by chromatography to give 4-(2,6-dichloro-3,5-dimethoxyphenyl)-N-(4-morpholino-2-nitrophenyl)imidazo[1,2-a][1,6]naphthyridine-8-amine (120 mg). Using this compound, a target compound (60 mg) was obtained by the synthesis method of [Step 6] of [Example 1].

Step 5. Preparation of N-(2-((4-(2,6-dichloro-3,5-dimethoxyphenyl)imidazo[1,2-a][1,6]naphthyridin-8-yl)amino)-5-morpholinophenyl)acrylamide

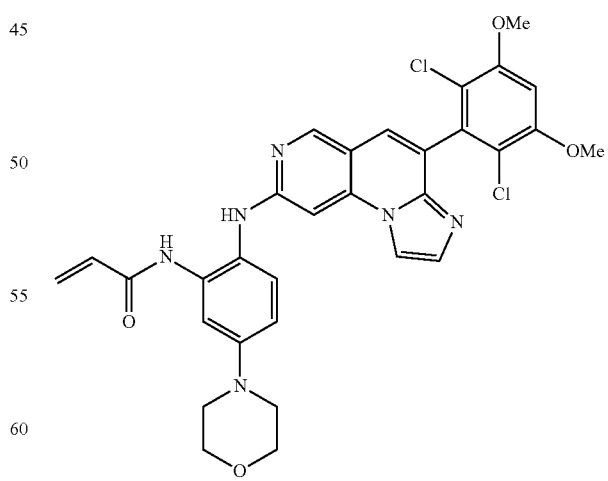

A target compound (20 mg) was obtained by the synthesis method of [Step 7] of [Example 1] using the N1-(4-(2,6-dichloro-3,5-dimethoxyphenyl)imidazo[1,2-a][1,6]naphthyridin-8-yl)-4-morpholinobenzene-1,2-diamine (60 mg, 0.11 mmol) synthesized in [Step 4].

| 83 | 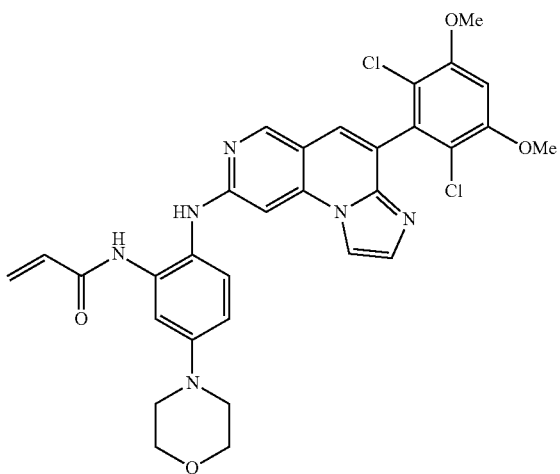 | N-(2-((4-(2,6-dichloro-3,5-dimethoxyphenyl)imidazo[1,2-a][1,6]naphthyridin-8-yl)amino)-5-morpholinophenyl)acrylamide | 619.2 |
(DMSO-$d_6$) δ 9.75 (s, 1H), 8.76 (s, 1H), 8.48 (brs, 1H), 8.26 (s, 1H), 7.42 (m, 3H), 7.28 (s, 1H), 7.03 (d, 2H), 6.87 (m, 1H), 6.23 (m, 1H), 6.16 (m, 1H), 5.65 (m, 1H), 3.96 (s, 6H), 3.78 (m, 4H), 3.22 (m, 4H)
| 84 | 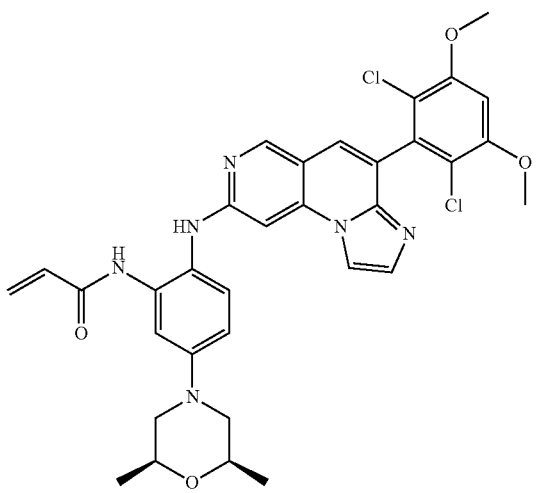 [SMILES: C=CC(=O)Nc1cc(N2C[C@@H](C)O[C@@H](C)C2)ccc1Nc1cc2c(cn1)cc(-c1c(Cl)c(OC)cc(OC)c1Cl)c1nccn12] | N-(2-((4-(2,6-dichloro-3,5-dimethoxyphenyl)imidazo[1,2-a][1,6]naphthyridin-8-yl)amino)-5-((2S,6R)-2,6-dimethylmorpholino)phenyl)acrylamide | 647.2 |
(DMSO-$d_6$) δ 9.80 (brs, 1H), 8.77 (s, 1H), 8.52 (brs, 1H), 8.26 (s, 1H), 7.46-7.42 (m, 2H), 7.29 (s, 1H), 7.07-7.04 (m, 2H), 6.90-6.87 (d, 1H), 6.53-6.44 (m, 1H), 6.24-6.19 (d, 1H), 5.70-5.67 (d, 1H), 3.98 (s, 6H), 3.72 (m, 2H), 3.57-3.54 (m, 2H), 2.33-2.25 (t, 2H), 1.19-1.17 (d, 6H)

| 85 | 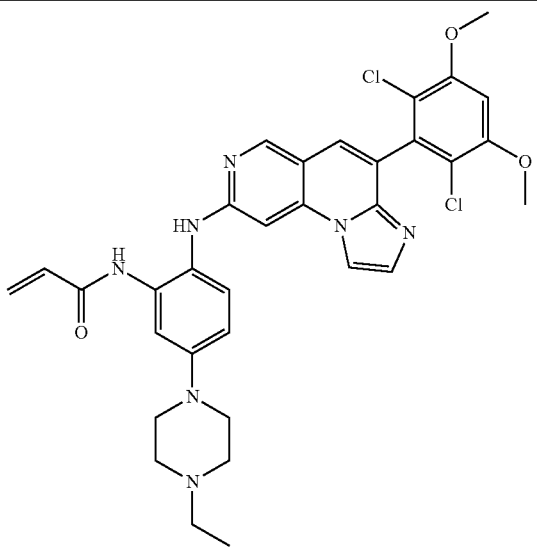 | N-(2-((4-(2,6-dichloro-3,5-dimethoxyphenyl)imidazo[1,2-a][1,6]naphthyridin-8-yl)amino)-5-(4-ethylpiperazin-1-yl)phenyl)acrylamide | 646.2 |

(DMSO-d$_6$) δ 9.74 (s, 1H), 8.77 (s, 1H), 8.44 (s, 1H), 8.27 (s, 1H), 7.46-7.39 (m, 3H), 7.27 (s, 1H), 7.04 (s, 2H), 6.89-6.85 (dd, 1H), 6.51-6.42 (m, 1H), 6.24-6.18 (d, 1H), 5.71-5.67 (d, 1H), 3.98 (s, 6H), 3.17-3.16 (m, 4H), 2.50 (m, 4H), 2.42-2.35 (q, 2H), 1.07-1.02 (t, 3H)

| 86 | 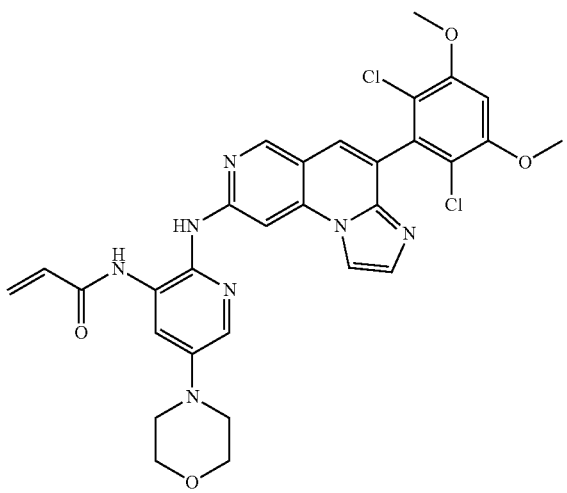 [SMILES: C=CC(=O)Nc1cc(N2CCOCC2)cnc1Nc1cc2c(cn1)cc(-c1c(Cl)c(OC)cc(OC)c1Cl)c1nccn12] | N-(2-((4-(2,6-dichloro-3,5-dimethoxyphenyl)imidazo[1,2-a][1,6]naphthyridin-8-yl)amino)-5-morpholinopyridin-3-yl)acrylamide | 620.2 |

(CDCl$_3$) δ 8.71(s, 1H), 8.18(s, 1H), 7.97(s, 2H), 7.88(s, 1H), 7.62(dd, 1H), 7.34(s, 1H), 6.69(s, 1H), 6.41(m, 3H), 5.80(dd, 1H), 3.97(s, 6H), 3.90(t, 4H), 3.24(t, 4H)

| 87 | 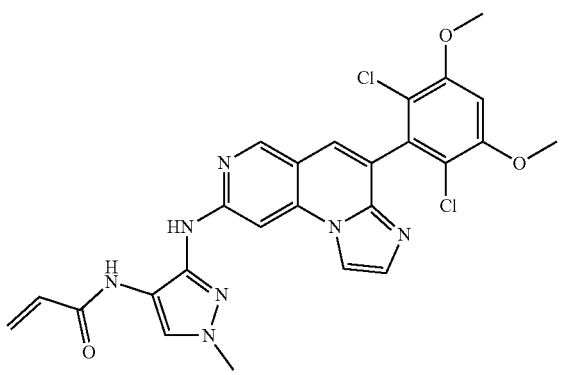 [SMILES: C=CC(=O)Nc1cn(C)nc1Nc1cc2c(cn1)cc(-c1c(Cl)c(OC)cc(OC)c1Cl)c1nccn12] | N-(3-((4-(2,6-dichloro-3,5-dimethoxyphenyl)imidazo[1,2-a][1,6]naphthyridin-8-yl)amino)-1-methyl-1H-pyrazol-4-yl)acrylamide | 538.1 |

(CDCl$_3$) δ 8.71 (s, 1H), 7.98 (m, 2H), 7.31 (m, 2H), 7.26 (m, 2H), 6.60 (s, 1H), 6.26 (m, 1H), 6.18 (d, 1H), 5.71 (d, 1H), 5.30 (m, 1H), 3.92 (s, 6H), 3.40 (s, 3H)

Test Example 1: Test on Activity Inhibition for FGFR1, 4 Kinase

For the synthesized compounds, inhibitory activity for FGFR1, 2, 3, 4 kinase was measured. Activity measurement was carried out by requesting to SelectScreen® Biochemical Kinase Profiling Service of Invitrogen. A Z'-LYTE® biochemical assay method was used, and the ATP concentration was set based on the Km value. As the results, kinase activity inhibition of the control group is shown as percentage in the following Table 1.

Test Example 2: Measuring Inhibitory Effect of FGFR Inhibitor Using Cell Line The test was carried out for identifying a proliferation inhibitory effect of the compound of the present invention for HUH7 cells. HUH7 cell lines were counted and $5.0 \times 10^3$ cells were inoculated per well in a 96 well plate. After the innoculation, the cells were cultured for 24 hours in a 37 □ and 5% carbon dioxide ($CO_2$) incubator. On the next day, the synthesized compounds were each diluted and prepared. The diluted compounds were introduced to the cell lines inoculated the previous day by concentrations, and reacted for 72 hours in a 37 □ and 5% carbon dioxide ($CO_2$) incubator. However, to a positive control to which the compound was not added, 0.1% dimethyl sulfoxide (DMSO) diluted with a medium was introduced. To a negative control plate, a trichloroacetic acid (TCA) solution was introduced, and fixed at 4 □. After reacting for 72 hours, the medium including the compound was removed, a TCA solution was added thereto, and the cells were fixed for 30 minutes to 60 minutes at 4 □. The TCA solution was discarded, the plate was washed off with distilled water and then dried in the air. A 0.4% sulforhodamin B (SRB) solution was added to the plate and dyed for 10 minutes at room temperature. The plate was washed off with tap water including a 1% acetic acid solution, and then dried in the air. A 10 mM Trizma base solution was added to dissolve the solid SRB. Using a microplate reader, optical density (O.D. value) was measured at 540 nm. A $GI_{50}$ value of each of the compounds was calculated using GraphPad Prism V6.0 Software. The results are shown in the following Table 1.

TABLE 1

| Synthesis Example No. | $IC_{50}$ FGFR4 | $IC_{50}$ FGFR1 | HUH7 Cell Line |
|---|---|---|---|
| 1 | — | — | B |
| 2 | — | — | B |
| 3 | — | — | B |
| 4 | A | B | B |
| 5 | — | — | B |
| 6 | A | A | A |
| 7 | — | — | A |
| 8 | — | — | C |
| 9 | A | C | B |
| 10 | A | B | A |
| 11 | A | B | B |
| 12 | — | — | B |
| 13 | — | — | A |
| 14 | — | — | B |
| 15 | — | — | B |
| 16 | — | — | B |
| 17 | — | — | B |
| 18 | A | A | B |
| 19 | A | B | A |
| 20 | — | — | B |
| 21 | — | — | B |
| 22 | — | — | B |
| 23 | — | — | A |
| 24 | A | A | A |
| 25 | A | A | A |
| 26 | A | B | A |
| 27 | — | — | A |
| 28 | — | — | A |
| 29 | A | A | A |
| 30 | — | — | A |
| 31 | A | A | A |
| 32 | A | A | A |
| 33 | — | — | B |
| 34 | — | — | B |
| 35 | A | A | A |
| 36 | A | A | A |
| 37 | A | A | A |
| 38 | A | A | A |
| 39 | A | A | A |
| 40 | — | — | A |
| 41 | — | — | A |
| 42 | — | — | A |
| 43 | — | — | A |
| 44 | — | — | A |
| 45 | — | — | A |
| 46 | — | — | A |
| 47 | — | — | A |
| 48 | A | A | A |
| 49 | — | — | A |
| 50 | — | — | A |
| 51 | — | — | B |
| 52 | A | A | A |
| 53 | A | A | A |
| 54 | B | C | B |
| 55 | — | — | B |
| 56 | — | — | A |
| 57 | — | — | B |
| 58 | B | C | B |
| 59 | — | — | A |
| 60 | — | — | B |
| 61 | A | A | A |
| 62 | — | — | A |
| 63 | A | B | B |
| 64 | — | — | C |
| 65 | — | — | B |
| 66 | — | — | C |
| 67 | — | — | B |
| 68 | — | — | C |
| 69 | — | — | B |
| 70 | — | — | B |
| 71 | — | — | B |
| 72 | A | C | A |
| 73 | A | A | A |
| 74 | — | — | A |
| 75 | — | — | A |
| 76 | — | — | B |
| 77 | — | — | B |
| 78 | — | — | B |
| 79 | — | — | B |
| 80 | — | — | C |
| 81 | — | — | C |
| 82 | — | — | C |
| 83 | A | A | A |
| 84 | — | — | A |
| 85 | A | A | A |
| 86 | — | — | A |
| 87 | — | — | A |

(A: <50 nM; B: >50 nM, <500 nM; C: >500 nM; —: Not Measured)

As shown in Table 1, it was seen that the compounds of Synthesis Examples 1 to 87 of the present invention had excellent inhibitory activity particularly for FGFR4 among fibroblast growth factor receptors.

The heterocyclic derivative compound represented by Chemical Formula 1 provided in the present invention has excellent selective inhibitory activity for FGFR, and therefore, is useful for preventing or treating various diseases relating to the FGFR.

Hereinbefore, the present invention has been described focusing on the above-described examples, however, it is to be understood that these are for illustrative purposes only, and, in the present invention, various modifications and equivalent other examples obvious to those skilled in the art may be implemented within the scope of the attached claims.

What is claimed is:

1. A compound selected from the group consisting of a heterocyclic compounds of the following Chemical Formula 1, a pharmaceutically acceptable salt, an optical isomer, a hydrate, and a solvate thereof:

Chemical Formula 1

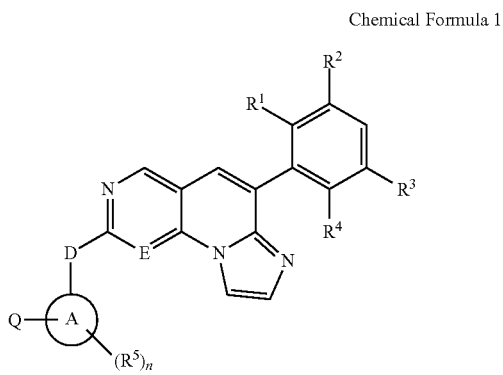

wherein, in Chemical Formula 1,
$R^1$, $R^2$, $R^3$ and $R^4$ are each independently selected from the group consisting of H, halogen, $C_{1-4}$ alkyl and $C_{1-4}$ alkoxy;
E is CH or N;
D is NH or a bond;
Q is

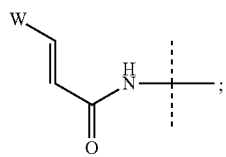

W is hydrogen, halogen or —$(CH_2)_p NR^a R^b$;
$R^a$ and $R^b$ are each independently selected from the group consisting of H or $C_{1-6}$ alkyl, and herein, $R^a$ and $R^b$ may bond to each other to form a $C_{3-6}$ alkylene bridge, and at least one methylene in the alkylene bridge is unreplaced or replaced by one or more members selected from the group consisting of —O—, —S(O)—, —S(O)$_2$— and —N(R')—;
ring A is selected from the group consisting of aryl, heteroaryl, cycloalkyl and heterocyclyl, and herein, the heteroaryl means a 5-membered to 7-membered aromatic ring containing 1 to 3 heteroatoms selected from the group consisting of O, N and S, and the heterocyclyl means a 5-membered to 7-membered ring containing 1 to 3 heteroatoms or functional groups selected from the group consisting of N, O, S, SO and SO$_2$;
$R^5$ is selected from the group consisting of halogen, $C_{1-6}$ alkyl, $C_{2-6}$ alkenyl, $C_{2-6}$ alkynyl, —CN, —$(CH_2)_p$ NR'R", —N(R')$(CH_2)_p$OR$^6$, —$(CH_2)_p$OR$^6$, aryl, heteroaryl, $C_{3-7}$ cycloalkyl, heterocyclyl, —$(CH_2)_p$C(=O)NR'R", —$(CH_2)_p$C(=O)R$^6$, —$(CH_2)_p$SR$^6$ and —$(CH_2)_p$SO$_2$R$^6$, and herein, the heterocyclyl means a 3-membered to 7-membered ring containing 1 to 3 heteroatoms or functional groups selected from the group consisting of N, O, S, SO and SO$_2$;
when there are a plurality of $R^5$s, these are the same as or different from each other, and $R^5$s adjacent to each other may bond to each other to form a $C_{3-6}$ alkylene bridge, and at least one methylene in the alkylene bridge is unreplaced or replaced by one or more members selected from the group consisting of —O—, —S(O)—, —S(O)$_2$— and —N(R')—;
$R^6$ is selected from the group consisting of hydrogen, halogen, hydroxy, $C_{1-6}$ alkyl, —$(CH_2)_q$NR'R", —$(CH_2)_q$OR$^7$, $C_{3-7}$ cycloalkyl, heterocyclyl, —$(CH_2)_q$ C(=O)R$^7$, —$(CH_2)_q$SR$^7$ and —$(CH_2)_q$SO$_2$R$^7$;
$R^7$ is selected from the group consisting of hydrogen, halogen, $C_{1-6}$ alkyl, $C_{3-7}$ cycloalkyl and heterocyclyl;
the $C_{1-6}$ alkyl of $R^5$ to $R^7$ are each independently unsubstituted or substituted with one or more types of substituents selected from the group consisting of halogen, hydroxy, —CN, linear or branched $C_{1-6}$ alkyl, halogenated $C_{1-6}$ alkyl, $C_{3-7}$ cycloalkyl and heterocyclyl;
the cycloalkyl and the heterocyclyl of $R^5$ to $R^7$, and the aryl and the heteroaryl of $R^5$ are each independently unsubstituted or additionally substituted with one or more types of substituents selected from the group consisting of halogen, hydroxy, —CN, linear or branched $C_{1-6}$ alkyl, halogenated $C_{1-6}$ alkyl, —NR'R", $C_{1-6}$ alkoxy, —C(=O)$C_{3-7}$ cycloalkyl, $C_{3-7}$ cycloalkyl and heterocyclyl;
the R' and the R" of $R^a$, $R^b$, $R^5$, and $R^6$ are each independently selected from the group consisting of H or $C_{1-6}$ alkyl;
p and q are each independently an integer of 0 to 6; and
n is an integer of 0 to 4.

2. The compound of claim 1, wherein E is N.

3. The compound of claim 1, wherein the compound represented by Chemical Formula 1 is represented by the following Chemical Formula 2 to Chemical Formula 5:

Chemical Formula 2

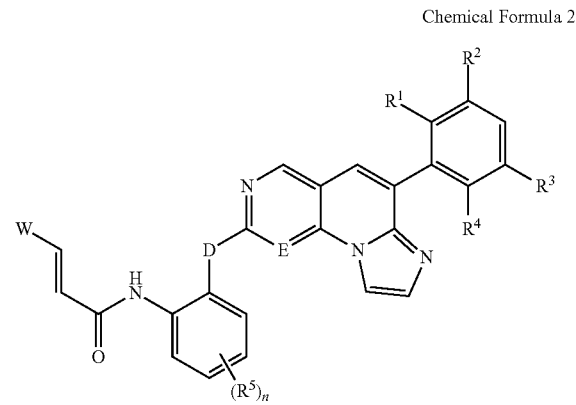

Chemical Formula 3

Chemical Formula 4

Chemical Formula 5 wherein, in Chemical Formula 2 to Chemical Formula 5,
X is selected from the group consisting of O, S, NH and $CH_2$;

m is an integer of 0 to 2;

one or more of $Z^1$ to $Z^4$ are N, and the rest are each independently N or $C(R^5)$;

Y is selected from the group consisting of O, S and $N(R^5)$; and $R^1$ to $R^5$, D, E, W, and n have the same definitions as in Chemical Formula 1.

4. The compound of claim 3, wherein, in the compound represented by Chemical Formula 3, any one of $Z^1$ to $Z^4$ is N, and the rest are $C(R^5)$.

5. The compound of claim 3, wherein, in the compound represented by Chemical Formula 4, Y is $N(R^5)$, and any one of $Z^1$ and $Z^2$ is N.

6. The compound of claim 1, wherein the compound of Chemical Formula 1 is selected from the group consisting of the following compounds:

N-(2-((6-(2,6-dichloro-3,5-dimethoxyphenyl)imidazo[1',2':1,6]pyrido[2,3-d]pyrimidin-2-yl)amino)cyclopentyl)acrylamide;

N-(2-((6-(2,6-dichloro-3,5-dimethoxyphenyl)imidazo[1',2':1,6]pyrido[2,3-d]pyrimidin-2-yl)amino)cyclohexyl)acrylamide;

N-(4-((6-(2,6-dichloro-3,5-dimethoxyphenyl)imidazo[1',2':1,6]pyrido[2,3-d]pyrimidin-2-yl)amino)tetrahydrofuran-3-yl)acrylamide;

N-((3S,4S)-3-((6-(2,6-dichloro-3,5-dimethoxyphenyl)imidazo[1',2':1,6]pyrido[2,3-d]pyrimidin-2-yl)amino)tetrahydro-2H-pyran-4-yl)acrylamide;

N-((3S,4S)-3-((6-(2,6-difluoro-3,5-dimethoxyphenyl)imidazo[1',2':1,6]pyrido[2,3-d]pyrimidin-2-yl)amino)tetrahydro-2H-pyran-4-yl)acrylamide;

N-(2-((6-(2,6-dichloro-3,5-dimethoxyphenyl)imidazo[1',2':1,6]pyrido[2,3-d]pyrimidin-2-yl)amino)phenyl)acrylamide;

N-(3-((6-(2,6-dichloro-3,5-dimethoxyphenyl)imidazo[1',2':1,6]pyrido[2,3-d]pyrimidin-2-yl)amino)phenyl)acrylamide;

N-(2-((6-(3,5-dimethoxyphenyl)imidazo[1',2':1,6]pyrido[2,3-d]pyrimidin-2-yl)amino)-3-methylphenyl)acrylamide;

N-(2-((6-(2,6-dichloro-3,5-dimethoxyphenyl)imido[1',2':1,6]pyrido[2,3-d]pyrimidin-2-yl)amino)-3-methylphenyl)acrylamide;

N-(2-((6-(2,6-dichloro-3,5-dimethoxyphenyl)imidazo[1',2':1,6]pyrido[2,3-d]pyrimidin-2-yl)amino)-3-fluorophenyl)acrylamide;

N-(2-((6-(2,6-dichloro-3,5-dimethoxyphenyl)imidazo[1',2':1,6]pyrido[2,3-d]pyrimidin-2-yl)amino)-3-methoxyphenyl)acrylamide;

N-(2-((6-(2,6-dichloro-3,5-dimethoxyphenyl)imidazo[1',2':1,6]pyrido[2,3-d]pyrimidin-2-yl)amino)-4-fluorophenyl)acrylamide;

N-(2-((6-(2,6-dichloro-3,5-dimethoxyphenyl)imidazo[1',2':1,6]pyrido[2,3-d]pyrimidin-2-yl)amino)-4-(4-ethylpiperazin-1-yl)phenyl)acrylamide;

N-(2-((6-(2,6-dichloro-3,5-dimethoxyphenyl)imidazo[1',2':1,6]pyrido[2,3-d]pyrimidin-2-yl)amino)-5-fluorophenyl)acrylamide;

N-(5-chloro-2-((6-(2,6-dichloro-3,5-dimethoxyphenyl)imidazo[1',2':1,6]pyrido[2,3-d]pyrimidin-2-yl)amino)phenyl)acrylamide;

N-(2-((6-(2,6-dichloro-3,5-dimethoxyphenyl)imidazo[1',2':1,6]pyrido[2,3-d]pyrimidin-2-yl)amino)-5-ethynylphenyl)acrylamide;

N-(5-cyano-2-((6-(2,6-dichloro-3,5-dimethoxyphenyl)imidazo[1',2':1,6]pyrido[2,3-d]pyrimidin-2-yl)amino)phenyl)acrylamide;

N-(2-((6-(2,6-dichloro-3,5-dimethoxyphenyl)imidazo[1',2':1,6]pyrido[2,3-d]pyrimidin-2-yl)amino)-5-(methylsulfonyl)phenyl)acrylamide;

N-(2-((6-(2,6-dichloro-3,5-dimethoxyphenyl)imidazo[1',2':1,6]pyrido[2,3-d]pyrimidin-2-yl)amino)-5-methylphenyl)acrylamide;

N-(2-((6-(2,6-dichloro-3,5-dimethoxyphenyl)imidazo[1',2':1,6]pyrido[2,3-d]pyrimidin-2-yl)amino)-5-ethylphenyl)acrylamide;

N-(5-cyclopropyl-2-((6-(2,6-dichloro-3,5-dimethoxyphenyl)imidazo[1',2':1,6]pyrido[2,3-d]pyrimidin-2-yl)amino)phenyl)acrylamide;

N-(2-((6-(2,6-dichloro-3,5-dimethoxyphenyl)imidazo[1',2':1,6]pyrido[2,3-d]pyrimidin-2-yl)amino)-5-isopropylphenyl)acrylamide;

N-(2-((6-(2,6-dichloro-3,5-dimethoxyphenyl)imidazo[1',2':1,6]pyrido[2,3-d]pyrimidin-2-yl)amino)-5-(1-methylpiperidin-4-yl)phenyl)acrylamide;

N-(2-((6-(2,6-dichloro-3,5-dimethoxyphenyl)imidazo[1', 2':1,6]pyrido[2,3-d]pyrimidin-2-yl)amino)-5-(dimethylamino)phenyl)acrylamide;

N-(2-((6-(2,6-dichloro-3,5-dimethoxyphenyl)imidazo[1', 2':1,6]pyrido[2,3-d]pyrimidin-2-yl)amino)-5-((2-methoxyethyl)(methyl)amino)phenyl)acrylamide;

N-(2-((6-(2,6-dichloro-3,5-dimethoxyphenyl)imidazo[1', 2':1,6]pyrido[2,3-d]pyrimidin-2-yl)amino)-5-methoxyphenyl)acrylamide;

N-(2-((6-(2,6-dichloro-3,5-dimethoxyphenyl)imidazo[1', 2':1,6]pyrido[2,3-d]pyrimidin-2-yl)amino)-5-ethoxyphenyl)acrylamide;

N-(2-((6-(2,6-dichloro-3,5-dimethoxyphenyl)imidazo[1', 2':1,6]pyrido[2,3-d]pyrimidin-2-yl)amino)-5-isopropoxyphenyl)acrylamide;

N-(2-((6-(2,6-dichloro-3,5-dimethoxyphenyl)imidazo[1', 2':1,6]pyrido[2,3-d]pyrimidin-2-yl)amino)-5-(2-methoxyethoxy)phenyl)acrylamide;

N-(2-((6-(2,6-dichloro-3,5-dimethoxyphenyl)imidazo[1', 2':1,6]pyrido[2,3-d]pyrimidin-2-yl)amino)-5-(2-(dimethylamino)ethoxy)phenyl)acrylamide;

N-(2-((6-(2,6-dichloro-3,5-dimethoxyphenyl)imidazo[1', 2':1,6]pyrido[2,3-d]pyrimidin-2-yl)amino)-5-(4-ethylpiperazin-1-yl)phenyl)acrylamide;

N-(2-((6-(2,6-dichloro-3,5-dimethoxyphenyl)imidazo[1', 2':1,6]pyrido[2,3-d]pyrimidin-2-yl)amino)-5-morpholinophenyl)acrylamide;

N-(2-((6-(2,6-dichloro-3,5-dimethoxyphenyl)imidazo[1', 2':1,6]pyrido[2,3-d]pyrimidin-2-yl)amino)-5-(pyrrolidin-1-yl)phenyl)acrylamide;

(E)-N-(2-((6-(2,6-dichloro-3,5-dimethoxyphenyl)imidazo[1',2':1,6]pyrido[2,3-d]pyrimidin-2-yl)amino)-5-morpholinophenyl)-4-(dimethylamino)but-2-eneamide;

N-(2-((6-(2,6-dichloro-3,5-dimethoxyphenyl)imidazo[1', 2':1,6]pyrido[2,3-d]pyrimidin-2-yl)amino)-5-(4-(methylsulfonyl)piperazin-1-yl)phenyl)acrylamide;

N-(2-((6-(2,6-dichloro-3,5-dimethoxyphenyl)imidazo[1', 2':1,6]pyrido[2,3-d]pyrimidin-2-yl)amino)-5-(1,1-dioxidothiomorpholino)phenyl)acrylamide;

N-(2-((6-(2,6-dichloro-3,5-dimethoxyphenyl)imidazo[1', 2':1,6]pyrido[2,3-d]pyrimidin-2-yl)amino)-5-(3-methoxyazetidin-1-yl)phenyl)acrylamide;

N-(2-((6-(2,6-dichloro-3,5-dimethoxyphenyl)imidazo[1', 2':1,6]pyrido[2,3-d]pyrimidin-2-yl)amino)-5-((2S,6R)-2,6-dimethylmorpholino)phenyl)acrylamide;

N-(2-((6-(2,6-dichloro-3,5-dimethoxyphenyl)imidazo[1', 2':1,6]pyrido[2,3-d]pyrimidin-2-yl)amino)-5-(piperazin-1-yl)phenyl)acrylamide trifluoroacetate;

N-(2-((6-(2,6-dichloro-3,5-dimethoxyphenyl)imidazo[1', 2':1,6]pyrido[2,3-d]pyrimidin-2-yl)amino)-5-(4-methoxypiperidin-1-yl)phenyl)acrylamide;

N-(2-((6-(2,6-dichloro-3,5-dimethoxyphenyl)imidazo[1', 2':1,6]pyrido[2,3-d]pyrimidin-2-yl)amino)-5-(3-methoxypyrrolidin-1-yl)phenyl)acrylamide;

N-(5-(4-(cyclopropanecarbonyl)piperazin-1-yl)-2-((6-(2,6-dichloro-3,5-dimethoxyphenyl)imidazo[1',2':1,6]pyrido[2,3-d]pyrimidin-2-yl)amino)phenyl)acrylamide;

N-(5-(4-(cyclopropylmethyl)piperazin-1-yl)-2-((6-(2,6-dichloro-3,5-dimethoxyphenyl)imidazo[1',2':1,6]pyrido[2,3-d]pyrimidin-2-yl)amino)phenyl)acrylamide;

(S)—N-(2-((6-(2,6-dichloro-3,5-dimethoxyphenyl)imidazo[1',2':1,6]pyrido[2,3-d]pyrimidin-2-yl)amino)-5-(3-methoxypyrrolidin-1-yl)phenyl)acrylamide;

N-(2-((6-(2,6-dichloro-3,5-dimethoxyphenyl)imidazo[1', 2':1,6]pyrido[2,3-d]pyrimidin-2-yl)amino)-5-(3-hydroxyazetidin-1-yl)phenyl)acrylamide;

N-(2-((6-(2,6-dichloro-3,5-dimethoxyphenyl)imidazo[1', 2':1,6]pyrido[2,3-d]pyrimidin-2-yl)amino)-5-(4-(2-methoxyethyl)piperazin-1-yl)phenyl)acrylamide;

(Z)-3-chloro-N-(2-((6-(2,6-dichloro-3,5-dimethoxyphenyl)imidazo[1',2':1,6]pyrido[2,3-d]pyrimidin-2-yl)amino)-5-morpholinophenyl)acrylamide;

(S)—N-(2-((6-(2,6-dichloro-3,5-dimethoxyphenyl)imidazo[1',2':1,6]pyrido[2,3-d]pyrimidin-2-yl)amino)-5-(3-(dimethylamino)pyrrolidin-1-yl)phenyl)acrylamide;

N-(2-((6-(2,6-dichloro-3,5-dimethoxyphenyl)imidazo[1', 2':1,6]pyrido[2,3-d]pyrimidin-2-yl)amino)-5-(2-methylmorpholino)phenyl)acrylamide;

(S)—N-(2-((6-(2,6-dichloro-3,5-dimethoxyphenyl)imidazo[1',2':1,6]pyrido[2,3-d]pyrimidin-2-yl)amino)-5-(2-(methoxymethyl)pyrrolidin-1-yl)phenyl)acrylamide;

N-(5-(4-cyclopropylpiperazin-1-yl)-2-((6-(2,6-dichloro-3,5-dimethoxyphenyl)imidazo[1',2':1,6]pyrido[2,3-d]pyrimidin-2-yl)amino)phenyl)acrylamide;

N-(2-((6-(2,6-dichloro-3,5-dimethoxyphenyl)imidazo[1', 2':1,6]pyrido[2,3-d]pyrimidin-2-yl)amino)-5-(4-methylpiperazin-1-yl)phenyl)acrylamide;

(R)—N-(2-((6-(2,6-dichloro-3,5-dimethoxyphenyl)imidazo[1',2':1,6]pyrido[2,3-d]pyrimidin-2-yl)amino)-5-((tetrahydrofuran-3-yl)oxy)phenyl)acrylamide;

N-(5-(cyclopentyloxy)-2-((6-(2,6-dichloro-3,5-dimethoxyphenyl)imidazo[1',2':1,6]pyrido[2,3-d]pyrimidin-2-yl)amino)phenyl)acrylamide;

N-(2-((6-(2,6-dichloro-3,5-dimethoxyphenyl)imidazo[1', 2':1,6]pyrido[2,3-d]pyrimidin-2-yl)amino)-5-((1-(2,2,2-trifluoroethyl)piperidin-4-yl)oxy)phenyl)acrylamide;

N-(2-((6-(2,6-dichloro-3,5-dimethoxyphenyl)imidazo[1', 2':1,6]pyrido[2,3-d]pyrimidin-2-yl)amino)-5-((1-ethylpiperidin-4-yl)oxy)phenyl)acrylamide;

N-(6-((6-(2,6-dichloro-3,5-dimethoxyphenyl)imidazo[1', 2':1,6]pyrido[2,3-d]pyrimidin-2-yl)amino)-2,3-dihydro-1H-inden-5-yl)acrylamide;

N-(2-((6-(2,6-dichloro-3,5-dimethoxyphenyl)imidazo[1', 2':1,6]pyrido[2,3-d]pyrimidin-2-yl)amino)-3,5-dimethylphenyl)acrylamide;

(R)—N-(2-((6-(2,6-dichloro-3,5-dimethoxyphenyl)imidazo[1',2':1,6]pyrido[2,3-d]pyrimidin-2-yl)amino)-4-fluoro-5-((tetrahydrofuran-3-yl)oxy)phenyl)acrylamide;

(R)—N-(2-((6-(2,6-dichloro-3,5-dimethoxyphenyl)imidazo[1',2':1,6]pyrido[2,3-d]pyrimidin-2-yl)amino)-4-methyl-5-((tetrahydrofuran-3-yl)oxy)phenyl)acrylamide;

N-(2-((6-(2,6-dichloro-3,5-dimethoxyphenyl)imidazo[1', 2':1,6]pyrido[2,3-d]pyrimidin-2-yl)amino)-4-methyl-5-morpholinophenyl)acrylamide;

N-(2-((6-(2,6-dichloro-3,5-dimethoxyphenyl)imidazo[1', 2':1,6]pyrido[2,3-d]pyrimidin-2-yl)amino)-4-fluoro-5-((1-methylpiperidin-4-yl)oxy)phenyl)acrylamide;

N-(2-((6-(2,6-dichloro-3,5-dimethoxyphenyl)imidazo[1', 2':1,6]pyrido[2,3-d]pyrimidin-2-yl)amino)-3-methyl-5-morpholinophenyl)acrylamide;

N-(2-((6-(2,6-dichloro-3,5-dimethoxyphenyl)imidazo[1', 2':1,6]pyrido[2,3-d]pyrimidin-2-yl)amino)-5-fluoro-3-methylphenyl)acrylamide;

N-(2-((6-(2,6-dichloro-3,5-dimethoxyphenyl)imidazo[1', 2':1,6]pyrido[2,3-d]pyrimidin-2-yl)amino)-3-methoxy-5-morpholinophenyl)acrylamide;

N-(2-((6-(2,6-dichloro-3,5-dimethoxyphenyl)imidazo[1',2':1,6]pyrido[2,3-d]pyrimidin-2-yl)amino)-5-(4-ethylpiperazin-1-yl)-3-fluorophenyl)acrylamide;

N-(2-((6-(2,6-dichloro-3,5-dimethoxyphenyl)imidazo[1',2':1,6]pyrido[2,3-d]pyrimidin-2-yl)amino)-3-fluoro-5-morpholinophenyl)acrylamide;

N-(3-chloro-2-((6-(2,6-dichloro-3,5-dimethoxyphenyl)imidazo[1',2':1,6]pyrido[2,3-d]pyrimidin-2-yl)amino)-5-morpholinophenyl)acrylamide;

N-(2-((6-(2,6-difluoro-3,5-dimethoxyphenyl)imidazo[1',2':1,6]pyrido[2,3-d]pyrimidin-2-yl)amino)-3-fluorophenyl)acrylamide;

N-(2-((6-(2,6-difluoro-3,5-dimethoxyphenyl)imidazo[1',2':1,6]pyrido[2,3-d]pyrimidin-2-yl)amino)-5-morpholinophenyl)acrylamide;

N-(2-((6-(2,6-dichloro-3,5-dimethoxyphenyl)imidazo[1',2':1,6]pyrido[2,3-d]pyrimidin-2-yl)amino)pyridin-3-yl)acrylamide;

N-(2-((6-(2,6-dichloro-3,5-dimethoxyphenyl)imidazo[1',2':1,6]pyrido[2,3-d]pyrimidin-2-yl)amino)-5-morpholinopyridin-3-yl)acrylamide;

N-(3-((6-(2,6-dichloro-3,5-dimethoxyphenyl)imidazo[1',2':1,6]pyrido[2,3-d]pyrimidin-2-yl)amino)-1-methyl-1H-pyrazol-4-yl)acrylamide;

N-(2-((6-(2,6-difluoro-3,5-dimethoxyphenyl)imidazo[1',2':1,6]pyrido[2,3-d]pyrimidin-2-yl)amino)-3-fluorophenyl)acrylamide;

N-(2-((6-(2,6-difluoro-3,5-dimethoxyphenyl)imidazo[1',2':1,6]pyrido[2,3-d]pyrimidin-2-yl)amino)-5-morpholinophenyl)acrylamide;

N-(3-((6-(2,6-difluoro-3,5-dimethoxyphenyl)imidazo[1',2':1,6]pyrido[2,3-d]pyrimidin-2-yl)amino)phenyl)acrylamide;

N-(2-((6-(2,6-difluoro-3,5-dimethoxyphenyl)imidazo[1',2':1,6]pyrido[2,3-d]pyrimidin-2-yl)amino)phenyl)acrylamide;

N-(2-((6-(2,6-difluoro-3,5-dimethoxyphenyl)imidazo[1',2':1,6]pyrido[2,3-d]pyrimidin-2-yl)amino)-3,5-difluorophenyl)acrylamide;

N-(2-((6-(2,6-difluoro-3,5-dimethoxyphenyl)imidazo[1',2':1,6]pyrido[2,3-d]pyrimidin-2-yl)amino)-4,5-difluorophenyl)acrylamide;

N-(2-((6-(2,6-difluoro-3,5-dimethoxyphenyl)imidazo[1',2':1,6]pyrido[2,3-d]pyrimidin-2-yl)amino)-3,4-difluorophenyl)acrylamide;

N-(3-chloro-2-((6-(2,6-difluoro-3,5-dimethoxyphenyl)imidazo[1',2':1,6]pyrido[2,3-d]pyrimidin-2-yl)amino)phenyl)acrylamide;

N-(3-(6-(2,6-dichloro-3,5-dimethoxyphenyl)imidazo[1',2':1,6]pyrido[2,3-d]pyrimidin-2-yl)-5-morpholinophenyl)acrylamide;

N-(2-((4-(2,6-dichloro-3,5-dimethoxyphenyl)imidazo[1,2-a][1,6]naphthyridin-8-yl)amino)-5-morpholinophenyl)acrylamide;

N-(2-((4-(2,6-dichloro-3,5-dimethoxyphenyl)imidazo[1,2-a][1,6]naphthyridin-8-yl)amino)-5-((2S,6R)-2,6-dimethylmorpholino)phenyl)acrylamide;

N-(2-((4-(2,6-dichloro-3,5-dimethoxyphenyl)imidazo[1,2-a][1,6]naphthyridin-8-yl)amino)-5-(4-ethylpiperazin-1-yl)phenyl)acrylamide;

N-(2-((4-(2,6-dichloro-3,5-dimethoxyphenyl)imidazo[1,2-a][1,6]naphthyridin-8-yl)amino)-5-morpholinopyridin-3-yl)acrylamide; and N-(3-((4-(2,6-dichloro-3,5-dimethoxyphenyl)imidazo[1,2-a][1,6]naphthyridin-8-yl)amino)-1-methyl-1H-pyrazol-4-yl)acrylamide.

7. A pharmaceutical composition comprising the compound of claim 1.

8. A pharmaceutical formulation comprising the pharmaceutical composition of claim 7, which has a form of a tablet, a pill, a powder, a capsule, a syrup or an emulsion.

9. The pharmaceutical formulation of claim 8, further comprising one or more members selected from the group consisting of a pharmaceutically acceptable carrier, an adjuvant and a vehicle.

10. A method for inhibiting activity of a fibroblast growth factor receptor (FGFR) comprising administering to a patient in need thereof an inhibitory amount of the compound of claim 1.

11. A method for treating a cancer, comprising administering to a patient in need thereof a therapeutically effective amount of the compound of claim 1, wherein the cancer is liver cancer.

12. The method of claim 11, wherein the liver cancer is hepatocellular cancer.

* * * * *